(12) United States Patent
Rush et al.

(10) Patent No.: US 7,300,753 B2
(45) Date of Patent: Nov. 27, 2007

(54) IMMUNOAFFINITY ISOLATION OF MODIFIED PEPTIDES FROM COMPLEX MIXTURES

(76) Inventors: John Rush, 1809 Beacon St., Brookline, MA (US) 02466; Hui Zhang, 3221 NE. 96th St., Seattle, WA (US) 98115; Xiangming Zha, 900 W. Benton St., Apt. 11, Iowa City, IA (US) 52246; Michael J. Comb, 27 Proctor St., Manchester, MA (US) 01944; Yi Tan, 2 Heath Cir., Lynnfield, MA (US) 01940

( * ) Notice: Subject to any disclaimer, the term of this patent is extended or adjusted under 35 U.S.C. 154(b) by 0 days.

(21) Appl. No.: 10/777,893

(22) Filed: Feb. 12, 2004

(65) Prior Publication Data
US 2005/0003450 A1   Jan. 6, 2005

Related U.S. Application Data

(63) Continuation-in-part of application No. 10/175,486, filed on Jun. 19, 2002, and a continuation-in-part of application No. 09/535,364, filed on Mar. 24, 2000, now Pat. No. 6,982,318, and a continuation-in-part of application No. 09/148,712, filed on Sep. 4, 1998, now Pat. No. 6,441,140.

(60) Provisional application No. 60/299,893, filed on Jun. 21, 2001, provisional application No. 60/337,012, filed on Nov. 8, 2001.

(51) Int. Cl.
*C12Q 1/00*   (2006.01)
*C12Q 1/37*   (2006.01)
*C12P 21/06*   (2006.01)
*G01N 33/543* (2006.01)

(52) U.S. Cl. ............... 435/6; 435/4; 435/69.1; 435/24; 435/174; 436/518; 436/89; 436/501; 216/601; 216/661; 216/656

(58) Field of Classification Search ............ 435/6, 435/4, 69.1, 174; 436/518, 89, 501; 210/601, 210/656, 661
See application file for complete search history.

(56) References Cited

U.S. PATENT DOCUMENTS

5,885,841 A   3/1999   Higgs, Jr. et al.

(Continued)

OTHER PUBLICATIONS

Wirth et al. The rat liver epithelial (RLE) cell nuclear protein database. Electrophoresis 1993, 14, 1199-1215.*

(Continued)

*Primary Examiner*—Long V. Le
*Assistant Examiner*—Pensee T. Do

(57) ABSTRACT

The invention provides methods for isolating a modified peptide from a complex mixture of peptides, the method comprising the steps of: (a) obtaining a proteinaceous preparation from an organism, wherein the preparation comprises modified peptides from two or more different proteins; (b) contacting the preparation with at least one immobilized modification-specific antibody; and (c) isolating at least one modified peptide specifically bound by the immobilized modification-specific antibody in step (b). The method may further comprise the step of (d) characterizing the modified peptide isolated in step (c) by mass spectrometry (MS), tandem mass spectrometry (MS—MS), and/or MS³ analysis, or the step of (e) utilizing a search program to substantially match the spectra obtained for the modified peptide during the characterization of step (d) with the spectra for a known peptide sequence, thereby identifying the parent protein(s) of the modified peptide. Also provided are an immunoaffinity isolation device comprising a modification-specific antibody, and antibodies against novel UFD1 and PTN6 phosphorylation sites.

43 Claims, 35 Drawing Sheets

U.S. PATENT DOCUMENTS

| | | | |
|---|---|---|---|
| 5,965,352 A * | 10/1999 | Stoughton et al. | 435/4 |
| 6,291,645 B1 | 9/2001 | Shin et al. | |
| 6,322,970 B1 * | 11/2001 | Little et al. | 435/6 |
| 6,379,970 B1 | 4/2002 | Liebler et al. | |
| 6,441,140 B1 | 8/2002 | Comb et al. | |
| 6,451,591 B1 | 9/2002 | Edwards et al. | |
| 6,579,720 B1 * | 6/2003 | Pidgeon et al. | 436/161 |
| 6,818,454 B2 * | 11/2004 | Goshe et al. | 436/173 |

OTHER PUBLICATIONS

Kanner et al. Immunoaffinity purification of tyrosine-phosphorylated cellular proteins. Journal of Immunological Methods, 120 (1989) 115-124.*

Novagen Technical Bulletin, "pET System Manual", 9th Edition, May 2000.

Hoffman, et al., *J. of Immuno. Methods*, 112: pp. 113-120 (1988).

U.S. Appl. No. 10/777,893, filed Jun. 19, 2002, Rush et al.

Hunter, *Nature 411*: 355-65 (2001).

Graves et al., *Pharmacol. Ther. 82*: 111-21 (1999).

Wettenhall et al. *Methods Enzymol. 201* 186-199 (1991).

De Corte, et al., *Prot. Sci. 8*: 234-241 (1999).

Kalo et al., *Biochem. 38*: 14396-408 (1999).

Marcus, et al., *Electrophoresis* 21: 2622-2636 (2000).

Mann et al., *Trends in Biotech*. 20: 261-268 (2002).

Yu et al., *J. A.m. Soc. Mass. Spec. 9*: 208-215 (1998).

Mann et al., *Ann. Rev. Biochem.* 70: 437-473 (2001).

Posewitz et al., *Anal. Chem. 15*:2883-2892 (1999).

Mann, *Nat. Biotech. 17*: 954-55 (1999).

Conrads, et al., *Nature Biotechnology*, vol. 23 No. 1: 36-37, Jan. 2005.

Quadroni, et al, *Proteomics in Functional Genomics*, 2000: 88: 199-213, Review.

Stukenberg, et al., *Systematic Identification of Mitotic Phosphoproteins*, Current Biology, Current Science vol. 7, No. 5:338-348 (May 1997).

Ouyang, et al., *Multi-site Phospho-typing of the ErbB-2 Oncoprotein in Human Breast Cancer*, Molecular Diagnosis: A Journal Devoted to the Understanding of Human Disease Through the Clinical Application of Molecular Biology, vol. 6, No. 1:17-25 (Mar. 2001).

Yanagida, et al., *Matrix Assisted Laser Desorption/Ionization-Time of Flight-Mass Spectrometry Analysis of Proteins Detected by Anti-Phosphotyrosine Antibody on Two-Dimensional Gels of Fibroblast Cell Lysates After Tumor Necrosis Factor-alpha Stimulation*, Electrophoresis, vol. 21, No. 9:1890-1898 (May 2000).

Godovac-Zimmerman Jasminka, et al., *Functional Proteomics of Signal Transduction by Membrane Receptors*, Electrophoresis, vol. 20, No. 4-5:952-961 (Apr. 1999).

Kamps, MP, et al., *Generation and Use of Anti-Phosphotyrosine Antibodies for Immunoblotting*, Methods in Enzymology, vol. 201:101-110 (1991).

Reinders et al., *Proteomics 5*: 4052-4061 (2005).

Peters et al., *Mini-Rev. Med. Chem. 4*:313-324 (2004).

Raggiaschi et al., *Biosci. Reports 25*(1/2): 33-44 (2005).

\* cited by examiner

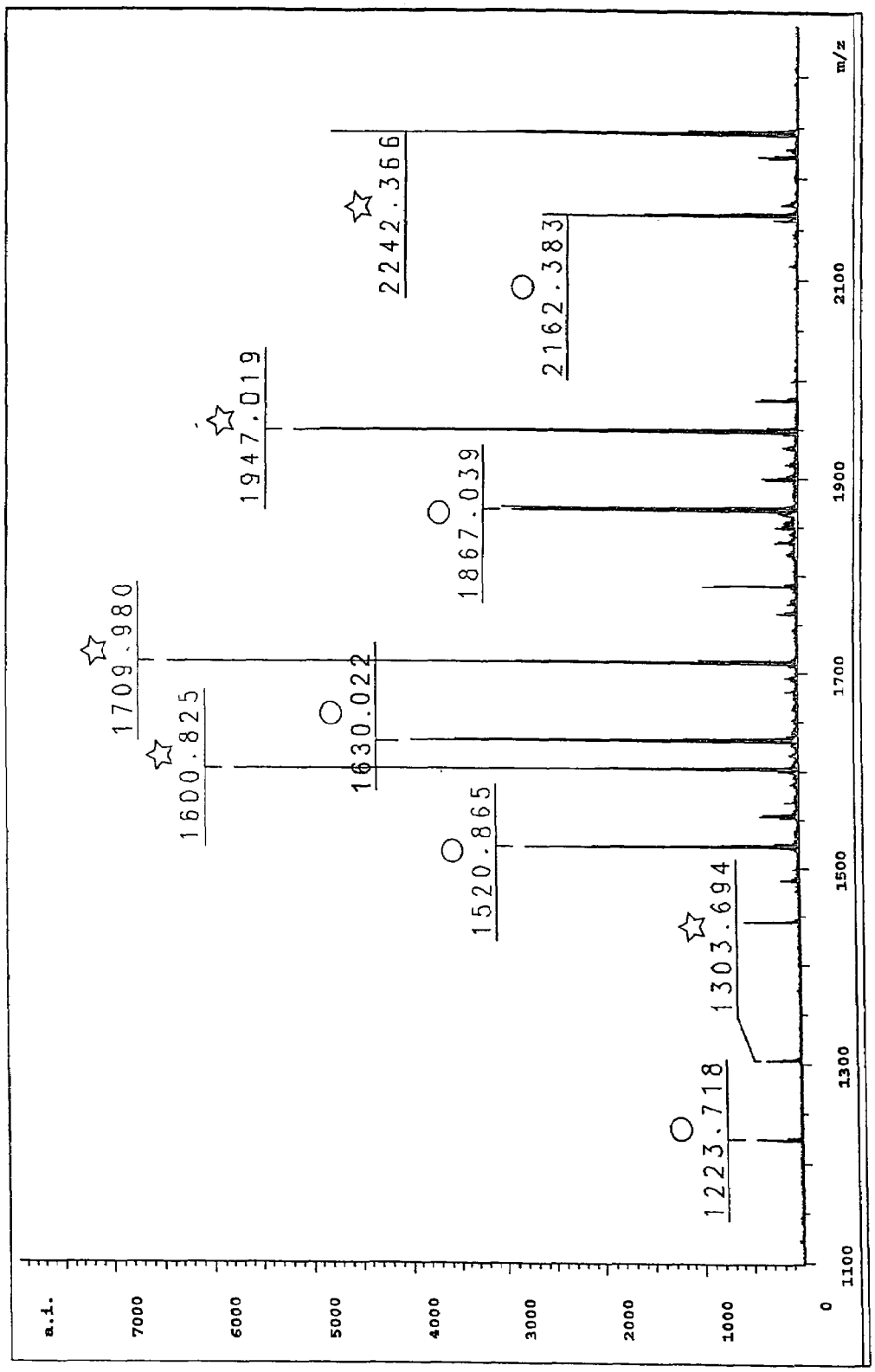
FIGURE 2: MALDI-TOF mass spectrum of an unpurified phosphotyrosine peptide mix.

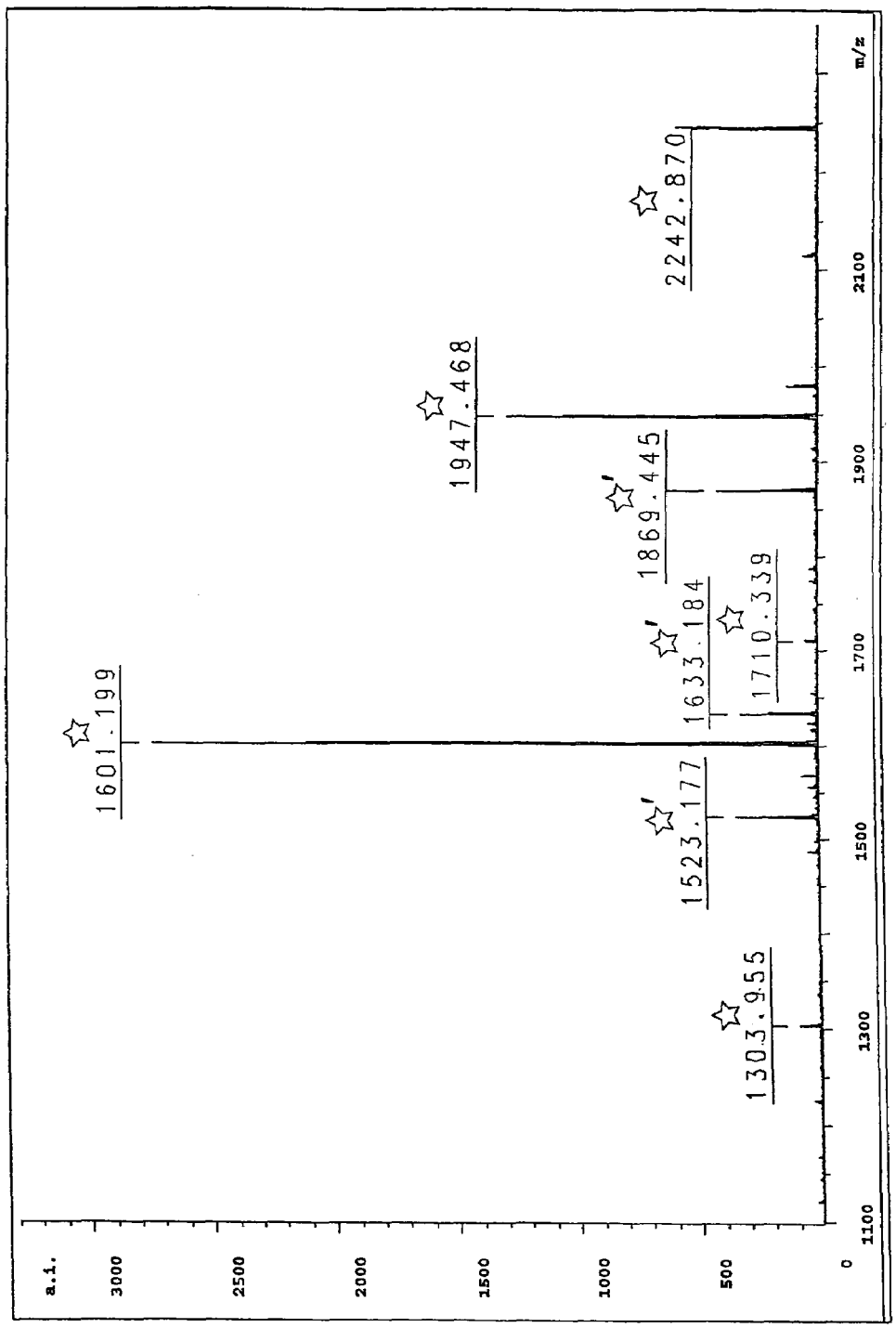
FIGURE 3: MALDI-TOF mass spectrum of a phosphotyrosine peptide mix after purification with P-Tyr-100 monoclonal antibody.

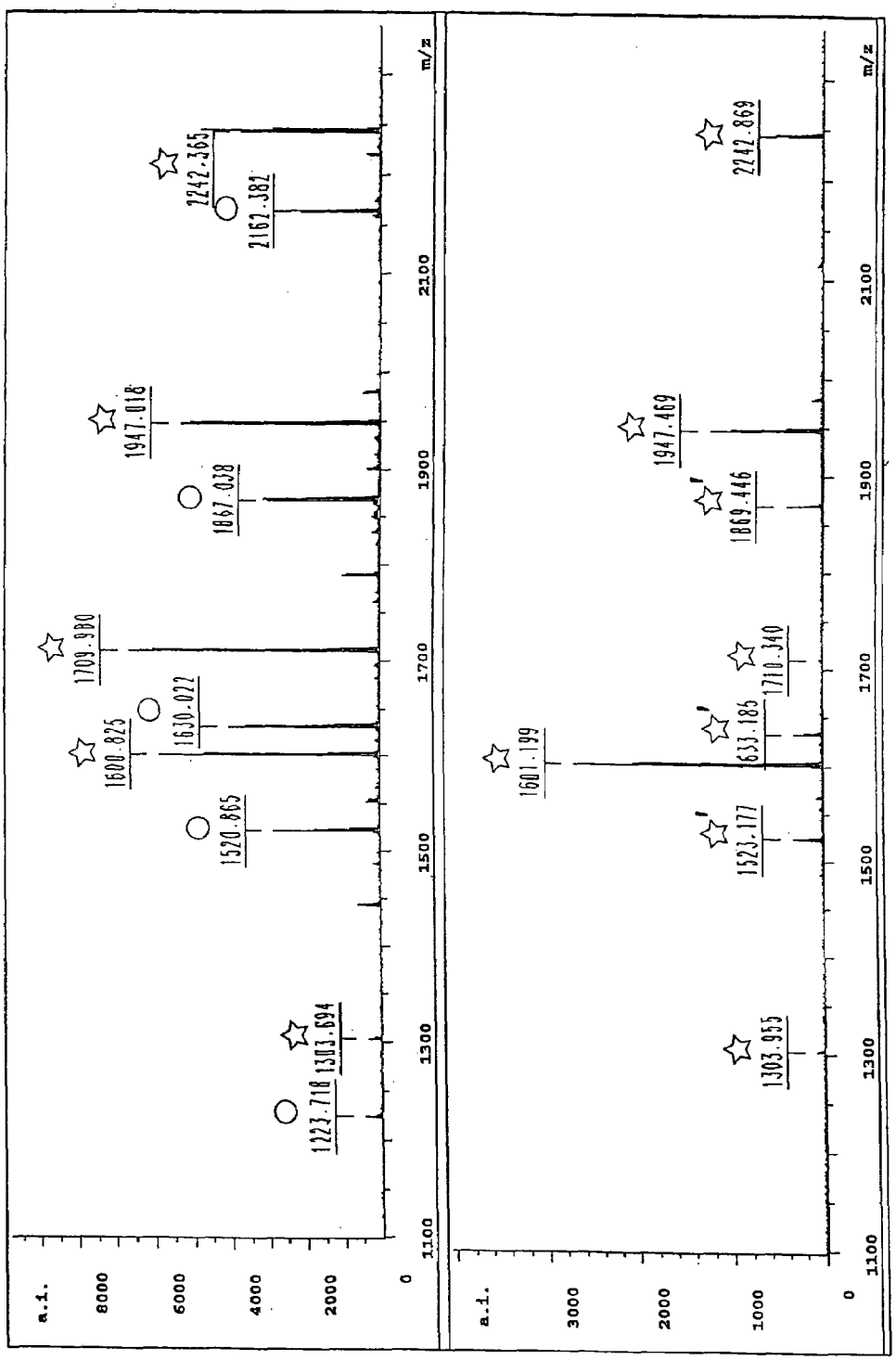
FIGURE 4: MALDI-TOF mass spectra of a phosphotyrosine peptide mix before and after purification with P-Tyr-100 monoclonal antibody.

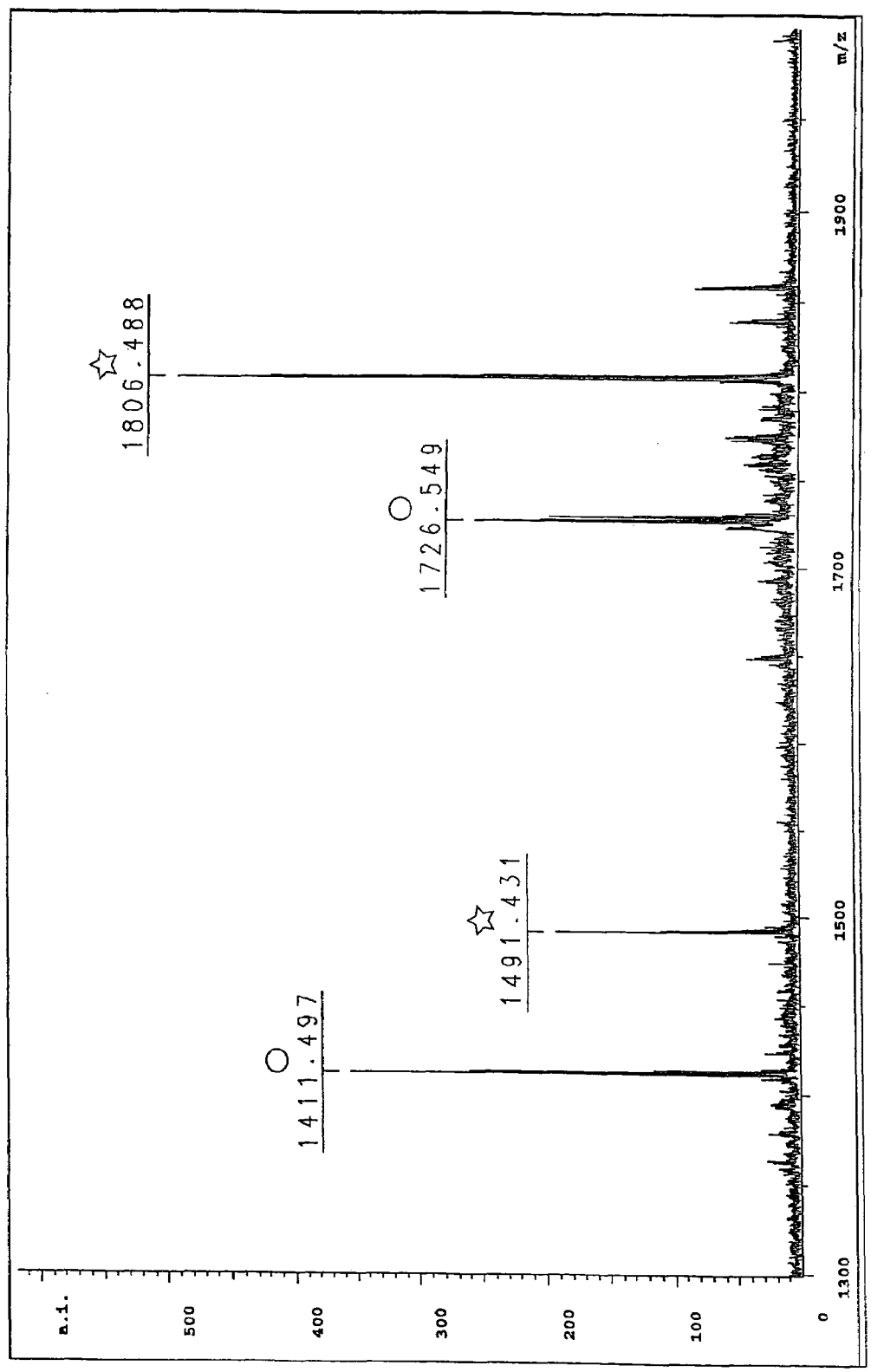
FIGURE 5: MALDI-TOF mass spectrum of an unpurified phosphothreonine peptide mix.

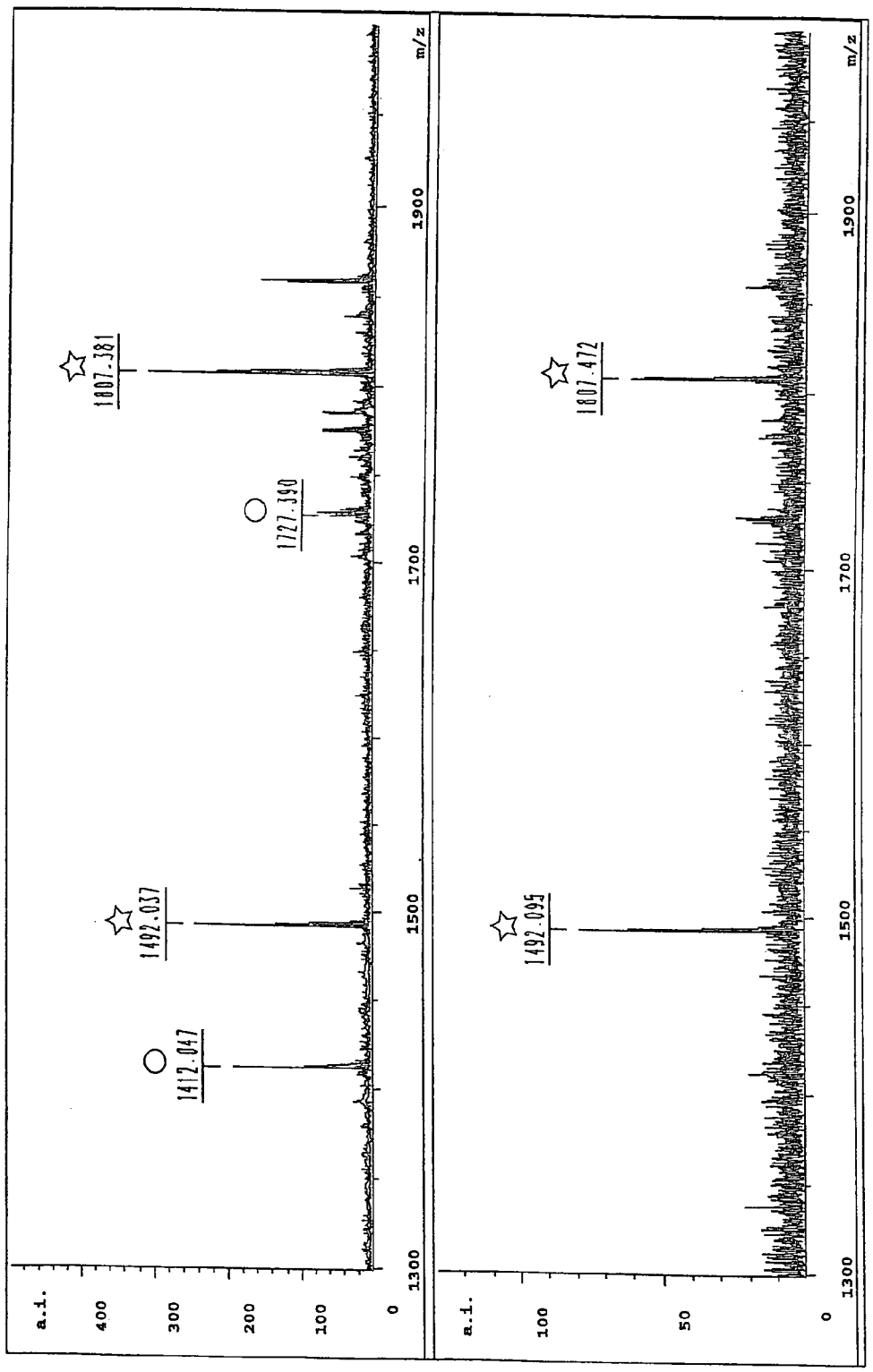
FIGURE 6: MALDI-TOF mass spectra of a phosphothreonine peptide mix after purification with P-Thr polyclonal antibody, showing the unbound peptide fraction and the bound and eluted peptide fraction.

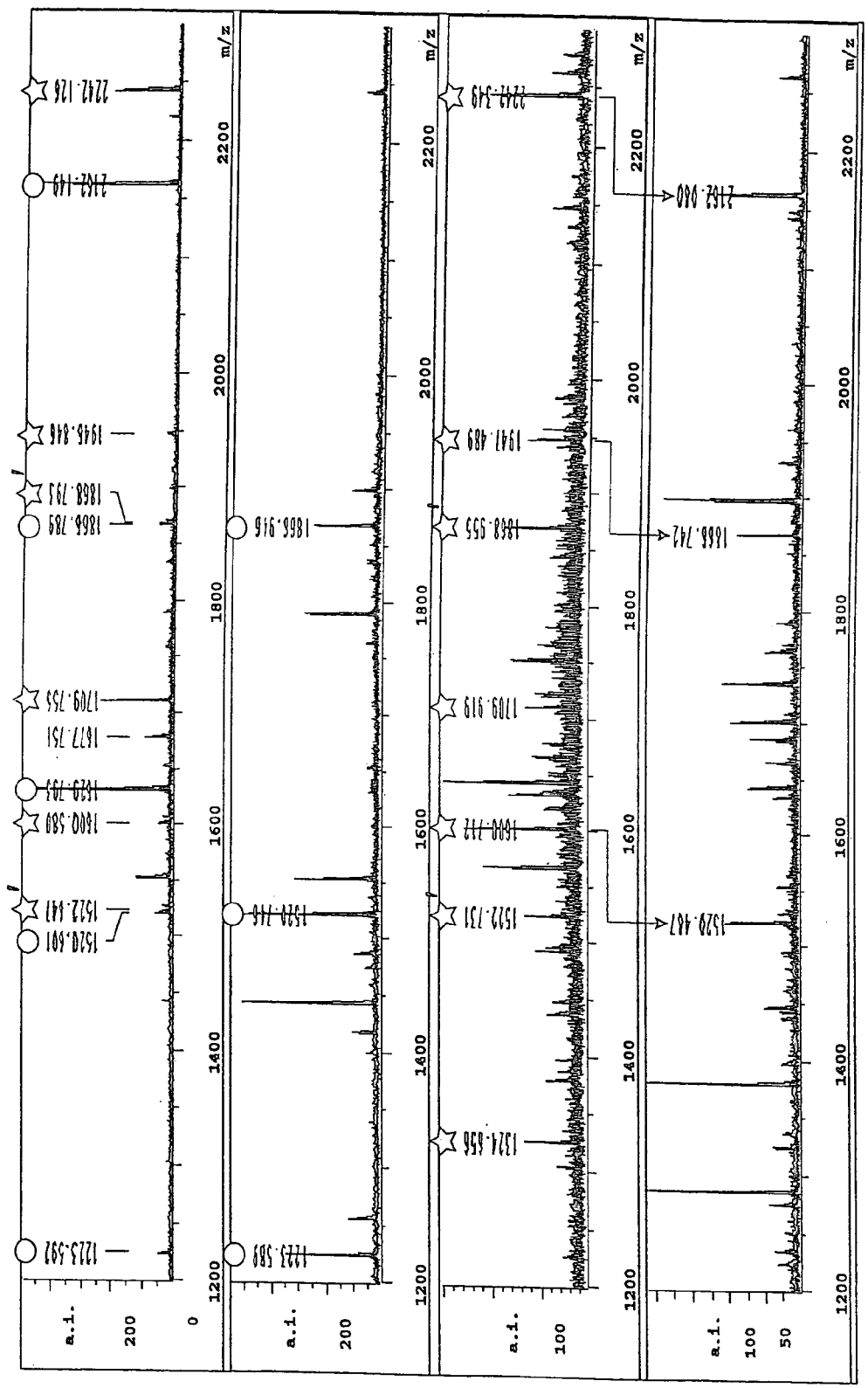
FIGURE 7: MALDI-TOF mass spectra of a phosphotyrosine peptide mix before (panel 1) and after (panels 2-4) purification at low levels (<1 pmol) with P-Tyr-100 monoclonal antibody.

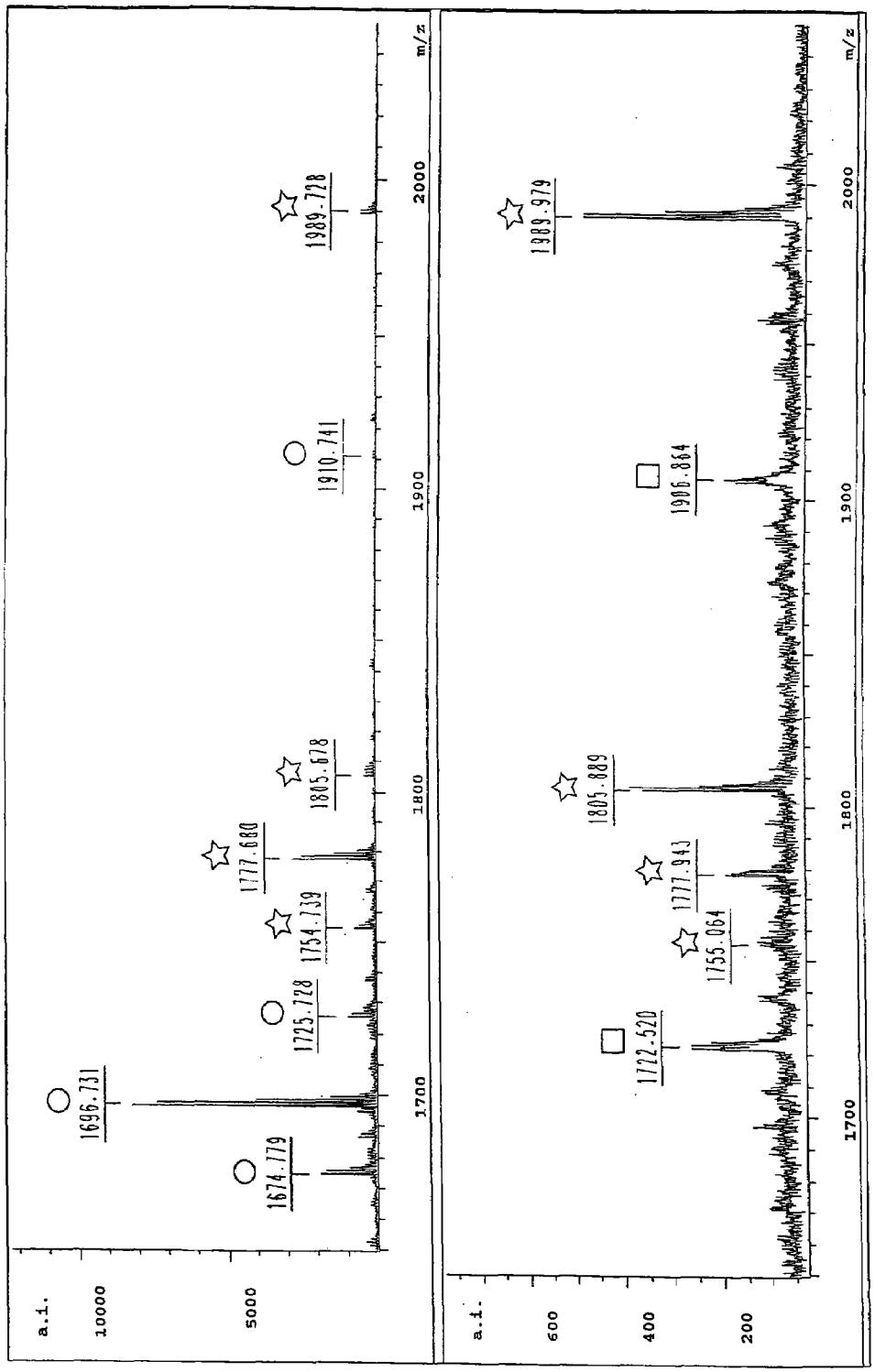
FIGURE 8: MALDI-TOF mass spectra of a phospho-Akt substrate peptide mix before and after purification with phospho-(Ser/Thr) Akt substrate polyclonal antibody.

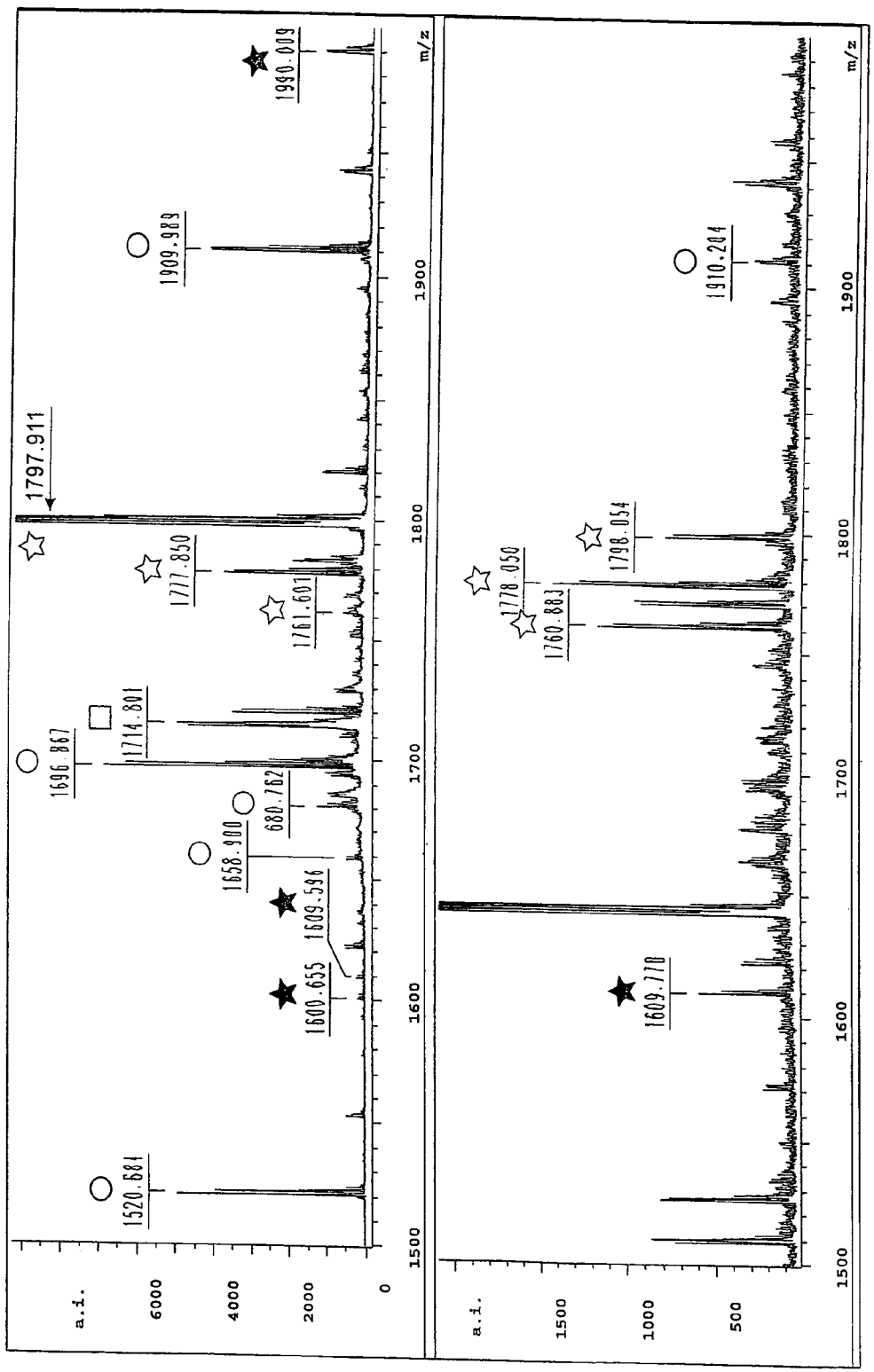
FIGURE 9: MALDI-TOF mass spectra of a 14-3-3 binding motif peptide mix before and after purification with phospho-(Ser) 14-3-3 binding motif monoclonal antibody.

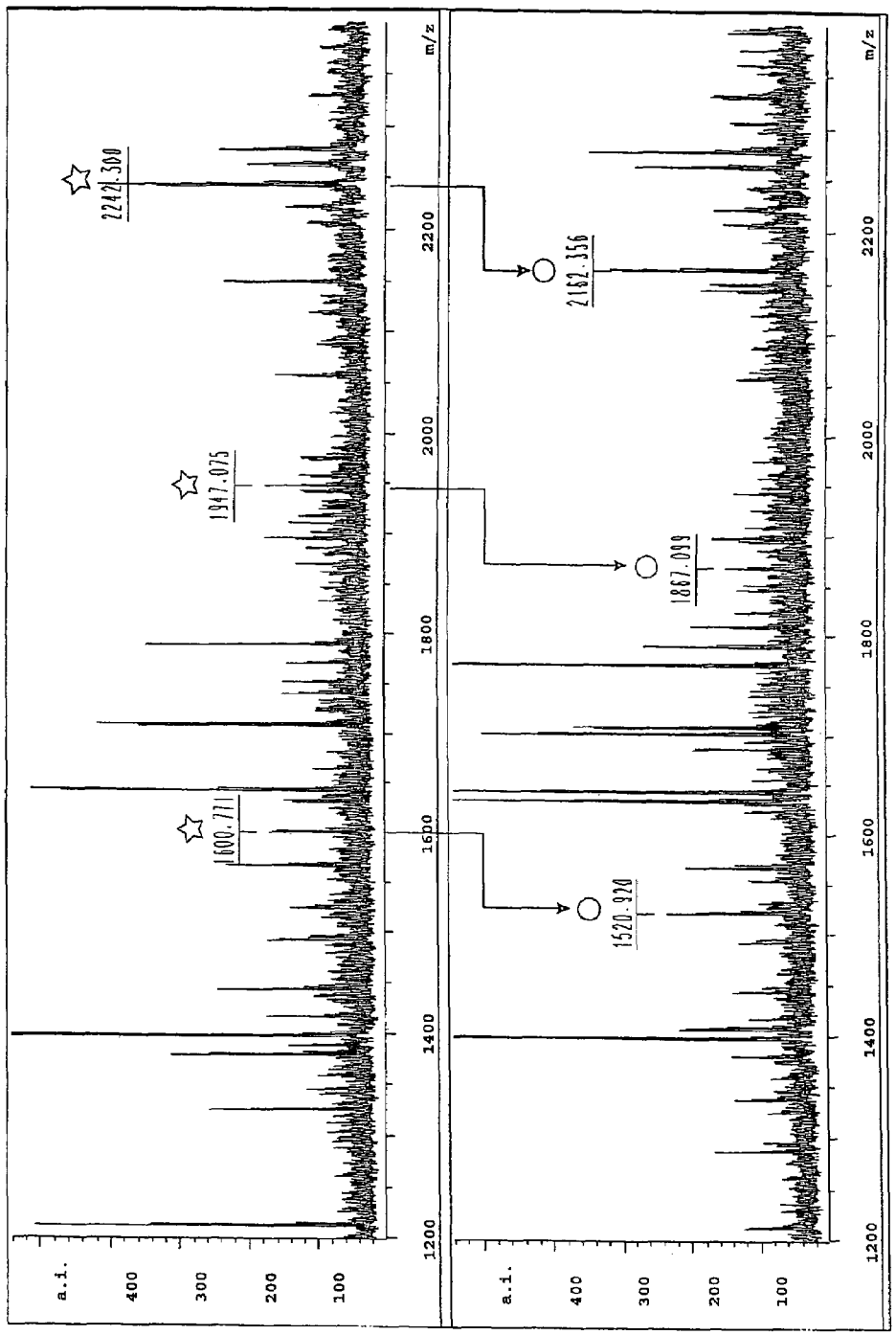
FIGURE 10: MALDI-TOF mass spectra of the bound and eluted peptide fraction purified from a mixture of digested cell extract, phosphotyrosine peptide mix, and phospho-Akt substrate peptide mix with P-Tyr-100 monoclonal antibody, before and after phosphatase treatment.

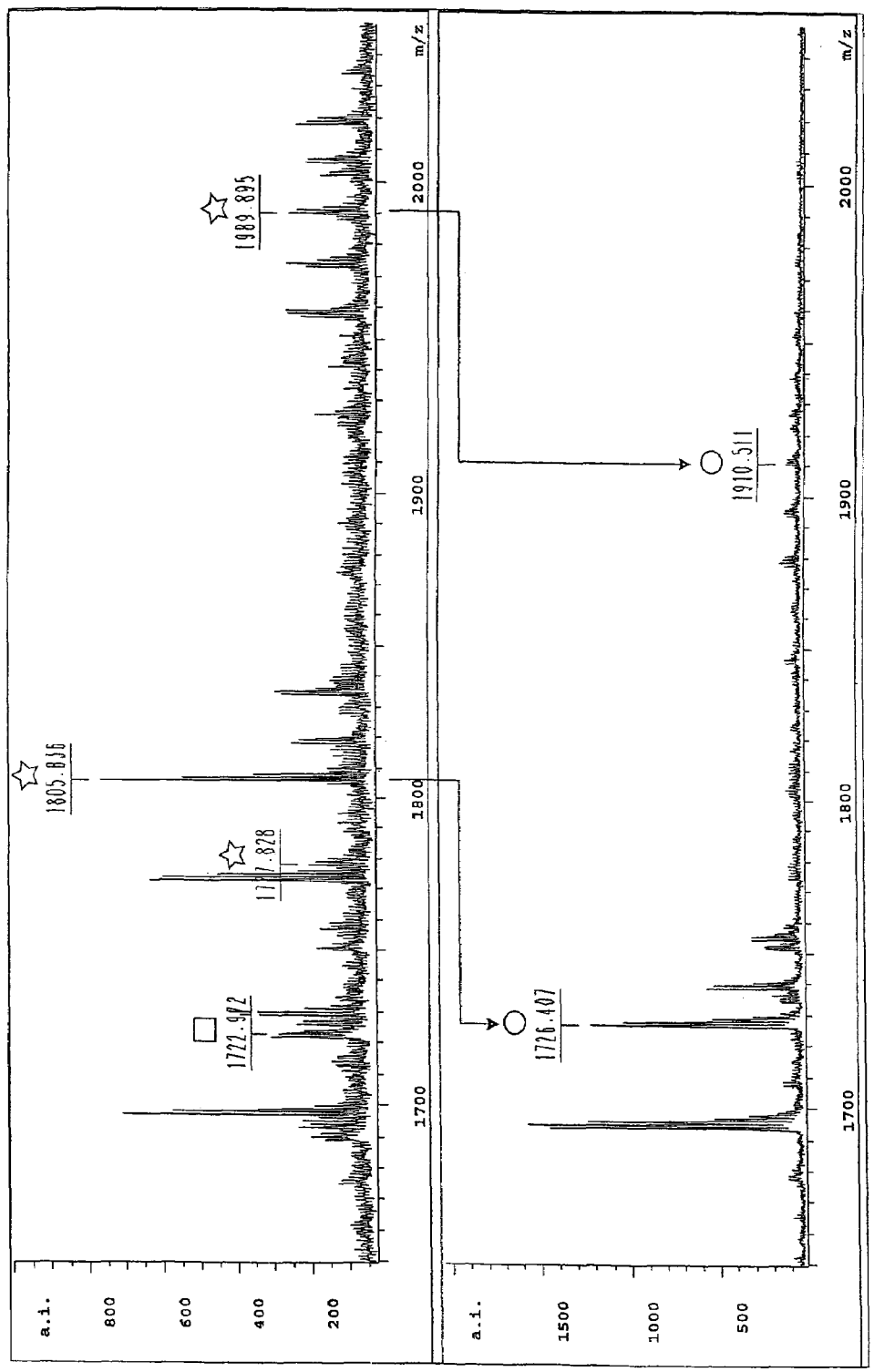
FIGURE 11: MALDI-TOF mass spectra of the bound and eluted peptide fraction purified from a mixture of digested cell extract, phosphotyrosine peptide mix, and phospho-Akt substrate peptide mix with phospho-(Ser/Thr) Akt substrate polyclonal antibody, before and after phosphatase treatment.

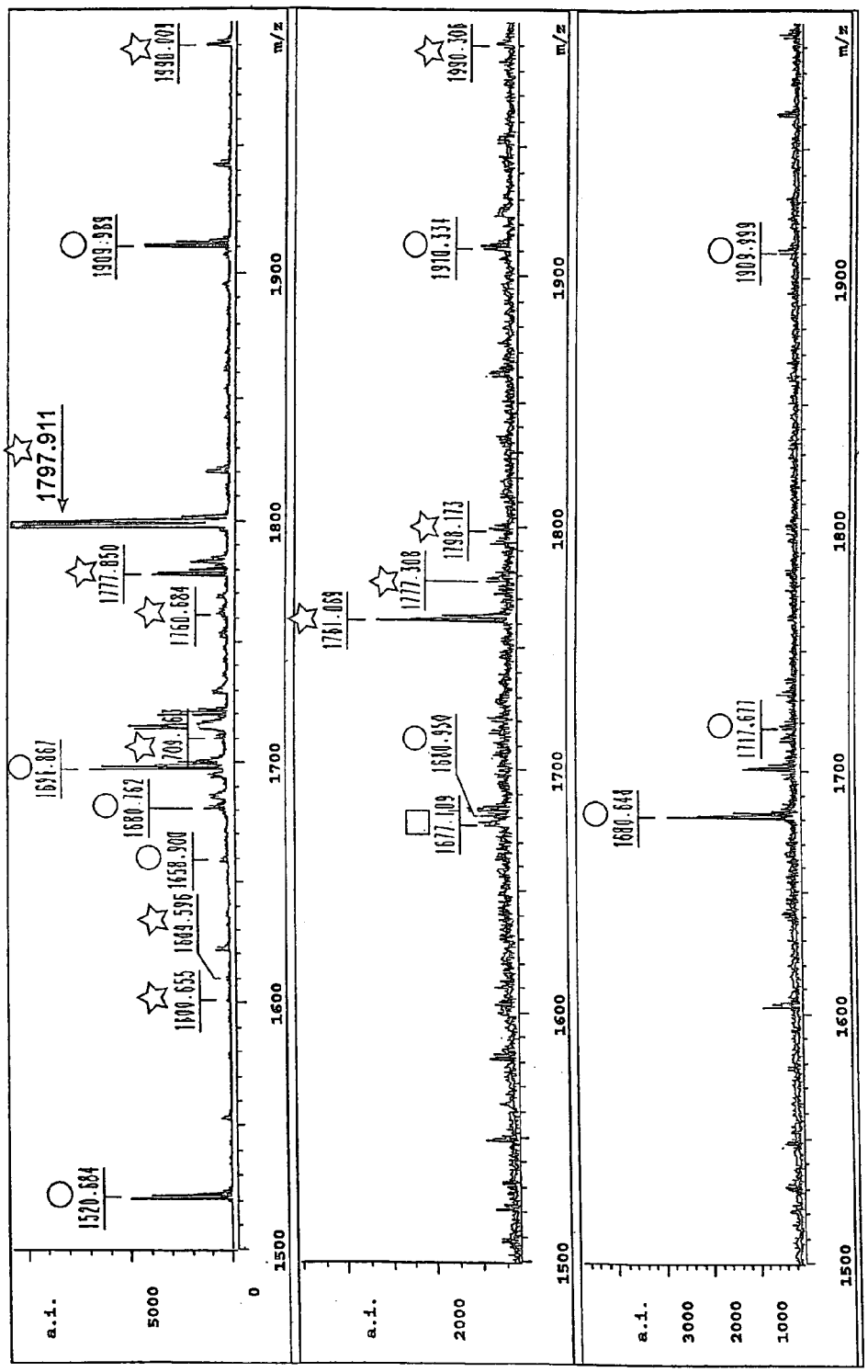
FIGURE 12: MALDI-TOF mass spectrum of the bound and eluted peptide fraction purified from a mixture of digested cell extract and 14-3-3 binding motif peptide mix with phospho-(Ser) 14-3-3 binding motif monoclonal antibody, before and after phosphatase treatment.

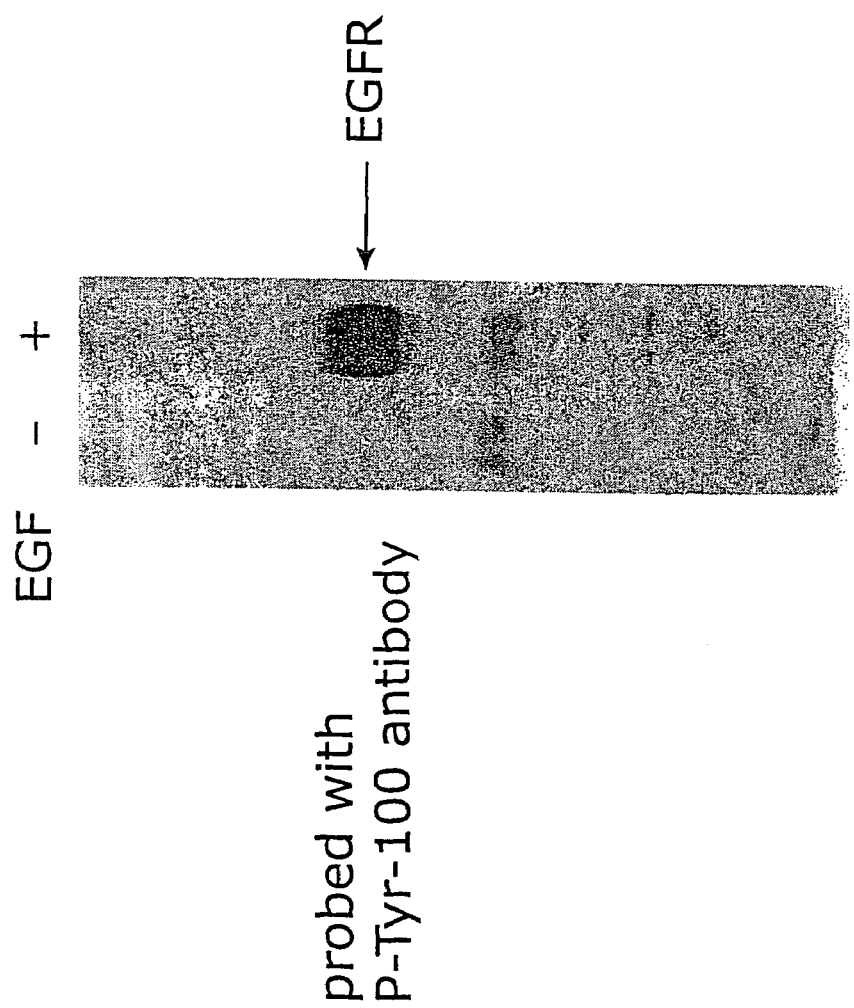
FIGURE 13: Western blot of A431 cells overexpressing the epidermal growth factor receptor (EGFR) and probed with P-Tyr-100 monoclonal antibody.

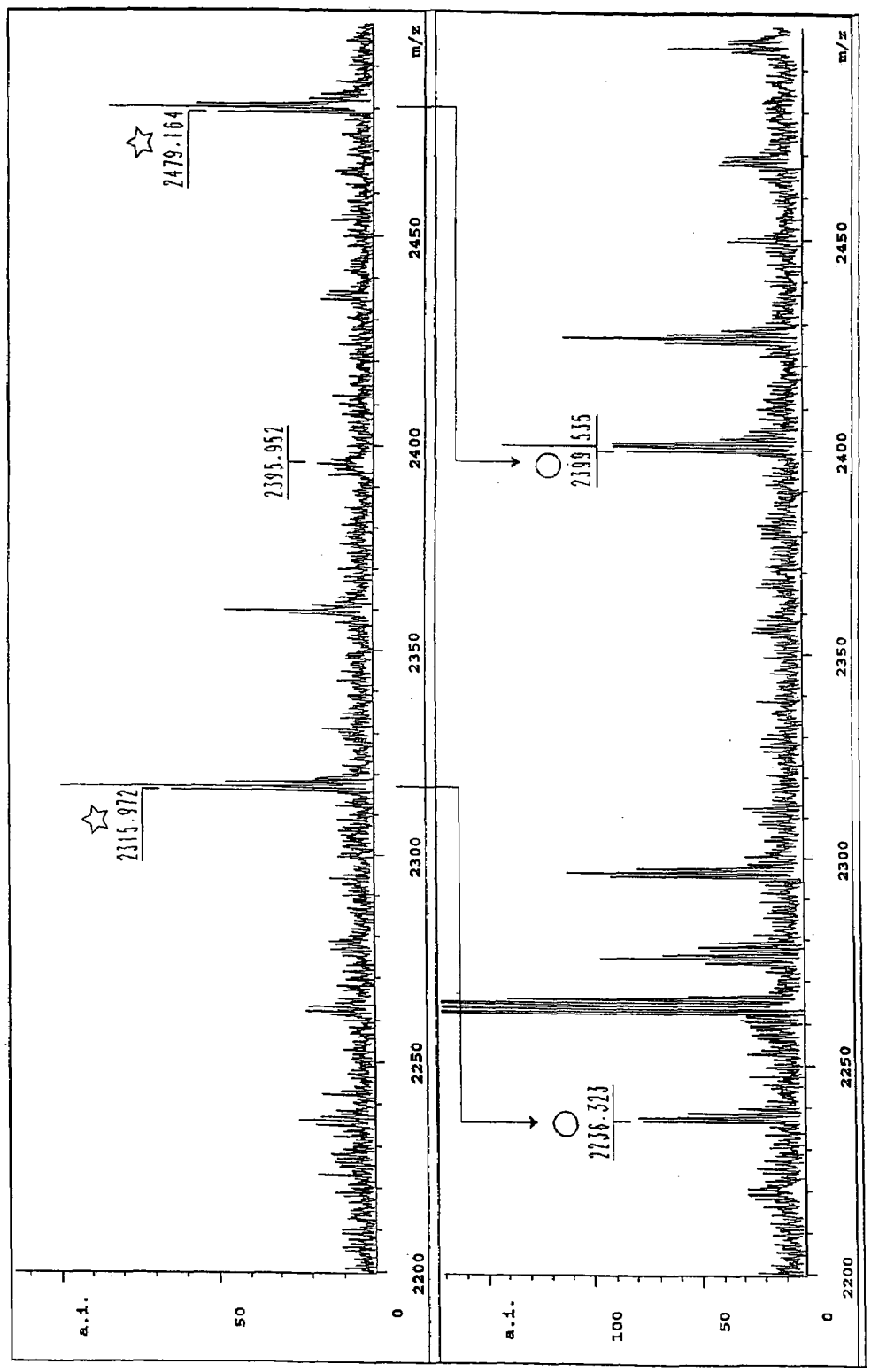
FIGURE 14: MALDI-TOF mass spectra of the bound and eluted peptide fraction purified from a digested extract of A431 cells overexpressing EGFR with P-Tyr-100 monoclonal antibody, before and after phosphatase treatment.

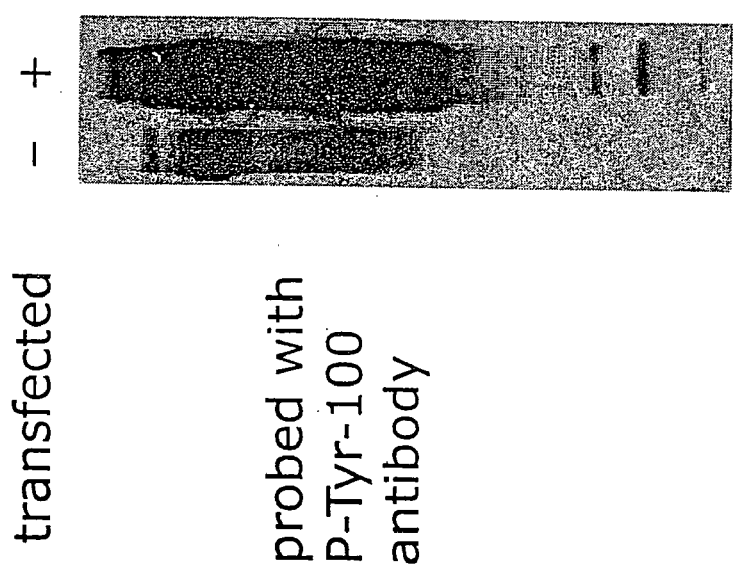
FIGURE 15: Western blot of 3T3 cells transfected to express active Src protein kinase constitutively and probed with P-Tyr-100 monoclonal antibody.

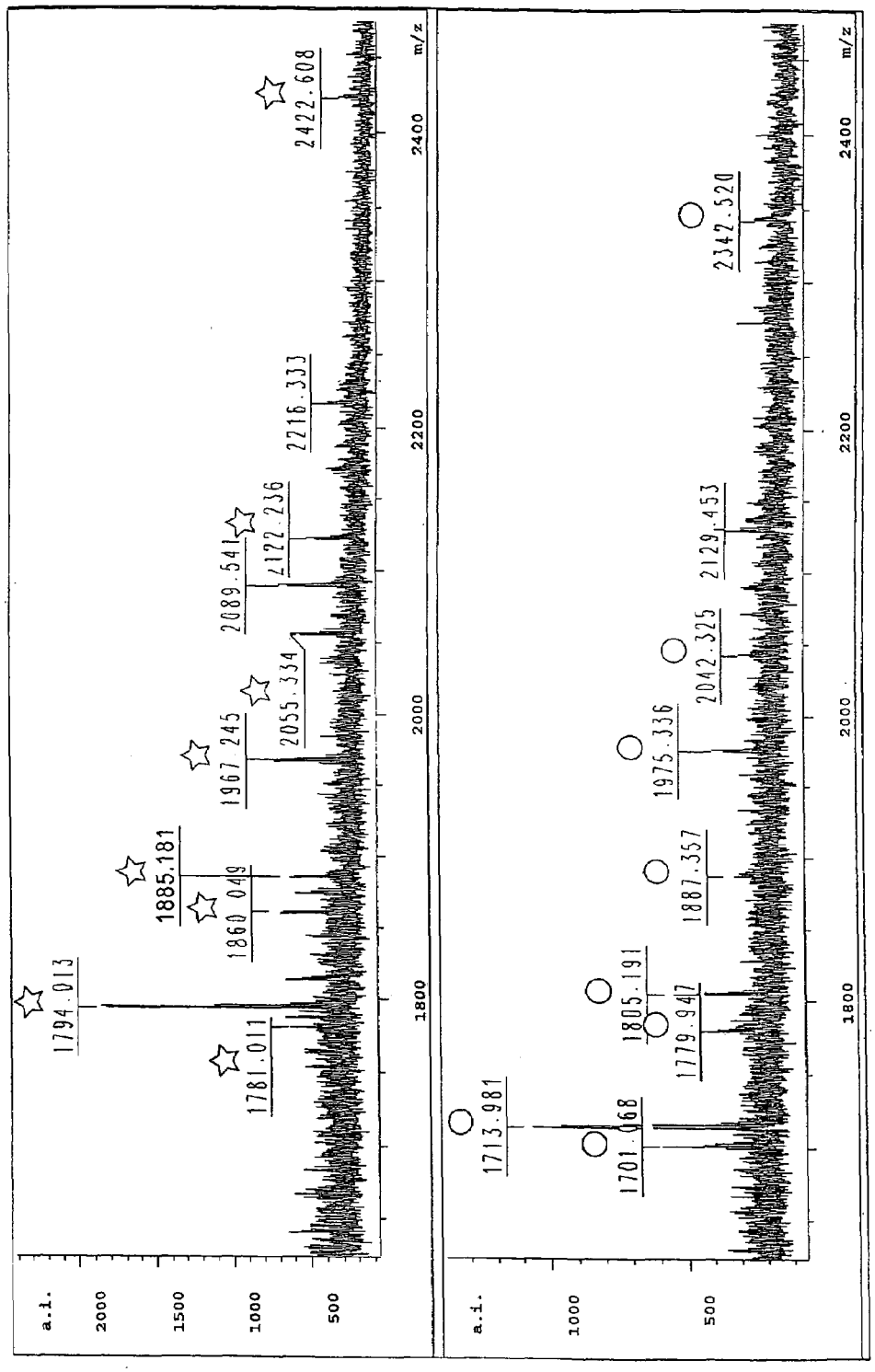
FIGURE 16: MALDI-TOF mass spectra of the bound and eluted peptide fraction purified from a digested extract of 3T3 cells transfected to express active Src protein kinase constitutively with P-Tyr-100 monoclonal antibody, before and after phosphatase treatment.

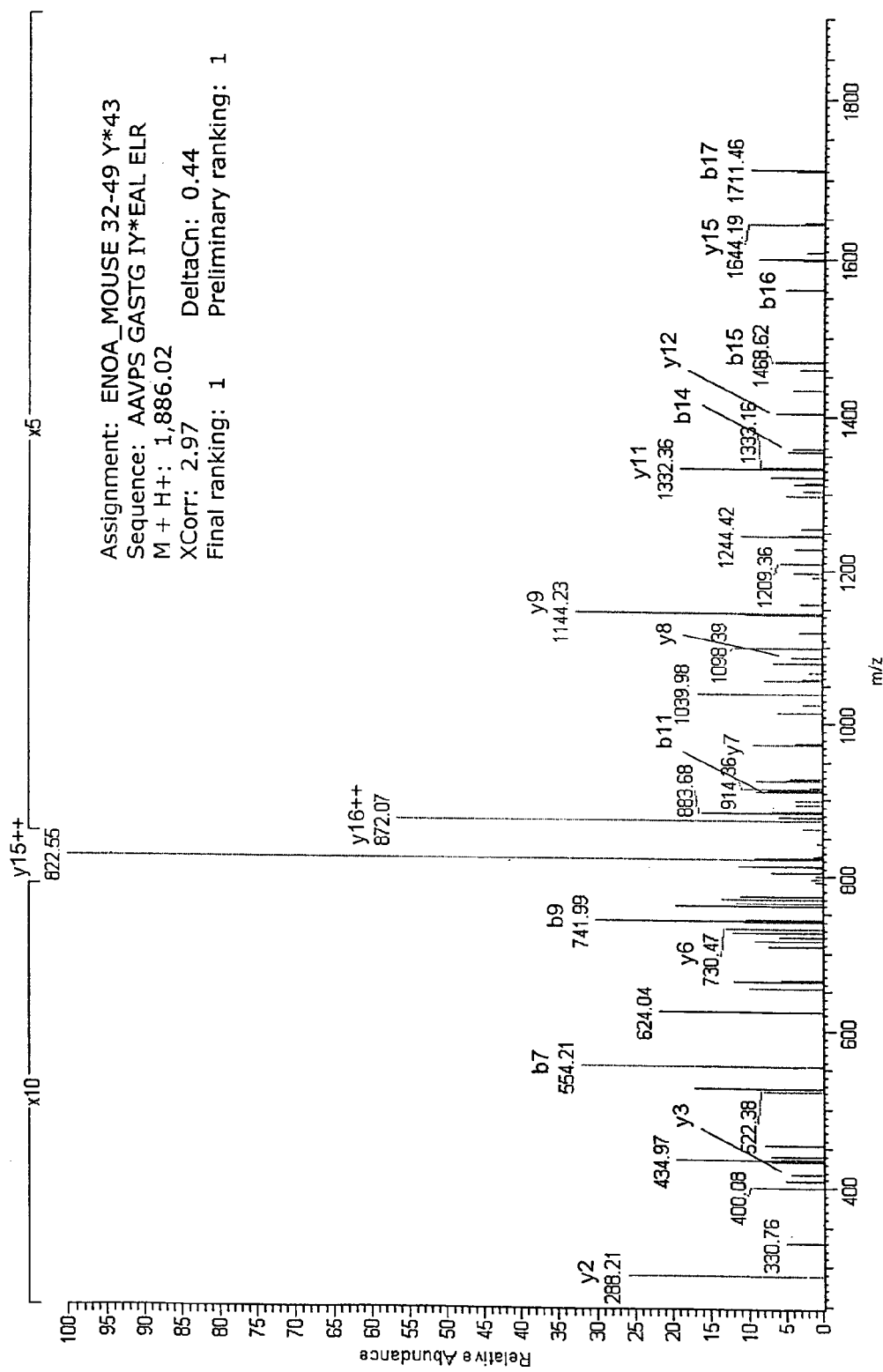
FIGURE 17: LC-MS/MS spectrum of one of the modified peptides purified from an extract of 3T3 cells transfected with Src protein kinase with immobilized P-Tyr-100 antibody.

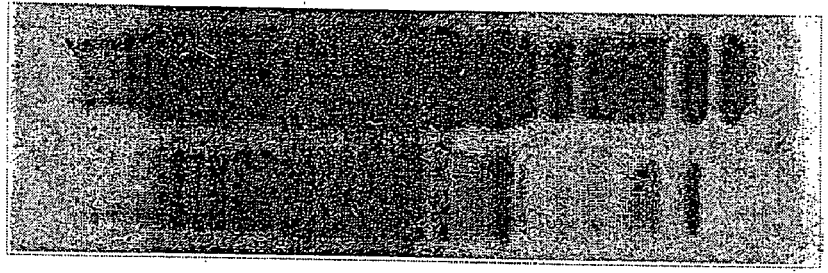
FIGURE 18: Western blot of Jurkat cells treated with TPA and probed with phospho-(Ser) PKC substrate antibody.

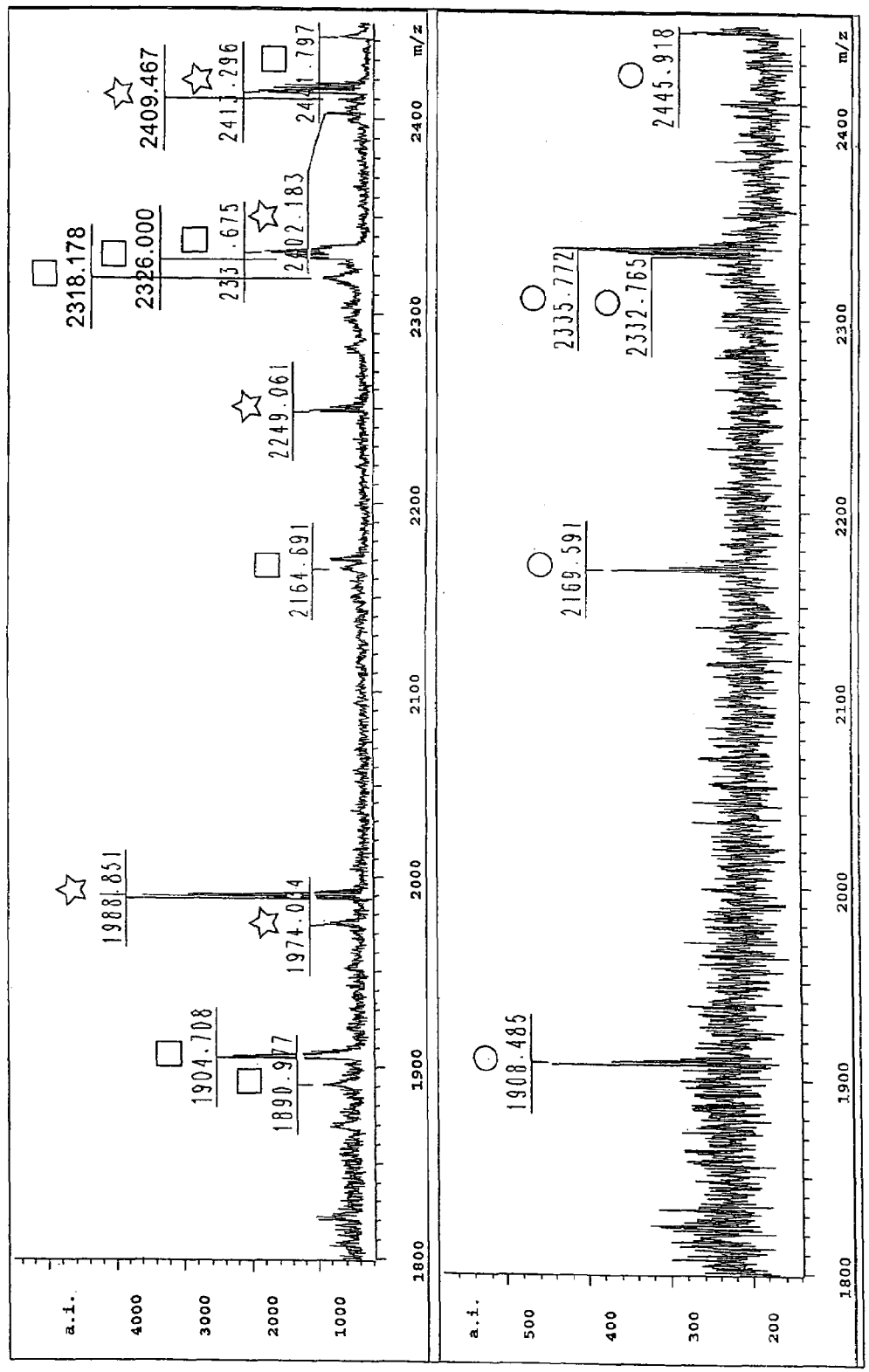
FIGURE 19, PANEL A: MALDI-TOF mass spectrum of modified peptides isolated from a TPA-treated Jurkat cell extract with immobilized phospho-PKC substrate antibody, before and after phosphatase treatment.

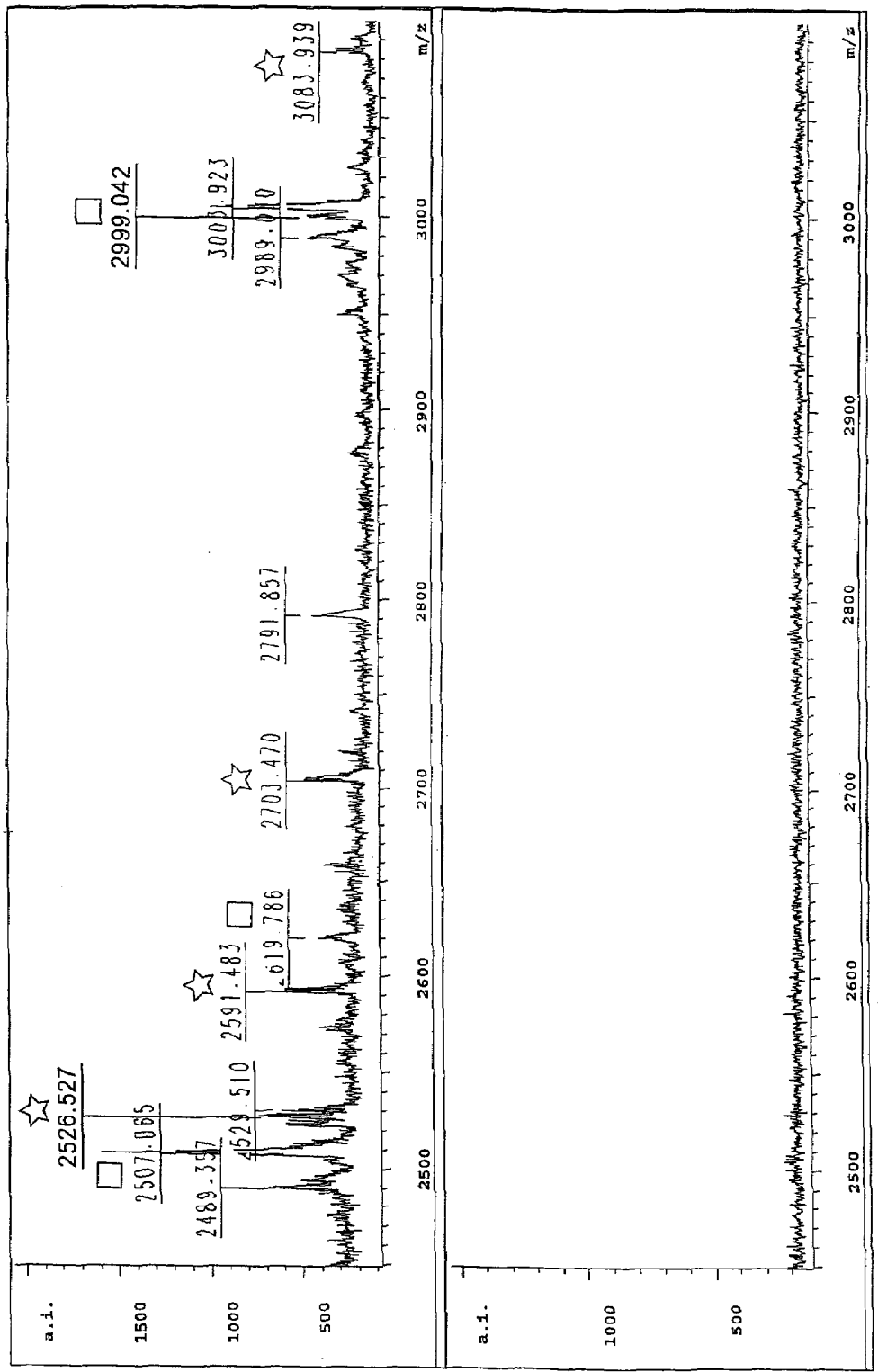
FIGURE 19, PANEL B: MALDI-TOF mass spectrum of modified peptides isolated from a TPA-treated Jurkat cell extract with immobilized phospho-PKC substrate antibody, before and after phosphatase treatment.

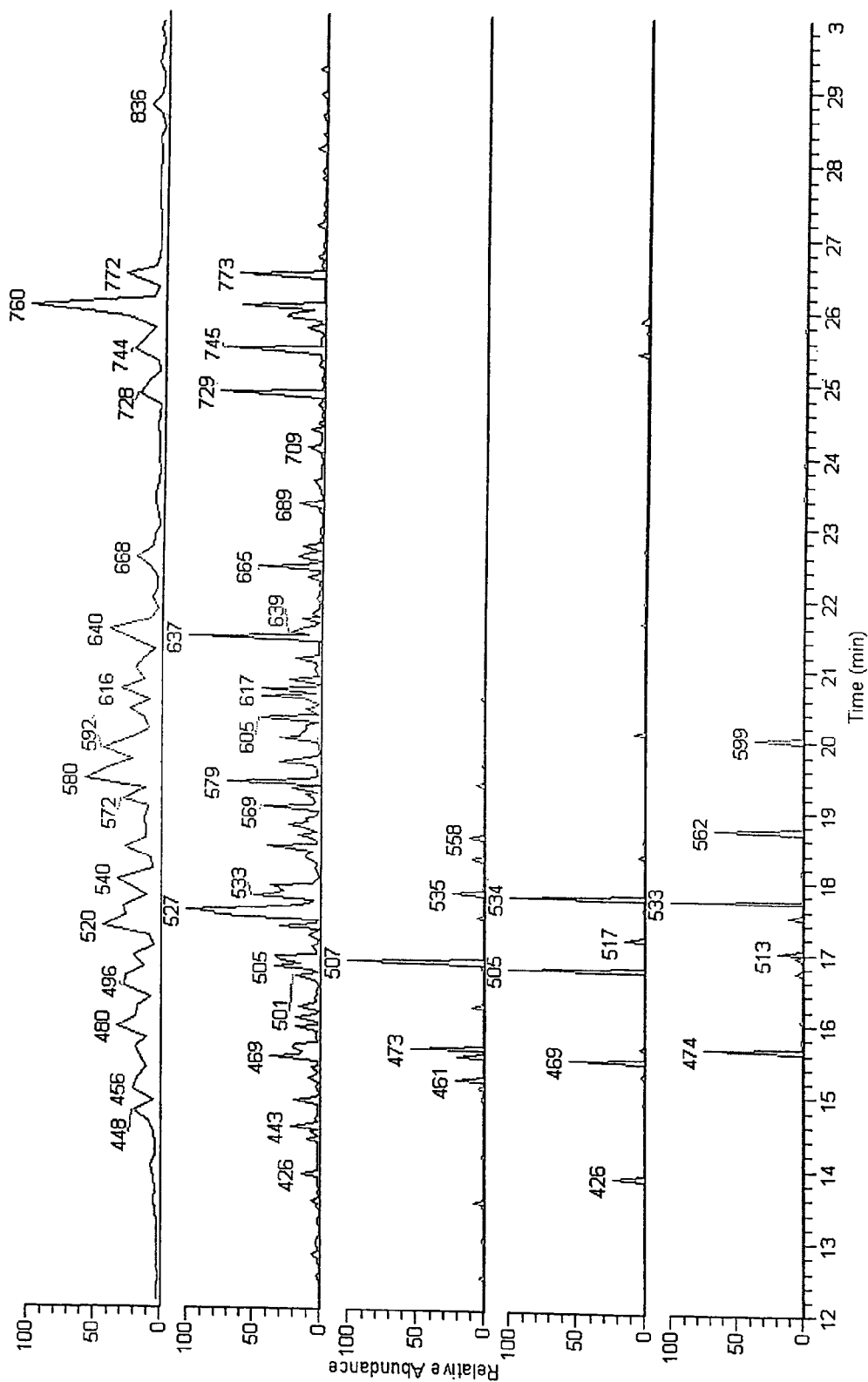
FIGURE 20: Various chromatograms obtained by LC-MS/MS analysis of the modified peptides isolated from a TPA-treated Jurkat cell extract using immobilized phospho-PKC substrate antibody.

| LC-MS/MS Spectrum No. | m/z | z | m | Number of Phosphates | Seen by MALDI | Label in MALDI | Identified by MS³ as protein residues site |
|---|---|---|---|---|---|---|---|
| 579 | 583.770 | 2 | 1,165.526 | 1 | ~ | | |
| 417 | 668.300 | 2 | 1,334.586 | 1 | ~ | | UFD1 333-343 S*335 |
| 426 | 446.030 | 3 | 1,335.069 | 1 | ~ | | as above |
| 461 | 953.620 | 2 | 1,905.226 | 1 | ~ | | |
| 470 | 995.100 | 2 | 1,988.186 | 1 | + | 1,988.851 | |
| 469 | 664.000 | 3 | 1,988.979 | 1 | + | as above | |
| 473 | 1,205.480 | 2 | 2,408.946 | 1 | + | 2,409.467 | PTN6 576-595 S*588 |
| 474 | 603.640 | 4 | 2,410.532 | 1 | + | as above | as above |
| 535 | 1,207.650 | 2 | 2,413.286 | 1 | + | 2,413.296 | UFD1 322-343 S*335 |
| 534 | 805.310 | 3 | 2,412.909 | 1 | + | as above | as above |
| 533 | 604.440 | 4 | 2,413.732 | 1 | + | as above | as above |
| 558 | 1,209.750 | 2 | 2,417.486 | 1 | ~ | | |
| 507 | 1,297.140 | 2 | 2,592.266 | 1 | + | 2,591.483 | |
| 505 | 865.040 | 3 | 2,592.099 | 1 | + | as above | |
| 513 | 807.900 | 4 | 3,227.572 | 1 | - | | |
| 599 | 824.250 | 4 | 3,292.972 | 1 | ~ | | |
| 601 | 1,099.170 | 3 | 3,294.489 | 1 | ~ | | |
| 562 | 1,018.680 | 4 | 4,070.692 | 1 | - | | |

For "Seen in MALDI", + indicates yes, ~ possibly (obscured or sometimes seen), - no. Note masses above 3,600 were not measured during MALDI-TOF mass spectrometry.

FIGURE 21: Properties of the peptides that were observed to undergo neutral-loss during the LC-MS/MS analysis shown in Figure 20.

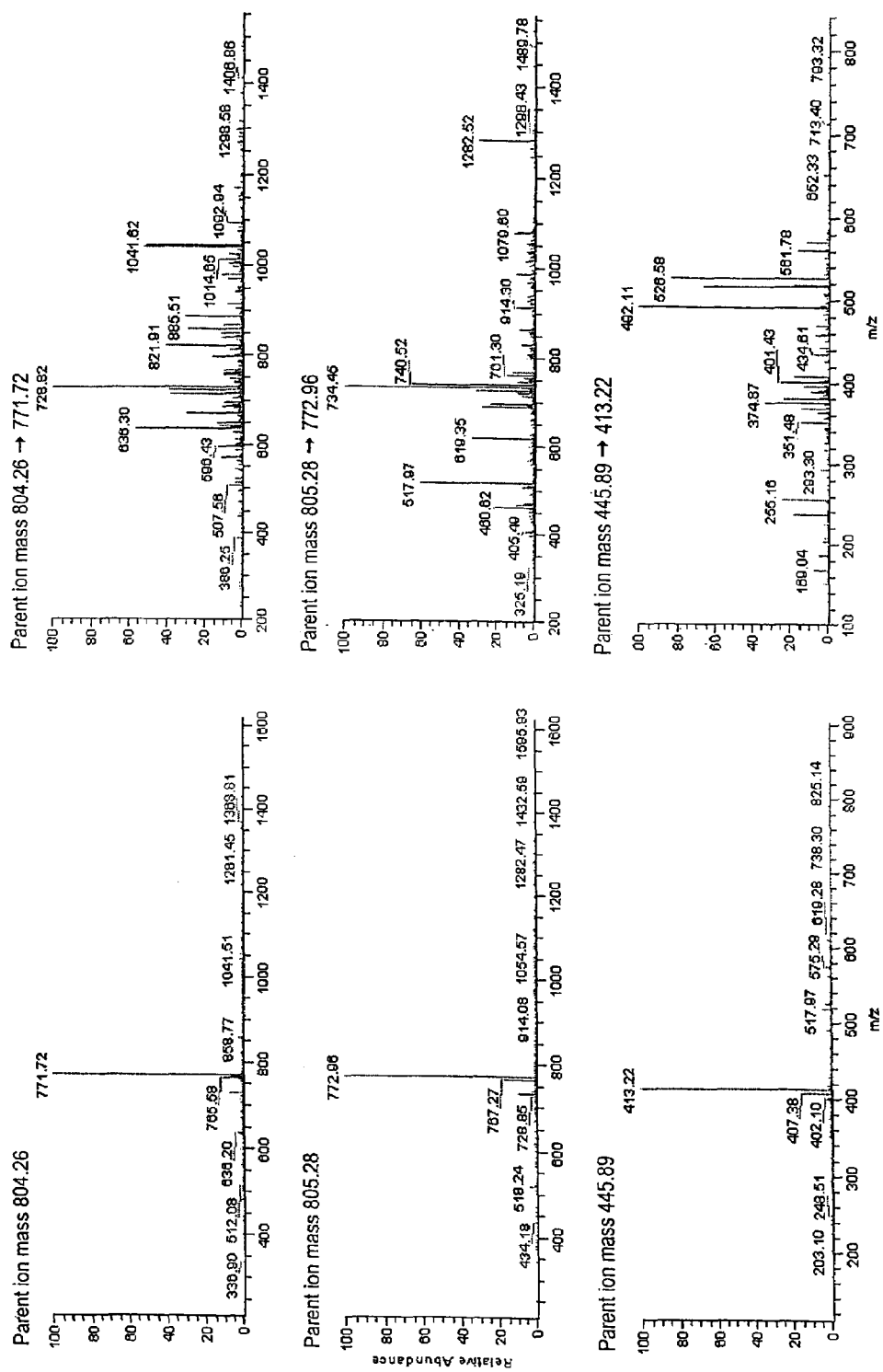
FIGURE 22: Some of the MS/MS spectra (left panels) and MS3 spectra (right panels) acquired during LC-MS3 analysis of the modified peptides purified from a TPA-treated Jurkat cell extract with immobilized phospho-PKC substrate antibody.

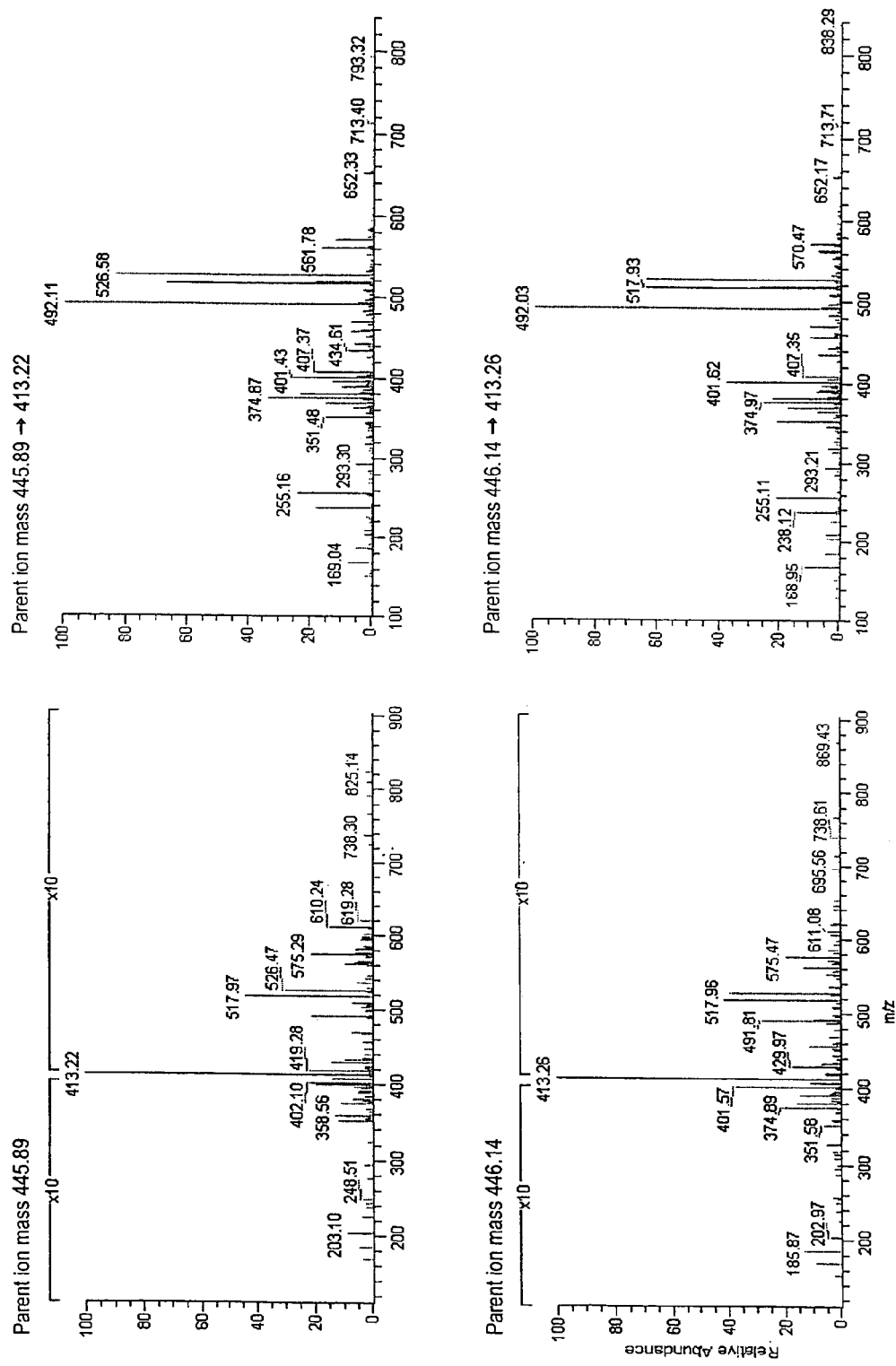
FIGURE 23: MS/MS spectra (left panels) and MS3 spectra (right panels) that confirm an assignment made by Sequest.

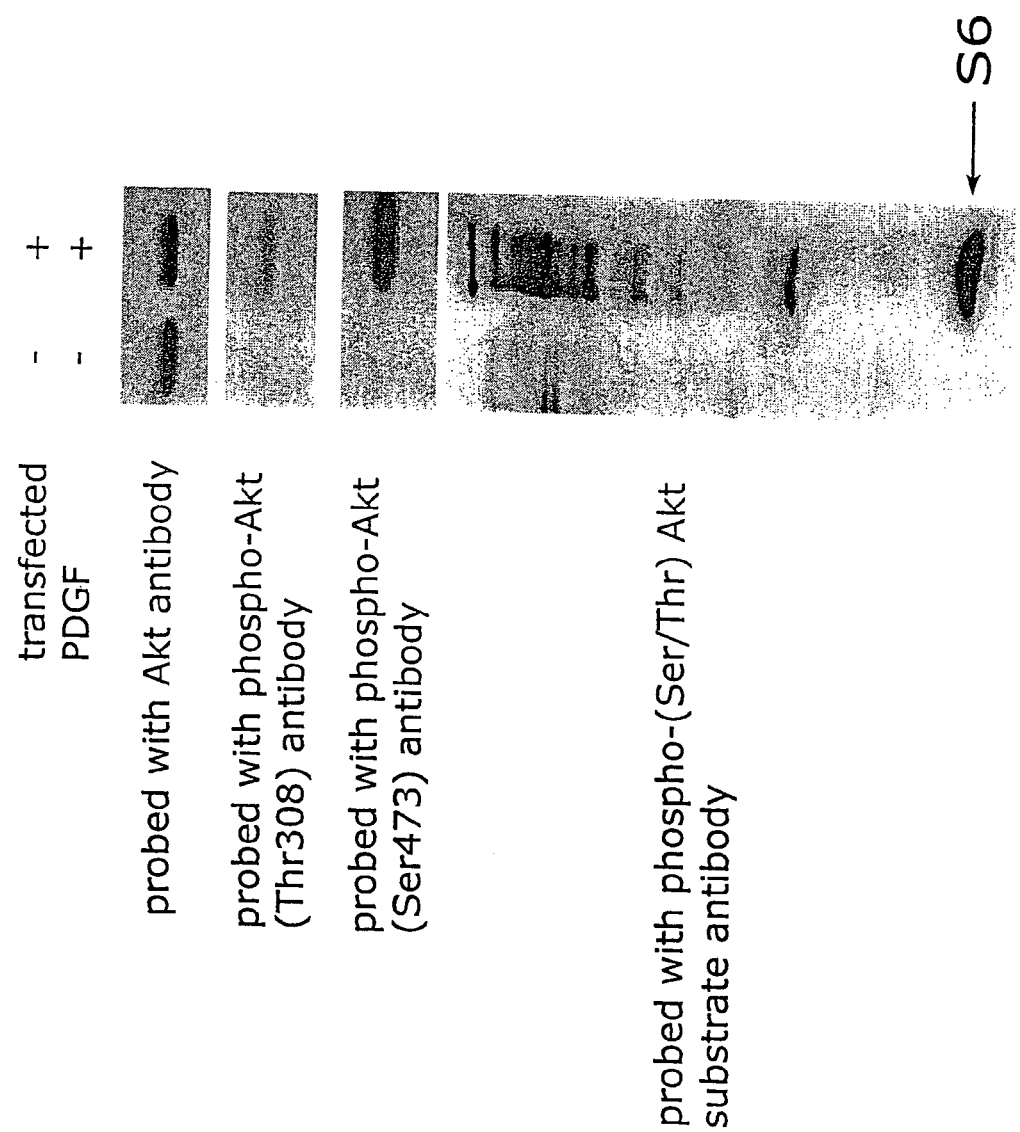
FIGURE 24: Western blot of 3T3 cells transfected to express active Akt protein kinase constituitively and probed with various Akt antibodies or with phospho-(Ser/Thr) Akt substrate polyclonal antibody.

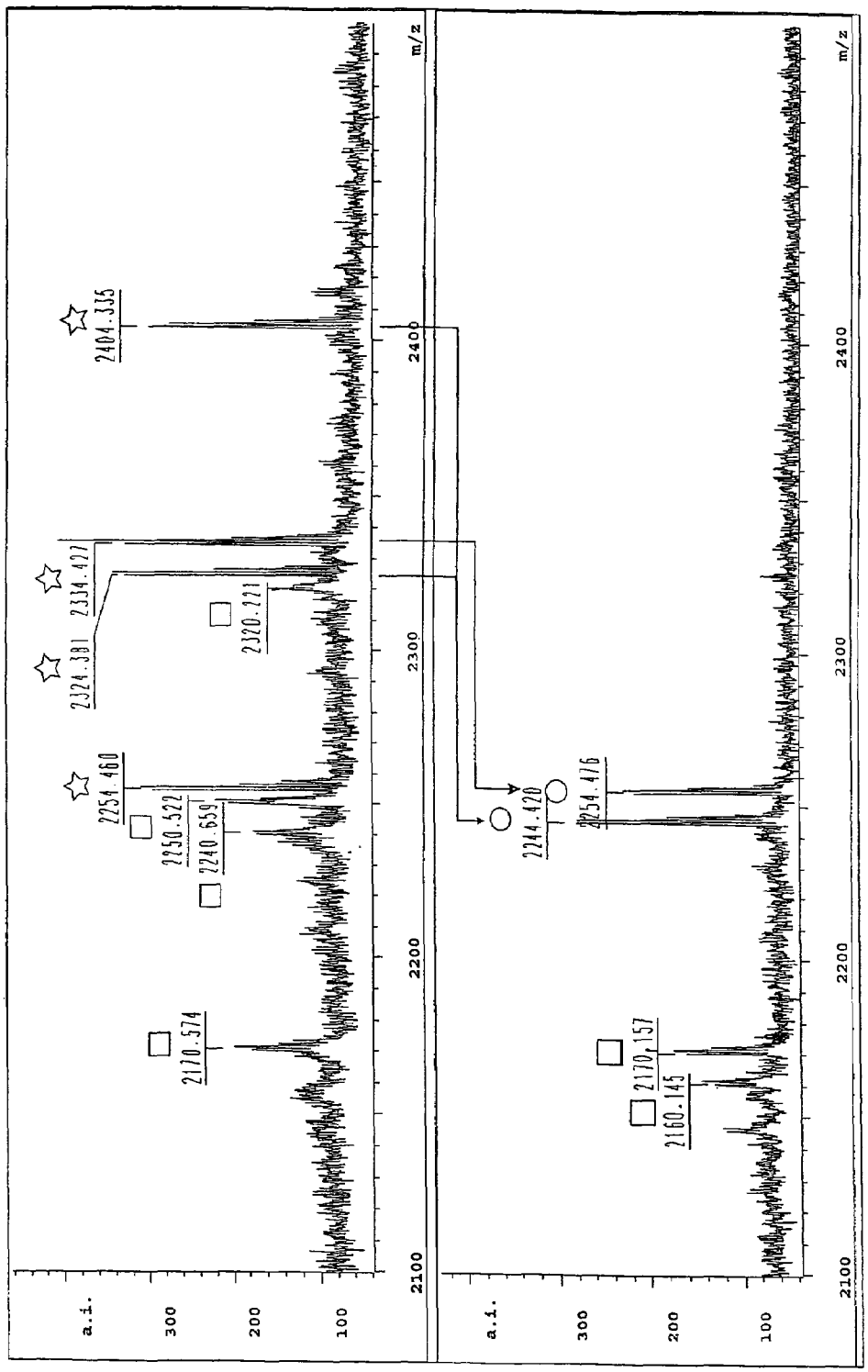
FIGURE 25: MALDI-TOF mass spectra of the bound and eluted peptide fraction purified from a digested extract of 3T3 cells transfected to express active Akt protein kinase constitutively with phospho-(Ser/Thr) Akt substrate polyclonal antibody, before and after phosphatase treatment.

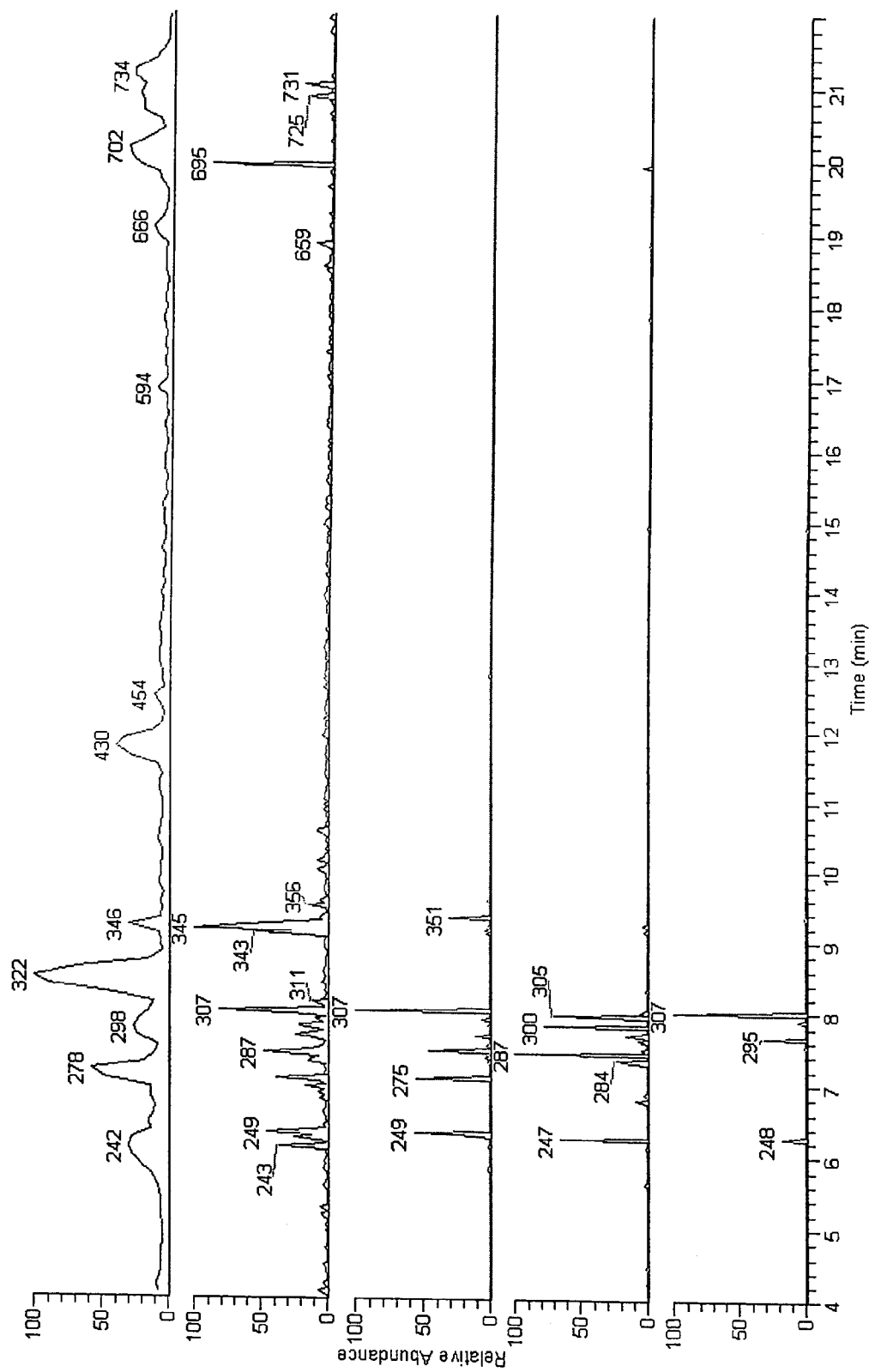
FIGURE 26: Various chromatograms obtained by LC-MS/MS analysis of the modified peptides purified from a PDGF-treated 3T3 cell extract with immobilized phospho-(Ser/Thr) Akt substrate antibody.

| LC-MS/MS Spectrum No. | m/z | z | m | Number of Phosphates | Seen by MALDI | Label in MALDI | Tentative Identification |
|---|---|---|---|---|---|---|---|
| 351 | 925.900 | 2 | 1,849.786 | 1 | + | unlabeled | |
| 300 | 752.510 | 3 | 2,254.509 | 1 | + | 2,254.460 | S6 + 1 PO$_4$ |
| 275 | 1,163.430 | 2 | 2,324.846 | 2 | + | 2,324.381 | peptide A |
| 265 | 775.710 | 3 | 2,324.109 | 2 | + | as above | as above |
| 288 | 1,167.900 | 2 | 2,333.786 | 2 | + | 2,334.427 | S6 + 2 PO$_4$ |
| 287 | 779.230 | 3 | 2,334.669 | 2 | + | as above | as above |
| 295 | 584.760 | 4 | 2,335.012 | 2 | + | as above | as above |
| 249 | 1,203.370 | 2 | 2,404.726 | 3 | + | 2,404.335 | peptide A + 1 PO$_4$ |
| 247 | 802.480 | 3 | 2,404.419 | 3 | + | as above | as above |
| 248 | 602.210 | 4 | 2,404.812 | 2? | + | as above | as above |
| 285 | 1,207.810 | 2 | 2,413.606 | 3 | + | unlabeled | |
| 284 | 806.480 | 3 | 2,416.419 | 3 | + | as above | S6 + 3 PO$_4$ |
| 233 | 1,242.520 | 2 | 2,483.026 | 3 | + | unlabeled | as above |
| 227 | 829.130 | 3 | 2,484.369 | 3 | + | as above | |
| 283 | 949.670 | 3 | 2,845.989 | 2 | + | unlabeled | |
| 305 | 1,068.670 | 3 | 3,202.989 | 2 | | | |
| 307 | 802.330 | 4 | 3,205.292 | 2 | + | unlabeled | |
| 303 | 909.870 | 4 | 3,635.452 | 3? | | | |
| 296 | 1,239.290 | 3 | 3,714.849 | 4? | | | |
| 293 | 1,265.510 | 3 | 3,793.509 | 3 | | | |
| 289 | 1,292.210 | 3 | 3,873.609 | 3 | | | |
| 291 | 981.850 | 4 | 3,923.372 | 2 | | | |

For "Label in MALDI", values indicate masses as labeled in Figure 25.
Note masses above 3,600 were not measured during MALDI-TOF mass spectrometry.

FIGURE 27: Properties of the peptides that were observed to undergo neutral-loss during the LC-MS/MS analysis shown in Figure 26.

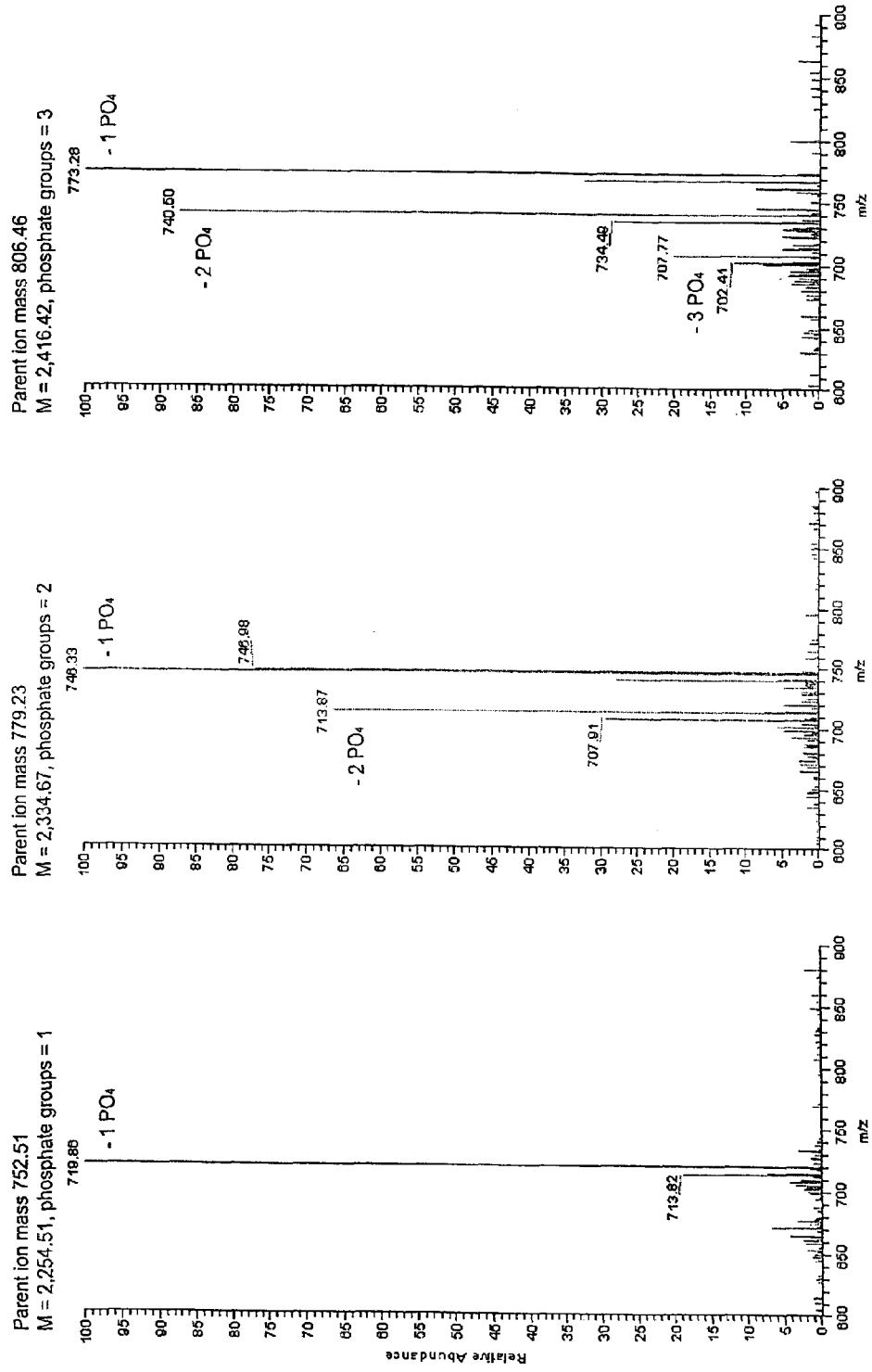
FIGURE 28: Three MS/MS spectra acquired during the LC-MS/MS analysis shown in Figure 26. These three spectra have been tentatively assigned to the multiply phosphorylated peptide from the ribosomal protein S6 with one (panel 1), two (panel 2), or three (panel 3) phosphate groups.

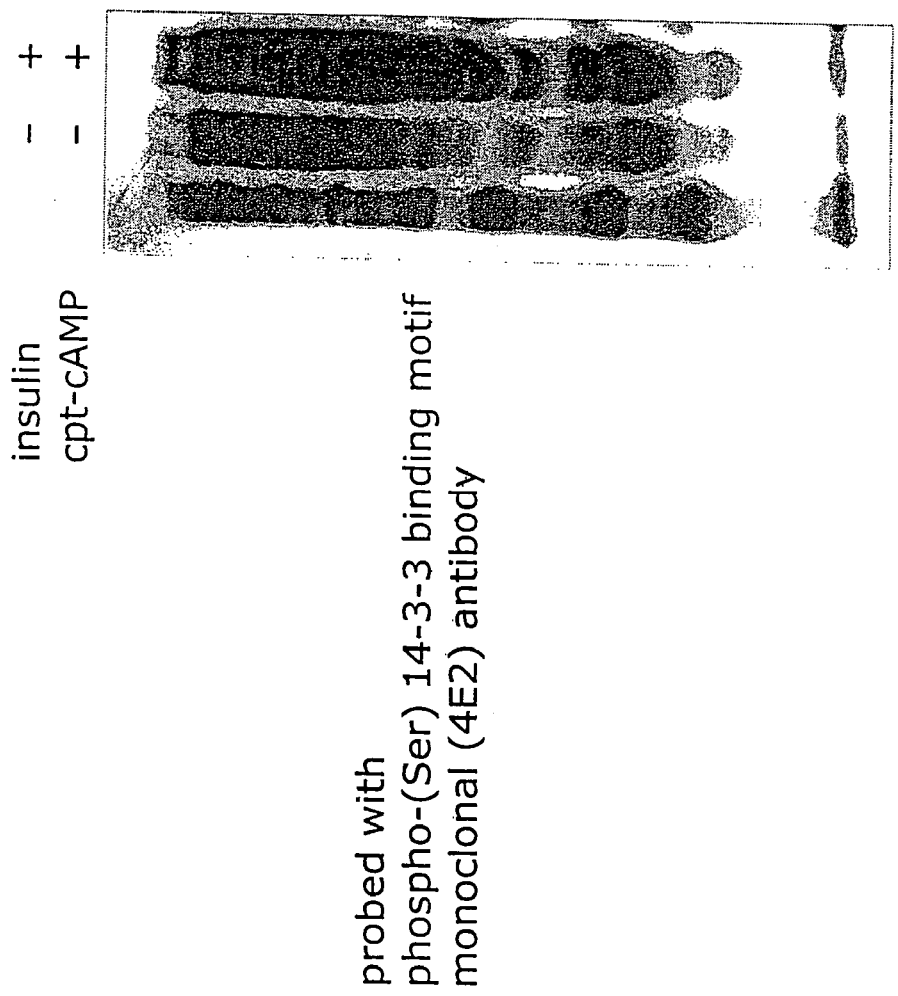
FIGURE 29: Western blot of COS-1 cells treated with insulin and an analog of cAMP and probed with phospho-(Ser) 14-3-3 binding site antibody.

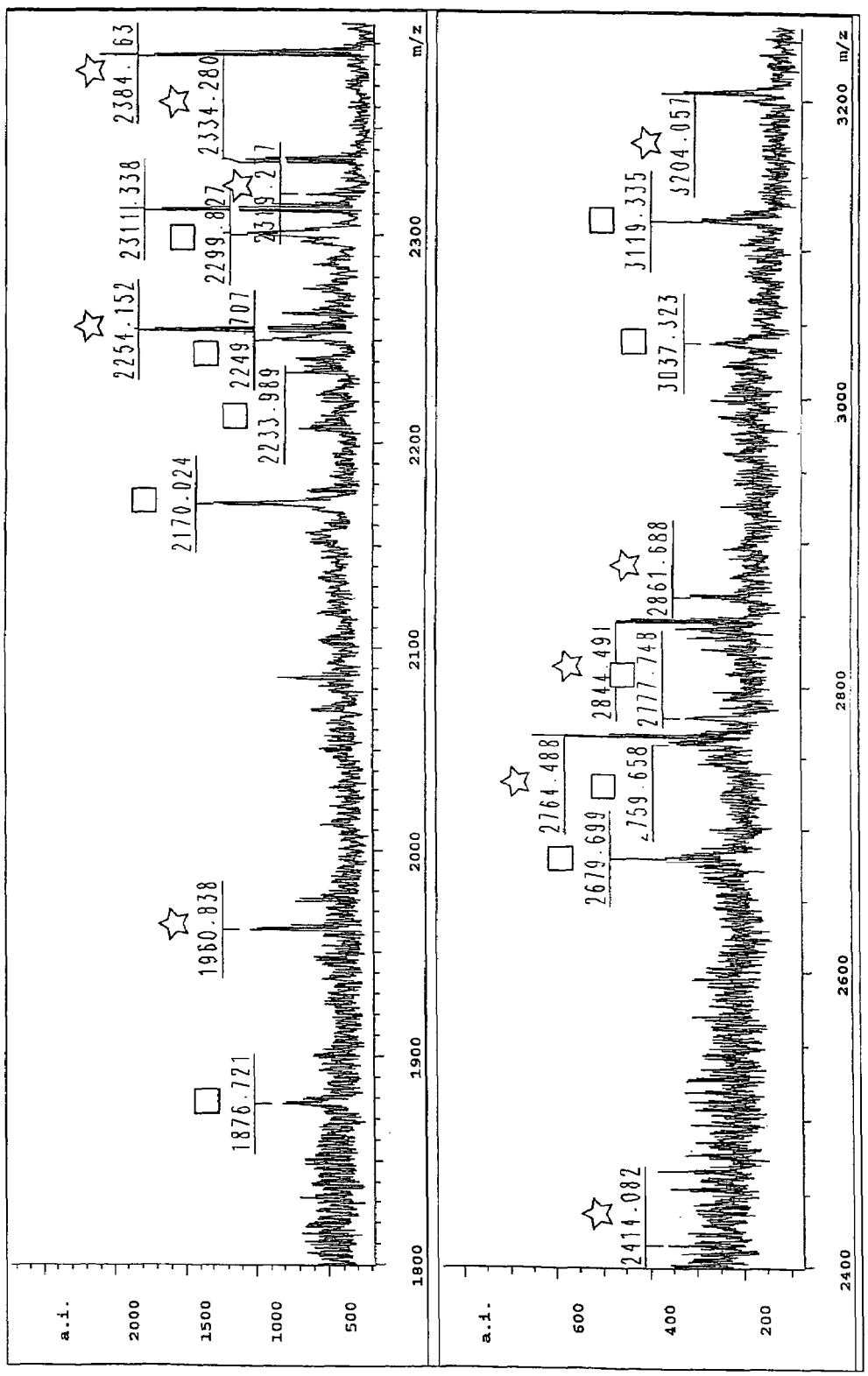
FIGURE 30: MALDI-TOF mass spectrum of modified peptides isolated from a treated COS-1 cell extract with immobilized phospho-(Ser) 14-3-3 binding site antibody.

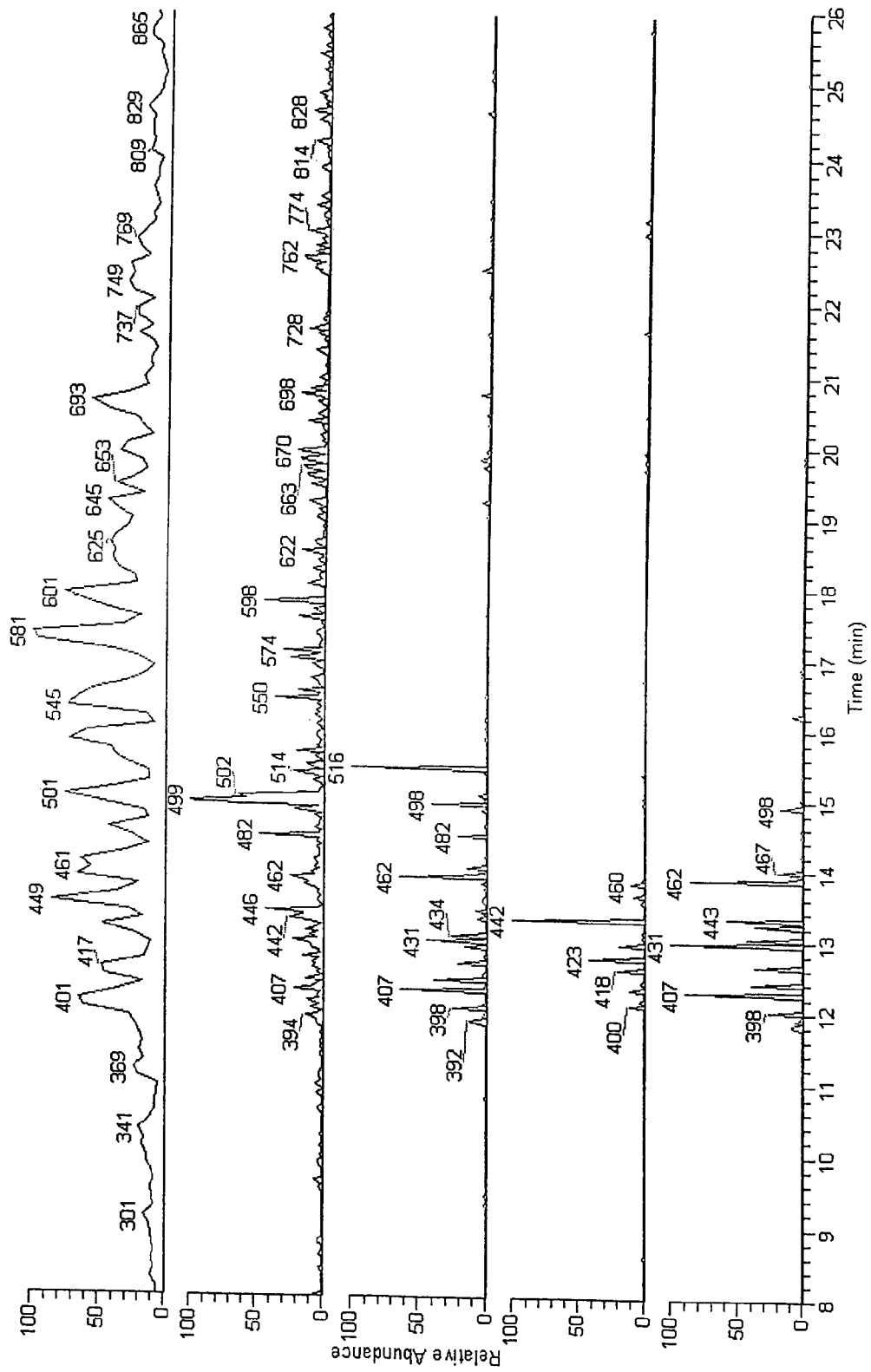
FIGURE 31: Various chromatograms obtained by LC-MS/MS spectrum of the modified peptides purified from a treated COS-1 cell extract with immobilized phospho-(Ser) 14-3-3 binding site antibody.

| LC-MS/MS Spectrum No. | m/z | z | m | Number of Phosphates | Seen by MALDI | Label in MALDI | Tentative Identification | Seen by LC-MS of Akt-3T3 |
|---|---|---|---|---|---|---|---|---|
| 454 | 746.800 | 3 | 2,237.379 | 1 | | | | |
| 442 | 752.540 | 3 | 2,254.599 | 1 | + | 2,254.152 | S6 + 1 PO$_4$ | + |
| 443 | 564.670 | 4 | 2,254.652 | 1 | + | as above | as above | + |
| 436 | 774.990 | 3 | 2,321.949 | 2 | | | | |
| 440 | 583.220 | 4 | 2,328.852 | 1 | | | | |
| 428 | 1,168.360 | 2 | 2,334.706 | 2 | + | 2,334.280 | S6 + 2 PO$_4$ | + |
| 418 | 779.220 | 3 | 2,334.639 | 2 | + | as above | as above | + |
| 420 | 585.030 | 4 | 2,336.092 | 2 | + | as above | as above | + |
| 516 | 1,192.610 | 2 | 2,383.206 | 1 | + | 2,384.163 | | |
| 423 | 803.800 | 3 | 2,408.379 | 2 | | | | |
| 400 | 805.720 | 3 | 2,414.139 | 3 | + | 2,414.082 | S6 + 3 PO$_4$ | + |
| 398 | 604.780 | 4 | 2,415.092 | 3 | + | as above | as above | + |
| 403 | 830.710 | 3 | 2,489.109 | 3 | | | | |
| 432 | 633.230 | 4 | 2,528.892 | 1 | | | | |
| 430 | 922.510 | 3 | 2,764.509 | 2 | + | 2,764.488 | | |
| 431 | 692.400 | 4 | 2,765.572 | 2 | | | | |
| 434 | 710.790 | 4 | 2,839.132 | 2 | | | | |
| 408 | 949.190 | 3 | 2,844.549 | 3 | + | 2,844.491 | | + |
| 407 | 712.240 | 4 | 2,844.932 | 3 | + | as above | | + |
| 412 | 730.590 | 4 | 2,918.332 | 3? | | | | |
| 391 | 732.120 | 4 | 2,924.452 | 3 | ? | | | |
| 392 | 750.660 | 4 | 2,998.612 | 3? | ? | | | |
| 460 | 1,069.440 | 3 | 3,205.299 | 2 | + | 3,204.057 | | + |
| 463 | 802.150 | 4 | 3,204.572 | 2 | | as above | | + |
| 462 | 820.490 | 4 | 3,277.932 | 2 | | | | |
| 467 | 838.850 | 4 | 3,351.372 | 2 | | | | |
| 451 | 1,288.970 | 3 | 3,863.889 | 2? | | | | |

For "Label in MALDI", values indicate masses as labeled in Figure 30.
Note masses above 3,600 were not measured during MALDI-TOF mass spectrometry.

FIGURE 32: Properties of the peptides that were observed to undergo neutral-loss during the LC-MS/MS analysis shown in Figure 31.

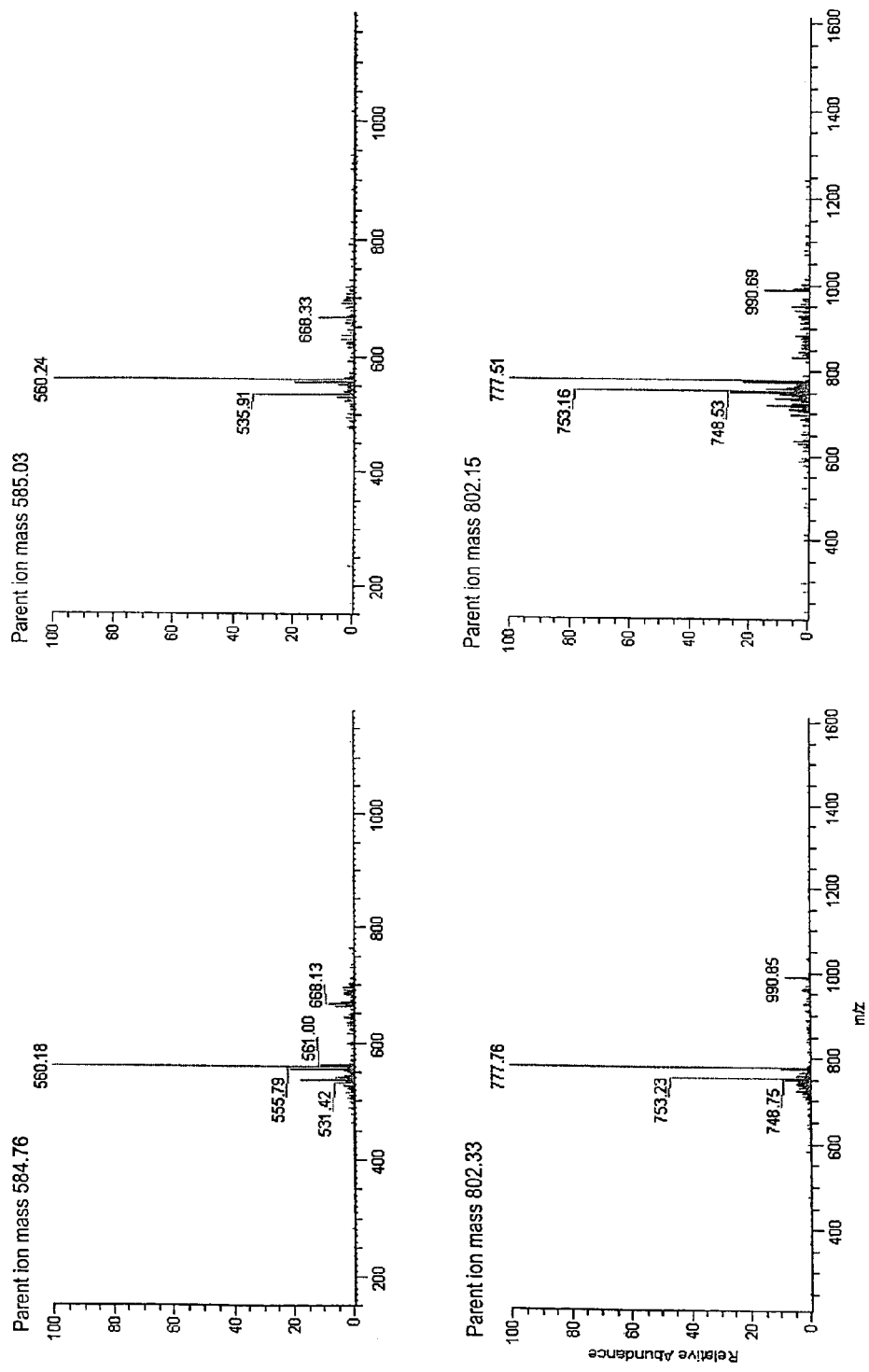
FIGURE 33: Two MS/MS spectra acquired during the LC-MS/MS analysis of two different samples, one prepared with phospho-(Ser/Thr) Akt substrate antibody (Figure 26) (left panels of this figure), the other prepared with phospho-(Ser) 14-3-3 binding site antibody (Figure 31) (right panels of this figure).

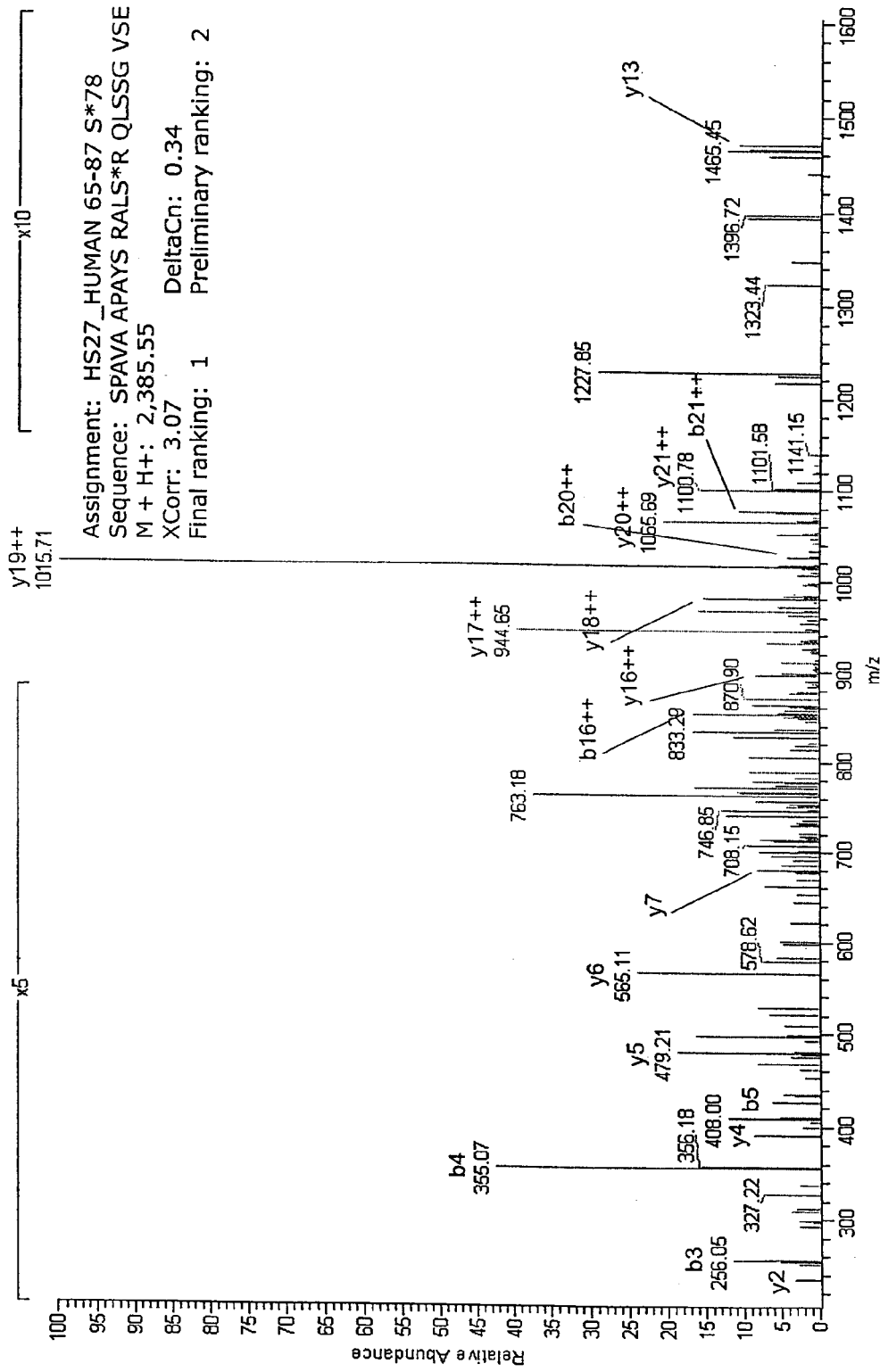
FIGURE 34: An LC-MS/MS spectrum of one of the modified peptides purified from a treated COS-1 cell extract with immobilized phospho-(Ser) 14-3-3 binding site antibody.

SEQUENCE LISTING

<160> NUMBER OF SEQ ID NOS: 163

<210> SEQ ID NO 1
<211> LENGTH: 19
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 1

Lys Ile Glu Lys Ile Gly Glu Gly Thr Tyr Gly Val Val Tyr Lys Gly
1               5                   10                  15

Arg His Lys

<210> SEQ ID NO 2
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 2

Lys Ile Glu Lys Ile Gly Glu Gly Thr Tyr Gly Val Val Tyr Lys Gly
1               5                   10                  15

Arg His Lys

<210> SEQ ID NO 3
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 3

Arg Leu Ile Glu Asp Asn Glu Tyr Thr Ala Arg Gln Gly Ala Lys Cys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 4

Arg Leu Ile Glu Asp Asn Glu Tyr Thr Ala Arg Gln Gly Ala Lys Cys
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES

```
<222> LOCATION: (7)..(7)
<223> OTHER INFORMATION: PHOSPHORYLATION; tyrosine at position 7 is
      phosphorylated

<400> SEQUENCE: 5

Leu Gln Glu Arg Arg Lys Tyr Leu Lys His Arg Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Leu Gln Glu Arg Arg Lys Tyr Leu Lys His Arg Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (6)..(6)
<223> OTHER INFORMATION: PHOSPHORYLATION; tyrosine at position 6  is
      phosphorylated

<400> SEQUENCE: 7

Arg Gln Gly Lys Asp Tyr Val Gly Ala Ile Pro Val Asp Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 8

Arg Gln Gly Lys Asp Tyr Val Gly Ala Ile Pro Val Asp Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 9

Gly Lys Asp Gly Arg Gly Tyr Val Pro Ala Thr Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Peptide
```

```
<400> SEQUENCE: 10

Gly Lys Asp Gly Arg Gly Tyr Val Pro Ala Thr Cys
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: PHOSPHORYLATION; threonine at position 8 is
      phosphorylated

<400> SEQUENCE: 11

Asp Thr Gln Ile Lys Arg Asn Thr Phe Val Gly Thr Pro Phe Cys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 12

Asp Thr Gln Ile Lys Arg Asn Thr Phe Val Gly Thr Pro Phe Cys
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (13)..(13)
<223> OTHER INFORMATION: PHOSPHORYLATION; threonine at position 13 is
      phosphorylated

<400> SEQUENCE: 13

Cys Lys Glu Gly Leu Gly Pro Gly Asp Thr Thr Ser Thr Phe
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 14

Cys Lys Glu Gly Leu Gly Pro Gly Asp Thr Thr Ser Thr Phe
1               5                   10

<210> SEQ ID NO 15
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: At positions 1 and 3, X = K or R; at positions
      2 and 4-5, X = any amino acid; at position 6, X = phosphothreonine
      or phosphoserine
```

```
<400> SEQUENCE: 15

Xaa Xaa Xaa Xaa Xaa Xaa
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: PHOSPHORYLATION; serine at position 9 is
      phosphorylated

<400> SEQUENCE: 16

Cys Ser Pro Arg Arg Arg Ala Ala Ser Met Asp Asn Asn Ser Lys Phe
1               5                   10                  15

Ala

<210> SEQ ID NO 17
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 17

Cys Ser Pro Arg Arg Arg Ala Ala Ser Met Asp Asn Asn Ser Lys Phe
1               5                   10                  15

Ala

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: PHOSPHORYLATION; threonine at position 8 is
      phosphorylated

<400> SEQUENCE: 18

Cys Leu Lys Asp Arg Gln Gly Thr His Lys Asp Ala Glu Ile Leu
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: PHOSPHORYLATION; threonine at position 7 is
      phosphorylated

<400> SEQUENCE: 19

Ser Arg Pro Arg Ser Cys Thr Trp Pro Leu Pro Arg Glu Ile
1               5                   10

<210> SEQ ID NO 20
<211> LENGTH: 15
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: PHOSPHORYLATION; threonine at position 5 is
      phosphorylated

<400> SEQUENCE: 20

Cys Arg Ser Leu Thr Gly Lys Pro Lys Leu Phe Ile Ile Gln Ala
1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

Cys Leu Lys Asp Arg Gln Gly Thr His Lys Asp Ala Glu Ile Leu
1               5                  10                  15

<210> SEQ ID NO 22
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 22

Ser Arg Pro Arg Ser Cys Thr Trp Pro Leu Pro Arg Glu Ile
1               5                  10

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 23

Cys Arg Ser Leu Thr Gly Lys Pro Lys Leu Phe Ile Ile Gln Ala
1               5                  10                  15

<210> SEQ ID NO 24
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION;  serine  at position 4 is
      phosphorylated
<220> FEATURE:
<221> NAME/KEY: MISC_FEATURE
<222> LOCATION: (1)..(5)
<223> OTHER INFORMATION: At position 1, X = K or R; at positions 2-3 and
      5, X = any amino acid

<400> SEQUENCE: 24

Xaa Xaa Xaa Ser Xaa Pro
1               5

<210> SEQ ID NO 25
<211> LENGTH: 17
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: PHOSPHORYLATION;  serine at position 9 is
      phosphorylated

<400> SEQUENCE: 25

Cys Ser Pro Arg Arg Arg Ala Ala Ser Met Asp Asn Asn Ser Lys Phe
1               5                   10                  15

Ala

<210> SEQ ID NO 26
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 26

Cys Ser Pro Arg Arg Arg Ala Ala Ser Met Asp Asn Asn Ser Lys Phe
1               5                   10                  15

Ala

<210> SEQ ID NO 27
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: PHOSPHORYLATION;  serine at position 7 is
      phosphorylated

<400> SEQUENCE: 27

Phe Arg Gly Arg Ser Arg Ser Ala Pro Pro Asn Leu Trp Ala Cys
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: PHOSPHORYLATION; threonine at position 7 is
      phosphorylated

<400> SEQUENCE: 28

Ser Arg Pro Arg Ser Cys Thr Trp Pro Leu Pro Arg Glu Ile
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: PHOSPHORYLATION;  serine at position 7 is
      phosphorylated
```

```
<400> SEQUENCE: 29

Thr Arg Ser Arg His Ser Ser Tyr Pro Ala Gly Thr Glu Glu Cys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: PHOSPHORYLATION; serine at position 9 is
      phosphorylated

<400> SEQUENCE: 30

Cys Ala Glu Tyr Leu Arg Ser Ile Ser Leu Pro Val Pro Val Leu
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: PHOSPHORYLATION; tyrosine at position 8 is
      phosphorylated

<400> SEQUENCE: 31

Leu Gln Glu Arg Arg Lys Tyr Leu Lys His Arg Cys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 32

Ser Arg Pro Arg Ser Cys Thr Trp Pro Leu Pro Arg Glu Ile
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 33

Thr Arg Ser Arg His Ser Ser Tyr Pro Ala Gly Thr Glu Glu Cys
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 34

Cys Ala Glu Tyr Leu Arg Ser Ile Ser Leu Pro Val Pro Val Leu
```

```
                     1               5              10              15

<210> SEQ ID NO 35
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: PHOSPHORYLATION; serine at position 9 is
      phosphorylated

<400> SEQUENCE: 35

Met Ser Gly Arg Pro Arg Thr Thr Ser Phe Ala Glu Ser Cys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 36

Arg Gln Gly Lys Asp Tyr Val Gly Ala Ile Pro Val Asp Cys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 37

Arg Gln Gly Lys Asp Tyr Val Gly Ala Ile Pro Val Asp Cys
1               5                   10

<210> SEQ ID NO 38
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: At positions 1, 2, and 6, X = R or K; at
      position 3, X= any amino acid; at position 4, X = S or T;
      at position 5, X = any hydrophobic amino acid.

<400> SEQUENCE: 38

Xaa Xaa Xaa Xaa Xaa Xaa
1               5

<210> SEQ ID NO 39
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION: serine at position 3 is
      phosphorylated
<220> FEATURE:
```

-continued

```
<221> NAME/KEY: MISC_FEATURE
<222> LOCATION: (1)..(5)
<223> OTHER INFORMATION: At positions 1 and 5, X= R or K; at position 2,
      X = any amino acid; at position 4, X = any hydrophobic amino acid.

<400> SEQUENCE: 39

Xaa Xaa Ser Xaa Xaa
1               5

<210> SEQ ID NO 40
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; serine at position 1 is
      phosphorylated
<220> FEATURE:
<221> NAME/KEY: MISC_FEATURE
<222> LOCATION: (3)..(5)
<223> OTHER INFORMATION: At positions 3 and 5, X = R or K; at position
      4, X = any amino acid

<400> SEQUENCE: 40

Ser Leu Xaa Xaa Xaa
1               5

<210> SEQ ID NO 41
<211> LENGTH: 19
<212> TYPE: PRT
<213> ORGANISM: Homo sapiens

<400> SEQUENCE: 41

Gln Ile Ala Lys Arg Arg Arg Leu Ser Ser Leu Arg Ala Ser Thr Ser
1               5                   10                  15

Lys Ser Glu

<210> SEQ ID NO 42
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; at position 5, X =
      phosphoserine or phosphothreonine
<220> FEATURE:
<221> NAME/KEY: MISC_FEATURE
<222> LOCATION: (2)..(6)
<223> OTHER INFORMATION: At positions 2 and 3, X = any amino acid; at
      position 6, X = F or Y.

<400> SEQUENCE: 42

Phe Xaa Xaa Phe Xaa Xaa
1               5

<210> SEQ ID NO 43
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 43

Ile Ile Glu Asp Asn Glu Tyr Thr Ala Arg
```

```
1               5                    10
```

```
<210> SEQ ID NO 44
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 44

Leu Ile Glu Asp Asn Glu Tyr Thr Ala Arg
1               5                    10

<210> SEQ ID NO 45
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 45

Val Leu Glu Asp Asp Pro Glu Ala Thr Tyr Thr Thr Ser Gly Gly Lys
1               5                   10                  15

<210> SEQ ID NO 46
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 46

Val Leu Glu Asp Asp Pro Glu Ala Ala Tyr Thr Thr Arg
1               5                   10

<210> SEQ ID NO 47
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 47

Val Tyr Ile Asp Pro Phe Thr Tyr Glu Asp Pro Asn Glu Ala Val Arg
1               5                   10                  15

<210> SEQ ID NO 48
<211> LENGTH: 28
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12
      is phosphorylated

<400> SEQUENCE: 48
```

```
Thr His Ala Val Ser Val Ser Glu Thr Asp Asp Tyr Ala Glu Ile Ile
1               5                   10                  15

Asp Glu Glu Asp Thr Tyr Thr Met Pro Ser Thr Arg
            20              25
```

<210> SEQ ID NO 49
<211> LENGTH: 9
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: PHOSPHORYLATION; tyrosines at positions 7
      and 8 are phosphorylated

<400> SEQUENCE: 49

```
Tyr Met Glu Asp Ser Thr Tyr Tyr Lys
1               5
```

<210> SEQ ID NO 50
<211> LENGTH: 33
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION; tyrosine at position 20 is
      phosphorylated

<400> SEQUENCE: 50

```
Gly Ser Ile Asp Arg Glu Asp Gly Ser Phe Gln Gly Pro Thr Gly Asn
1               5                   10                  15

Gln His Ile Tyr Gln Pro Val Gly Lys Pro Asp Pro Ala Ala Pro Pro
            20                  25                  30

Lys
```

<210> SEQ ID NO 51
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 51

```
Ile Ile Glu Asp Asn Glu Tyr Thr Ala Arg
1               5                   10
```

<210> SEQ ID NO 52
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 52

```
Gln Glu Asp Gly Gly Val Tyr Ser Ser Ser Gly Leu Lys
1               5                   10
```

<210> SEQ ID NO 53
<211> LENGTH: 10
<212> TYPE: PRT

```
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 53

Leu Ile Glu Asp Asn Glu Tyr Thr Ala Arg
1               5                   10

<210> SEQ ID NO 54
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 54

Ile Gly Glu Gly Thr Tyr Gly Val Val Tyr Lys
1               5                   10

<210> SEQ ID NO 55
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 55

Ile Tyr Gln Tyr Ile Gln Ser Arg
1               5

<210> SEQ ID NO 56
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 56

Tyr Glu Val Leu Lys Ile Ile Gly Lys Gly Ser Phe Gly Gln Val Ala
1               5                   10                  15

Arg

<210> SEQ ID NO 57
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 57

Gly Glu Pro Asn Val Ser Tyr Ile Cys Ser Arg
1               5                   10
```

```
<210> SEQ ID NO 58
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
phosphorylated

<400> SEQUENCE: 58

Ala Val Cys Ser Thr Tyr Leu Gln Ser Arg
1               5                   10

<210> SEQ ID NO 59
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 59

Thr Val Cys Ser Thr Tyr Leu Gln Ser Arg
1               5                   10

<210> SEQ ID NO 60
<211> LENGTH: 19
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 60

Val Ala Asp Pro Asp His Asp His Thr Gly Phe Leu Thr Glu Tyr Val
1               5                   10                  15

Ala Thr Arg

<210> SEQ ID NO 61
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 61

His Thr Asp Asp Glu Met Thr Gly Tyr Val Ala Thr Arg
1               5                   10

<210> SEQ ID NO 62
<211> LENGTH: 22
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 62

Leu Cys Asp Phe Gly Ser Ala Ser His Val Ala Asp Asn Asp Ile Thr
```

```
                1               5              10              15

Pro Tyr Leu Val Ser Arg
                20

<210> SEQ ID NO 63
<211> LENGTH: 24
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 63

Leu Pro Asp Phe Gln Asp Ser Ile Phe Glu Tyr Phe Asn Thr Ala Pro
1               5                  10                  15

Leu Ala His Asp Leu Thr Phe Arg
                20

<210> SEQ ID NO 64
<211> LENGTH: 20
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 64

Thr Leu Glu Pro Val Lys Pro Pro Thr Val Pro Asn Asp Tyr Met Thr
1               5                  10                  15

Ser Pro Ala Arg
                20

<210> SEQ ID NO 65
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 65

Tyr Val Asp Ser Glu Gly His Leu Tyr Thr Val Pro Ile Arg
1               5                  10

<210> SEQ ID NO 66
<211> LENGTH: 25
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 66

Ala Ser Gln Asp Tyr Asp Gln Leu Pro Ser Ser Ser Asp Gly Ser Gln
1               5                  10                  15

Ala Pro Ala Arg Pro Pro Lys Pro Arg
                20                  25
```

```
<210> SEQ ID NO 67
<211> LENGTH: 26
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 67

Thr Val Pro Pro Pro Val Pro Gln Asp Pro Leu Gly Ser Pro Pro Ala
1               5                   10                  15

Leu Tyr Ala Glu Pro Leu Asp Ser Leu Arg
            20                  25

<210> SEQ ID NO 68
<211> LENGTH: 29
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 68

Ile Pro Pro Gly Pro Ser Gln Asp Ser Val Tyr Ser Asp Pro Leu Gly
1               5                   10                  15

Ser Thr Pro Ala Gly Ala Gly Glu Gly Val His Ser Lys
            20                  25

<210> SEQ ID NO 69
<211> LENGTH: 22
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 69

Leu Thr Asp Ser Lys Glu Asp Pro Ile Tyr Asp Glu Pro Glu Gly Leu
1               5                   10                  15

Ala Pro Ala Pro Pro Arg
            20

<210> SEQ ID NO 70
<211> LENGTH: 23
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 70

Leu Lys Glu Glu Gly Tyr Glu Leu Pro Tyr Asn Pro Ala Thr Asp Asp
1               5                   10                  15

Tyr Ala Val Pro Pro Pro Arg
            20

<210> SEQ ID NO 71
<211> LENGTH: 14
<212> TYPE: PRT
```

-continued

<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 71

Gly Phe Ser Ser Asp Thr Ala Leu Tyr Ser Gln Val Gln Lys
1               5                   10

<210> SEQ ID NO 72
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 72

Asp Ala Ser Ser Gln Asp Cys Tyr Asp Ile Pro Arg
1               5                   10

<210> SEQ ID NO 73
<211> LENGTH: 21
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 73

Thr Gln Gln Gly Leu Tyr Gln Ala Pro Gly Pro Asn Pro Gln Phe Gln
1               5                   10                  15

Ser Pro Pro Ala Lys
            20

<210> SEQ ID NO 74
<211> LENGTH: 21
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 74

Val Gly Gln Gly Tyr Val Tyr Glu Ala Ala Gln Thr Glu Gln Asp Glu
1               5                   10                  15

Tyr Asp Thr Pro Arg
            20

<210> SEQ ID NO 75
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 75

Glu Glu Thr Tyr Asp Val Pro Pro Ala Phe Ala Lys
1               5                   10

<210> SEQ ID NO 76
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 76

Glu Tyr Asp Gln Leu Tyr Glu Glu Tyr Thr Arg
1               5                   10

<210> SEQ ID NO 77
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 77

Val Thr Ile Ala Asp Asp Tyr Ser Asp Pro Phe Asp Ala Lys
1               5                   10

<210> SEQ ID NO 78
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 78

Glu Leu Phe Asp Asp Pro Ser Tyr Val Asn Ile Gln Asn Leu Asp Lys
1               5                   10                  15

<210> SEQ ID NO 79
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 79

Leu Asp Tyr Cys Gly Gly Gly Gly Gly Asp Pro Gly Gly Gly Gln
1               5                   10                  15

Arg

<210> SEQ ID NO 80
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated -continued

```
<400> SEQUENCE: 80

Arg Val Pro Cys Ala Tyr Asp Lys
1               5

<210> SEQ ID NO 81
<211> LENGTH: 20
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 81

Gly Pro Leu Asn Gly Asp Thr Asp Tyr Phe Gly Gln Gln Phe Asp Gln
1               5                   10                  15

Leu Ser Asn Arg
            20

<210> SEQ ID NO 82
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 82

Lys Pro Leu Tyr Trp Asp Leu Tyr Gly His Val Gln Gln Gln Leu Leu
1               5                   10                  15

Lys

<210> SEQ ID NO 83
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 83

Gly Leu Tyr Asp Leu Pro Gln Glu Pro Arg
1               5                   10

<210> SEQ ID NO 84
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated
```

```
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 84

Leu Lys Glu Glu Gly Tyr Glu Leu Pro Tyr Asn Pro Ala Thr Asp Asp
1               5                   10                  15

Tyr Ala Val Pro Pro Arg
            20

<210> SEQ ID NO 85
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 85

Val Cys Glu Pro Cys Tyr Glu Gln Leu Asn Lys
1               5                   10

<210> SEQ ID NO 86
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 86

Gly Glu Pro Glu Ala Leu Tyr Ala Ala Val Thr Lys
1               5                   10

<210> SEQ ID NO 87
<211> LENGTH: 21
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 87

Val Gly Gln Gly Tyr Val Tyr Glu Ala Ala Gln Thr Glu Gln Asp Glu
1               5                   10                  15

Tyr Asp Thr Pro Arg
            20

<210> SEQ ID NO 88
<211> LENGTH: 36
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
```

```
         phosphorylated
<220> FEATURE:
<221> NAME/KEY: MOD_RES
<222> LOCATION: (29)..(29)
<223> OTHER INFORMATION: PHOSPHORYLATION; tyrosine at position 29 is
      phosphorylated

<400> SEQUENCE: 88

His Pro Leu Ile Leu Ala Ala Pro Pro Asp Ser Pro Ala Ala Glu
1               5                   10                  15

Asp Val Tyr Asp Val Pro Pro Ala Pro Asp Leu Tyr Asp Val Pro
            20                  25                  30

Pro Gly Leu Arg
        35

<210> SEQ ID NO 89
<211> LENGTH: 25
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 89

Val Leu Pro Pro Glu Val Ala Asp Gly Ser Val Val Asp Asp Gly Val
1               5                   10                  15

Tyr Ala Val Pro Pro Pro Ala Glu Arg
            20                  25

<210> SEQ ID NO 90
<211> LENGTH: 29
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 90

Leu Asn Glu Trp Leu Gly Asn Glu Asn Thr Glu Asp Gln Tyr Ser Leu
1               5                   10                  15

Val Glu Asp Asp Glu Asp Leu Pro His His Asp Glu Lys
            20                  25

<210> SEQ ID NO 91
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 91

Ile Gly Thr Ala Glu Pro Asp Tyr Gly Ala Leu Tyr Glu Gly Arg
1               5                   10                  15

<210> SEQ ID NO 92
<211> LENGTH: 28
<212> TYPE: PRT
<213> ORGANISM: Homo sapiens
<220> FEATURE:
<221> NAME/KEY: MOD_RES
```

```
<222> LOCATION: (21)..(22)
<223> OTHER INFORMATION: PHOSPHORYLATION; tyrosines at positions 21
      and 22 are phosphorylated

<400> SEQUENCE: 92

Met Ala Gly Phe Asp Gly Ser Ala Trp Asp Glu Glu Glu Glu Pro
1               5                   10                  15

Pro Asp His Gln Tyr Tyr Asn Asp Phe Pro Gly Lys
            20                  25

<210> SEQ ID NO 93
<211> LENGTH: 36
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 93

Ser Val Tyr Leu Gln Glu Phe Gln Asp Lys Gly Asp Ala Glu Asp Gly
1               5                   10                  15

Asp Glu Tyr Asp Asp Pro Phe Ala Gly Pro Ala Asp Thr Ile Ser Leu
            20                  25                  30

Ala Ser Glu Arg
        35

<210> SEQ ID NO 94
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 94

Ile Tyr Gln Phe Thr Ala Ala Ser Pro Lys
1               5                   10

<210> SEQ ID NO 95
<211> LENGTH: 23
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 95

Ser Gln Pro Ile Asp Asp Glu Ile Tyr Glu Glu Leu Pro Glu Glu Glu
1               5                   10                  15

Glu Asp Thr Ala Ser Val Lys
            20

<210> SEQ ID NO 96
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated
```

```
<400> SEQUENCE: 96

Leu Val Asn Glu Ala Pro Val Tyr Ser Val Tyr Ser Lys
1               5                   10

<210> SEQ ID NO 97
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 97

Val Ile Tyr Asp Phe Ile Glu Lys
1               5

<210> SEQ ID NO 98
<211> LENGTH: 19
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 98

Lys Pro Thr Tyr Asp Pro Val Ser Glu Asp Gln Asp Pro Leu Ser Ser
1               5                   10                  15

Asp Phe Lys

<210> SEQ ID NO 99
<211> LENGTH: 17
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 99

His Gln Glu Leu Gln Ala Met Gln Met Glu Leu Gln Ser Pro Glu Tyr
1               5                   10                  15

Lys

<210> SEQ ID NO 100
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 100

Thr Ser Thr Ile Met Thr Asp Tyr Asn Pro Asn Tyr Cys Phe Ala Gly
1               5                   10                  15
```

Lys

<210> SEQ ID NO 101
<211> LENGTH: 30
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 101

Gly Leu Gly His Gly Ala Phe Gly Glu Val Tyr Glu Gly Gln Val Ser
1               5                   10                  15

Gly Met Pro Asn Asp Pro Ser Pro Leu Gln Val Ala Val Lys
            20                  25                  30

<210> SEQ ID NO 102
<211> LENGTH: 18
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 102

Asn Lys Pro Thr Ser Leu Trp Asn Pro Thr Tyr Gly Ser Trp Phe Thr
1               5                   10                  15

Glu Lys

<210> SEQ ID NO 103
<211> LENGTH: 35
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 103

His Phe Pro Cys Gly Asn Val Asn Tyr Gly Tyr Gln Gln Gln Gly Leu
1               5                   10                  15

Pro Leu Glu Ala Ala Thr Ala Pro Gly Ala Gly His Tyr Glu Asp Thr
            20                  25                  30

Ile Leu Lys
        35

<210> SEQ ID NO 104
<211> LENGTH: 24
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 104

Asp Leu Asn Ser Leu Ile Ser Ser Asp Tyr Glu Leu Leu Ser Asp Pro
1               5                   10                  15

Thr Pro Gly Ala Leu Ala Pro Arg
            20

```
<210> SEQ ID NO 105
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 105

Ile Gly Glu Gly Thr Tyr Gly Val Val Tyr Lys
1               5                   10

<210> SEQ ID NO 106
<211> LENGTH: 11
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 106

Ile Gly Glu Gly Thr Tyr Gly Val Val Tyr Lys
1               5                   10

<210> SEQ ID NO 107
<211> LENGTH: 16
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 107

Val Tyr Asn Asp Gly Tyr Asp Asp Asp Asn Tyr Asp Tyr Ile Val Lys
1               5                   10                  15

<210> SEQ ID NO 108
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 108

Ile Tyr Gln Tyr Ile Gln Ser Arg
1               5

<210> SEQ ID NO 109
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 109

Tyr Glu Val Leu Lys Ile Ile Gly Lys Gly Ser Phe Gly Gln Val Ala
```

```
1               5                  10                  15

Arg

<210> SEQ ID NO 110
<211> LENGTH: 19
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 110

Val Ala Asp Pro Asp His Asp His Thr Gly Phe Leu Thr Glu Tyr Val
1               5                  10                  15

Ala Thr Arg

<210> SEQ ID NO 111
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 111

Gly Glu Pro Asn Val Ser Tyr Ile Cys Ser Arg
1               5                  10

<210> SEQ ID NO 112
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 112

Ala Val Cys Ser Thr Tyr Leu Gln Ser Arg
1               5                  10

<210> SEQ ID NO 113
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 113

His Thr Asp Asp Glu Met Thr Gly Tyr Val Ala Thr Arg
1               5                  10

<210> SEQ ID NO 114
<211> LENGTH: 22
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
```

-continued phosphorylated

<400> SEQUENCE: 114

Leu Cys Asp Phe Gly Ser Ala Ser His Val Ala Asp Asn Asp Ile Thr
1               5                   10                  15

Pro Tyr Leu Val Ser Arg
            20

<210> SEQ ID NO 115
<211> LENGTH: 18
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
    phosphorylated

<400> SEQUENCE: 115

Ile Ser Thr Tyr Gly Leu Pro Ala Gly Gly Ile Gln Pro His Pro Gln
1               5                   10                  15

Thr Lys

<210> SEQ ID NO 116
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
    phosphorylated

<400> SEQUENCE: 116

Gly Gln Glu Gly Glu Tyr Ala Val Pro Phe Asp Ala Val Ala Arg
1               5                   10                  15

<210> SEQ ID NO 117
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
    phosphorylated

<400> SEQUENCE: 117

Val Cys Glu Pro Cys Tyr Glu Gln Leu Asn Arg
1               5                   10

<210> SEQ ID NO 118
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
    phosphorylated

<400> SEQUENCE: 118

Leu Glu Tyr Tyr Glu Asn Glu Lys
1               5

<210> SEQ ID NO 119
<211> LENGTH: 41

```
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 119

Val Asp Pro Asn Gly Tyr Met Met Ser Pro Ser Gly Gly Cys Ser
1               5                  10                  15

Pro Asp Ile Gly Gly Gly Pro Ser Ser Ser Ser Ser Ser Asn Ala
            20                  25                  30

Val Pro Ser Gly Thr Ser Tyr Gly Lys
            35                  40

<210> SEQ ID NO 120
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 120

Arg Glu Glu Pro Glu Ala Leu Tyr Ala Ala Val Asn Lys
1               5                  10

<210> SEQ ID NO 121
<211> LENGTH: 16
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 121

Ile Lys Pro Ser Ser Ser Ala Asn Ala Ile Tyr Ser Leu Ala Ala Arg
1               5                  10                  15

<210> SEQ ID NO 122
<211> LENGTH: 28
<212> TYPE: PRT
<213> ORGANISM: Homo sapiens
<220> FEATURE:
<221> NAME/KEY: MOD_RES
<222> LOCATION: (21)..(22)
<223> OTHER INFORMATION: PHOSPHORYLATION; tyrosines at positions 21
      and 22 are phosphorylated

<400> SEQUENCE: 122

Met Ala Gly Phe Asp Gly Ser Ala Trp Asp Glu Glu Glu Glu Pro
1               5                  10                  15

Pro Asp His Gln Tyr Tyr Asn Asp Phe Pro Gly Lys
            20                  25

<210> SEQ ID NO 123
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
```

-continued phosphorylated

<400> SEQUENCE: 123

Glu Leu Phe Asp Asp Pro Ser Tyr Val Asn Val Gln Asn Leu Asp Lys
1               5                   10                  15

<210> SEQ ID NO 124
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 124

Ile Gln Asn Thr Gly Asp Tyr Tyr Asp Leu Tyr Gly Gly Glu Lys
1               5                   10                  15

<210> SEQ ID NO 125
<211> LENGTH: 26
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 125

Ser Cys Gln Asn Leu Gly Tyr Thr Ala Ala Ser Pro Gln Ala Pro Glu
1               5                   10                  15

Ala Ala Ser Ser Thr Gly Asn Ala Glu Arg
            20                  25

<210> SEQ ID NO 126
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 126

Ser Gln Asp Pro Asn Pro Gln Tyr Ser Pro Ile Ile Lys
1               5                   10

<210> SEQ ID NO 127
<211> LENGTH: 29
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 127

Gly Ser Pro Gly Glu Ala Pro Ser Asn Ile Tyr Val Glu Val Glu Asp
1               5                   10                  15

Glu Gly Leu Pro Ala Thr Leu Gly His Pro Val Leu Arg
            20                  25

<210> SEQ ID NO 128

```
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 128

Leu Ile Tyr Asp Phe Ile Glu Asp Gln Gly Gly Leu Glu Ala Val Arg
1               5                   10                  15

<210> SEQ ID NO 129
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 129

Val Leu Glu Asp Asp Pro Glu Ala Ala Tyr Thr Thr Arg
1               5                   10

<210> SEQ ID NO 130
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 130

Gln Glu Asp Gly Gly Val Tyr Ser Ser Ser Gly Leu Lys
1               5                   10

<210> SEQ ID NO 131
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 131

Asn Leu Asp Asn Gly Gly Phe Tyr Ile Ser Pro Arg
1               5                   10

<210> SEQ ID NO 132
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 132

Leu Ile Glu Asp Asn Glu Tyr Thr Ala Arg
1               5                   10
```

```
<210> SEQ ID NO 133
<211> LENGTH: 18
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 133

Ser Val Leu Glu Asp Phe Phe Thr Ala Thr Glu Gly Gln Tyr Gln Pro
1               5                   10                  15

Gln Pro

<210> SEQ ID NO 134
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 134

Ile Asp Thr Leu Asn Ser Asp Gly Tyr Thr Pro Glu Pro Ala Arg
1               5                   10                  15

<210> SEQ ID NO 135
<211> LENGTH: 20
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 135

Pro Met Pro Met Asp Thr Ser Val Tyr Glu Ser Pro Tyr Ser Asp Pro
1               5                   10                  15

Glu Glu Leu Lys
            20

<210> SEQ ID NO 136
<211> LENGTH: 12
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: PHOSPHORYLATION; tyrosines at positions 8 and 9
      are phosphorylated

<400> SEQUENCE: 136

Ala Leu Gly Ala Asp Asp Ser Tyr Tyr Thr Ala Arg
1               5                   10

<210> SEQ ID NO 137
<211> LENGTH: 11
<212> TYPE: PRT
<213> ORGANISM: Homo sapiens
<220> FEATURE:
```

```
<221> NAME/KEY: MOD_RES
<222> LOCATION: (6)..(6)
<223> OTHER INFORMATION: PHOSPHORYLATION; tyrosine at position 6 is
      phosphorylated <400> SEQUENCE: 137
Ile Gly Glu Gly Thr Tyr Gly Val Val Tyr Lys
1               5                   10

<210> SEQ ID NO 138
<211> LENGTH: 18
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 138

Ala Asp Gln Gln Tyr Glu Cys Val Ala Glu Ile Gly Glu Gly Ala Tyr
1               5                   10                  15

Gly Lys

<210> SEQ ID NO 139
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 139

Gly Glu Pro Asn Val Ser Tyr Ile Cys Ser Arg
1               5                   10

<210> SEQ ID NO 140
<211> LENGTH: 20
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 140

Gln Glu Gly Ser Ile Glu Val Tyr Glu Asp Ala Gly Ser His Tyr Leu
1               5                   10                  15

Cys Leu Leu Lys
            20

<210> SEQ ID NO 141
<211> LENGTH: 13
<212> TYPE: PRT
<213> ORGANISM: Homo sapiens
<220> FEATURE:
<221> NAME/KEY: MOD_RES
```

```
<222> LOCATION: (9)..(9)
<223> OTHER INFORMATION: PHOSPHORYLATION; tyrosine at position 9 is
      phosphorylated

<400> SEQUENCE: 141

His Thr Asp Asp Glu Met Thr Gly Tyr Val Ala Thr Arg
1               5                   10

<210> SEQ ID NO 142
<211> LENGTH: 22
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 142

Leu Cys Asp Phe Gly Ser Ala Ser His Val Ala Asp Asn Asp Ile Thr
1               5                   10                  15

Pro Tyr Leu Val Ser Arg
            20

<210> SEQ ID NO 143
<211> LENGTH: 20
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 143

Thr Leu Glu Pro Val Lys Pro Pro Thr Val Pro Asn Asp Tyr Met Thr
1               5                   10                  15

Ser Pro Ala Arg
            20

<210> SEQ ID NO 144
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 144

Gly Met Lys Asp Asp Asp Tyr Asp Asp Gln Leu Cys
1               5                   10

<210> SEQ ID NO 145
<211> LENGTH: 27
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 145

Ser Ala Thr Leu Leu Tyr Asp Gln Pro Leu Gln Val Phe Thr Gly Ser
1               5                   10                  15
```

```
Ser Ser Ser Ser Asp Leu Ile Ser Gly Thr Lys
            20                  25
```

<210> SEQ ID NO 146
<211> LENGTH: 29
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated
<220> FEATURE:
<221> NAME/KEY: MOD_RES
<222> LOCATION: (22)..(22)
<223> OTHER INFORMATION: PHOSPHORYLATION; tyrosine at position 22 is
      phosphorylated

<400> SEQUENCE: 146

```
Gly Pro Thr Ser Gly Pro Gln Ser Ala Pro Gln Ile Tyr Gly Pro Pro
1               5                   10                  15
Gln Tyr Asn Ile Gln Tyr Ser Ser Ala Ala Val Lys
            20                  25
```

<210> SEQ ID NO 147
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 147

```
Ala Gln Ile Pro Glu Gly Asp Tyr Leu Ser Tyr Arg
1               5                   10
```

<210> SEQ ID NO 148
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 148

```
Arg Glu Glu Pro Glu Ala Leu Tyr Ala Ala Val Asn Lys
1               5                   10
```

<210> SEQ ID NO 149
<211> LENGTH: 28
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 149

```
Glu Thr Asp Thr Ser Ala Leu Ala Ala Gly Ser Ser Gln Glu Val Thr
1               5                   10                  15
```

```
Tyr Ala Gln Leu Asp His Trp Ala Leu Thr Gln Arg
            20                  25

<210> SEQ ID NO 150
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 150

Leu Tyr Asp Leu Asn Met Pro Ala Tyr Val Lys
1               5                   10

<210> SEQ ID NO 151
<211> LENGTH: 27
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 151

Ile Ala Pro Cys Pro Ser Gln Asp Ser Leu Tyr Ser Asp Pro Leu Asp
1               5                   10                  15

Ser Thr Ser Ala Gln Ala Gly Glu Gly Val Gln
            20                  25

<210> SEQ ID NO 152
<211> LENGTH: 24
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated
<220> FEATURE:
<221> NAME/KEY: MOD_RES
<222> LOCATION: (20)..(20)
<223> OTHER INFORMATION: PHOSPHORYLATION; tyrosine at position 20 is
      phosphorylated

<400> SEQUENCE: 152

Glu Asp Pro Ile Tyr Asp Glu Pro Glu Gly Leu Ala Pro Val Pro Pro
1               5                   10                  15

Gln Gly Leu Tyr Asp Leu Pro Arg
            20

<210> SEQ ID NO 153
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated
```

```
<400> SEQUENCE: 153

Val Lys Glu Glu Gly Tyr Glu Leu Pro Tyr Asn Pro Ala Thr Asp Asp
1               5                   10                  15

Tyr Ala Val Pro Pro Arg
            20

<210> SEQ ID NO 154
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 154

Glu Asn Asp Tyr Glu Ser Ile Ser Asp Leu Gln Gln Gly Arg
1               5                   10

<210> SEQ ID NO 155
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 155

Ile Gly Thr Ala Glu Pro Asp Tyr Gly Ala Leu Tyr Glu Gly Arg
1               5                   10                  15

<210> SEQ ID NO 156
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 156

Asn Pro Gly Phe Tyr Val Glu Ala Asn Pro Met Pro Thr Phe Lys
1               5                   10                  15

<210> SEQ ID NO 157
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 157

Asp Ile Asn Ser Leu Tyr Asp Val Ser Arg
1               5                   10

<210> SEQ ID NO 158
```

```
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 158

Arg Gln Glu Glu Leu Asn Asn Gln Leu Phe Leu Tyr Asp Thr His Gln
1               5                   10                  15

Asn Leu Arg

<210> SEQ ID NO 159
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 159

Glu Leu Phe Asp Asp Pro Ser Tyr Val Asn Val Gln Asn Leu Asp Lys
1               5                   10                  15

<210> SEQ ID NO 160
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 160

Ser Gly Glu Ser Val Glu Glu Val Pro Leu Tyr Gly Asn Leu His Tyr
1               5                   10                  15

Leu Gln Thr Gly Arg
            20

<210> SEQ ID NO 161
<211> LENGTH: 19
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 161

Ser Gln Ala Ser Gly Pro Glu Pro Glu Leu Tyr Ala Ser Val Cys Ala
1               5                   10                  15

Gln Thr Arg

<210> SEQ ID NO 162
<211> LENGTH: 16
<212> TYPE: PRT
<213> ORGANISM: Homo sapiens
```

```
-continued

<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 162

Ala Ser Phe Pro Asp Gln Ala Tyr Ala Asn Ser Gln Pro Ala Ala Ser
1               5                   10                  15

<210> SEQ ID NO 163
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 163

Leu Ile Tyr Asp Phe Ile Glu Asp Gln Gly Gly Leu Glu Ala Val Arg
1               5                   10                  15
```

IMMUNOAFFINITY ISOLATION OF MODIFIED PEPTIDES FROM COMPLEX MIXTURES

RELATED APPLICATIONS

This application claims priority to U.S. Ser. No. 60/299,893, filed Jun. 21, 2001, and U.S. Ser. No. 60/337,012, filed Nov. 8, 2001, both abandoned, and is a continuation-in-part of U.S. Ser. No. 10/175,486, filed Jun. 19, 2002, presently pending, and U.S. Ser. No. 09/535,364, filed Mar. 24, 2000, now U.S. Pat. No. 6,982,318, itself a continuation-in-part of U.S. Ser. No. 09/148,712, filed Sep. 4, 1998, now U.S. Pat. No. 6,441,140, the disclosures of which are hereby incorporated by reference herein.

FIELD OF THE INVENTION

The invention relates to peptides and methods of isolating and characterizing the same.

BACKGROUND OF THE INVENTION

The activation of proteins by modification represents an important cellular mechanism for regulating most aspects of biological organization and control, including growth, development, homeostasis, and cellular communication. For example, protein phosphorylation plays a critical role in the etiology of many pathological conditions and diseases, including cancer, developmental disorders, autoimmune diseases, and diabetes. In spite of the importance of protein modification, it is not yet well understood at the molecular level. The reasons for this lack of understanding are, first, that the cellular modification system is extraordinarily complex, and second, that the technology necessary to unravel its complexity has not yet been fully developed.

The complexity of protein modification on a proteome-wide scale derives from three factors: the large number of modifying proteins, e.g. kinases, encoded in the genome, the much larger number of sites on substrate proteins that are modified by these enzymes, and the dynamic nature of protein expression during growth, development, disease states, and aging. The human genome encodes, for example, over 520 different protein kinases, making them the most abundant class of enzymes known. See Hunter, *Nature* 411: 355–65 (2001). Each of these kinases phosphorylates specific serine, threonine, or tyrosine residues located within distinct amino acid sequences, or motifs, contained within different protein substrates. Most kinases phosphorylate many different proteins: it is estimated that one-third of all proteins encoded by the human genome are phosphorylated, and many are phosphorylated at multiple sites by different kinases. See Graves et al., *Pharmacol. Ther.* 82: 111–21 (1999).

Many of these phosphorylation sites regulate critical biological processes and may prove to be important diagnostic or therapeutic targets for molecular medicine. For example, of the more than 100 dominant oncogenes identified to date, 46 are protein kinases. See Hunter, supra. Oncogenic kinases such as ErbB2 and Jak3, widely expressed in breast tumors and various leukemias, respectively, transform cells to the oncogenic phenotype at least in part because of their ability to phosphorylate cellular proteins. Understanding which proteins are modified by these kinases will greatly expand our understanding of the molecular mechanisms underlying, e.g., oncogenic transformation. Thus, the ability to selectively identify modification sites, e.g. phosphorylation sites, on a wide variety of cellular proteins represents an important new tool for understanding the key signaling proteins and pathways implicated in diseases, such as cancer.

Although several methods for purifying phosphopeptides have been described, these methods have significant limitations that render them unsuitable for the isolation or purification of modified peptides from complex mixtures of peptides on a genome- or cell-wide basis. In one method, which employs reversed-phase HPLC, proteins are labeled in vivo or in vitro with radioactive phosphate, and the protein of interest is purified to near homogeneity (so that it represents at least 95% of the protein in the sample) before analysis. See, e.g. Wettenhall et al. *Methods Enzymol.* 201: 186–199 (1991). The highly purified protein is then digested with a proteolytic enzyme to produce peptides, and the radioactively labeled peptides containing a phosphorylation site of the single protein are purified by reversed-phase HPLC. Phosphorylated peptides are distinguished from non-phosphorylated peptides by measuring the radioactivity associated with each HPLC fraction, and then chemically sequenced.

The reversed-phase HPLC method has several important limitations that render it unsuitable for the purification of modified peptides from complex mixtures of peptides, e.g. cellular digests. The method cannot be applied to biological samples that cannot be radioactively labeled, such as tissue biopsy samples. Selective peptide loss during purification by this method can introduce biases, so that the most prominent modified peptide before and after the HPLC step is not necessarily the same. This problem is addressed by first purifying the protein so its level of radioactivity can be measured and then rigorously accounting for sample recovery during all subsequent purification and analysis steps. Accordingly, modified sites cannot be identified from complex peptide mixtures. The HPLC method is often unsuccessful when applied to proteins that are modified at low levels, for example, where only a small percentage (less than 10%) of the protein is phosphorylated at one site. This problem results from the difficulty of purifying a phosphopeptide to homogeneity against a high background of non-phosphorylated peptides, and the need for a nearly homogenous phosphopeptide during chemical sequencing. Additional shortcomings of this method exist.

Several researchers have employed immobilized phospho-specific antibodies, along with mass spectrometry (MS or MS/MS), to identify phosphorylation sites in proteins. Immobilized anti-phosphotyrosine antibodies have been used to purify phosphopeptides from digests of gelsolin, an actin binding-protein. See De Corte, et al., *Prot. Sci.* 8: 234–241 (1999). However the single protein of interest, gelsolin, was first purified and phosphorylated in vitro, before digesting to yield gelsolin-specific phosphopeptides. Immobilized anti-phosphotyrosine antibodies have similarly been employed to identify EphB phosphopeptides from purified EphB digests (Kalo et al., *Biochem.* 38: 14396–408 (1999)) and to purify alpha-enolase phosphopeptides from a purified digest of human alpha-enolase (Marcus et al., *Electrophoresis* 21: 2622–2636 (2000)). However, in the latter attempt the method failed, and the authors expressly concluded that the low binding affinity between the antibody and the phosphopeptides makes the detection of phosphorylation sites almost impossible (Id. at p. 2635). The prevailing view (enunciated by Marcus et al.) that phosphospecific antibodies are not generally suitable for isolating phosphopeptides has recently been reiterated in a review on protein phosphorylation analysis authored by recognized leaders in the field of biological mass spectrometry. Mann et al., *Trends in Biotech*. 20: 261–268 (2002).

The identification of Ty1 Gag protein epitopes in digested yeast cell extract using an immobilized epitope-specific antibody has also been reported. See Yu et al., *J. Am. Soc. Mass. Spec*. 9: 208–215 (1998). However, the immobilized antibody was a Ty1 Gag epitope-specific antibody (i.e. was not a general modification-specific antibody), was not phospho-specific, and recognized only peptides from a single protein, Ty1 Gag. None of these methodologies are suitable for the selective isolation of phosphopeptides from complex mixtures of peptides that are derived from multiple, unpurified proteins, and most require the timely pre-purification of desired proteins. Reviewed in Mann et al., *Ann. Rev. Biochem*. 70: 437–73 (2001).

Another widely used method for purifying modified peptides is immobilized metal affinity chromatography (IMAC). This pseudo-affinity purification method is based on the interaction of metal ions and negatively charged peptide moieties, such as phosphate. See, e.g. Posewitz et al., *Anal. Chem*. 15: 2883–2892 (1999). Pre-purified, phosphorylated proteins are digested to peptides, and the phosphorylated peptides are then purified by passing the digest through a miniaturized chromatography column containing a resin with a covalently attached metal chelator, e.g. iminodiacetic or nitrilotriacetic acid. A cation is non-covalently attached to the chelator by treating the resin with one of several metal salts, such as $Fe^{3+}$, $Ni^{2+}$, $Ga^{3+}$, or $Cu^{2+}$. When the protein digest is applied to the column, peptides with a sufficiently high negative charge density, such as from a phosphate group, can bind to the metal cation. Eluted peptides can then be analyzed by chemical sequencing or by mass spectrometry (MS or MS/MS) to assign phosphorylation sites.

As with the reversed-phase HPLC method, IMAC purification of modified peptides has several limitations that render it unsuitable for the purification of modified peptides from complex mixtures of peptides, such as cellular digests. The method must be adjusted for each desired sample, since, phosphopeptides, for example, are sensitive to the exact conditions used for IMAC. It is not unusual to test peptide binding to all 4 commonly used cations in combination with 3 different pH conditions (12 test conditions altogether) in order to find the metal-pH combination best suited for purification of a single, specific phosphopeptide. Isolating a second, different phosphopeptide from the same, or different, protein may require a second metal-pH combination that is unique. The IMAC method is not specific for phosphopeptides, and peptides with several negatively charged amino acid residues (such as aspartic acid and glutamic acid) and without phosphate can bind to IMAC resins and contaminate any purified phosphopeptides. This drawback is especially problematic when only a small percentage of the protein sample is modified, e.g. a partially phosphorylated protein, because the background level of contaminating nonphosphorylated peptides can overwhelm the level of phosphopeptides. For this reason, the IMAC method is not suitable for the isolation of desired modified peptides from complex peptide mixtures. Further, the method is not specific for the type of modified residue, e.g. phosphorylated residue, thus peptides with phosphoserine, phosphothreonine, or phosphotyrosine all bind and elute from IMAC resins.

Accordingly, there remains a need in the art for the development of simple peptide isolation/purification methods that are suitable for the isolation of modified peptides from complex mixtures of peptides, e.g. digested cell extracts, which contain a wide variety of different, modified proteins, and yet do not require timely or costly pre-purification steps. The development of suitable peptide isolation methods that are simple and can be readily automated would, for example, enable the rapid profiling of activation states on a genome-wide basis and the identification of new diagnostic or therapeutic targets within cell signaling pathways that are at the forefront of the proteomics era currently underway. The unresolved need for such high-throughput methods has recently been recognized. See, e.g. Mann, *Nat. Biotech*. 17: 954–55 (1999).

SUMMARY OF THE INVENTION

The present invention provides methods for isolating a modified peptide from a complex mixture of peptides (such as exists in a cell extract digest) by the steps of: (a) obtaining a proteinaceous preparation from an organism, in which modified peptides from two or more different proteins are present; (b) contacting the proteinaceous preparation with at least one immobilized modification-specific antibody; and (c) isolating at least one modified peptide specifically bound by the immobilized modification-specific antibody. The method may further include the step of (d) characterizing the modified peptide(s) isolated in step (c) by mass spectrometry (MS), tandem mass spectrometry (MS-MS), and/or $MS^3$ analysis. The method may also further include the step of (e) utilizing a search program (such as Sequest) to substantially match the spectra obtained for the modified peptide(s) during the characterization of step (d) with the spectra for a known peptide sequence, thereby identifying the parent protein(s) of the modified peptide(s). The invention encompasses the isolation of modified peptides containing virtually any type of modified amino acids, including but not limited to phosphorylated, acetylated, methylated, nitrosylated, and/or glycosylated residues. Motif-specific, context-independent antibodies that bind single modified amino acids or that bind conserved modified motifs comprising multiple amino acids are advantageously employed in the disclosed methods.

Also provided are an immunoaffinity isolation device for the isolation of modified peptides from a complex mixture according to the method of the invention, and antibodies to novel UFD1 and PTN6 phosphorylation sites discovered by the practice of the disclosed methods.

The method of the invention enables the rapid, efficient, and direct isolation (and subsequent characterization) of modified peptides from complex mixtures, such as crude cell extracts, without the need for costly and timely pre-purification of desired peptides or proteins. The method enables the single-step immunoaffinity isolation, and subsequent characterization of multiple different modified peptides, corresponding to a multitude of different modified proteins and signaling pathways, with a single antibody. Alternatively, the method can further employ a simple pre-fractionation step. The simplicity of the disclosed method also renders it readily automatable, as only a single isolation step is required. Further advantages and preferred embodiments of the invention are described in detail below.

BRIEF DESCRIPTION OF THE DRAWINGS

FIG. 2—depicts a MALDI-TOF mass spectrum of an unpurified mixture of 10 different phosphorylated and non-phosphorylated peptides, using alpha-cyano-4-hydroxycinnamic acid as matrix. Peaks labeled with stars are phosphorylated peptides, and peaks labeled with circles correspond to nonphosphorylated peptides. Unmarked peaks are synthetic peptide byproducts.

FIG. 3—depicts a MALDI-TOF mass spectrum of the phosphotyrosine peptide mixture described in FIG. 2, after isolation of phosphopeptides with monoclonal P-Tyr-100 antibody-resin, according to the method of the invention. Peaks labeled with stars are phosphorylated peptides, and peaks labeled with primed stars correspond to a phosphopeptide artifact with a mass of M-78. These artifacts are also present in the unpurified peptide mix (FIG. 2) but are obscured by the peaks from nonphosphorylated peptides (M-80).

FIG. 4—depicts a MALDI-TOF mass spectrum of the purified and unpurified phosphotyrosine peptide mix described in FIG. 2, using alpha-cyano-4-hydroxycinnamic acid as matrix. The top panel shows the peptide mix before purification (as in FIG. 2), and the bottom panel shows the peptide mix after purification (FIG. 3).

FIG. 5—depicts a MALDI-TOF mass spectrum of an unpurified mixture of 4 different phosphorylated and nonphosphorylated peptides, using alpha-cyano-4-hydroxycinnamic acid as matrix. Peaks labeled with stars are phosphorylated peptides, and peaks labeled with circles correspond to nonphosphorylated peptides. Unmarked peaks are synthetic peptide byproducts.

FIG. 6—depicts a MALDI-TOF mass spectrum of the bound and unbound peptide fractions after immunoaffinity isolation/purification of the phosphothreonine peptide mix described in FIG. 5, using alpha-cyano-4-hydroxycinnamic acid as matrix. The top panel shows the fraction of the peptide mix that did not bind to a polyclonal P-Thr-antibody-resin, and the bottom panel shows the fraction of the peptide mix that did bind to and was eluted from the polyclonal P-Thr-antibody-resin. Peaks labeled with stars are phosphorylated peptides, and peaks labeled with circles correspond to nonphosphorylated peptides.

FIG. 7—depicts a MALDI-TOF mass spectrum of the unpurified and purified phosphotyrosine peptide mix described in FIG. 2, using alpha-cyano-4-hydroxycinnamic acid as matrix. This isolation is similar to the one described in FIGS. 2–4, except that the amount of phosphotyrosine peptide mix was reduced to a low level. In all panels, peaks labeled with stars are phosphorylated peptides, peaks labeled with circles correspond to nonphosphorylated peptides, and peaks labeled with primed stars correspond to a phosphopeptide artifact with a mass of M-78. The top panel shows the unpurified, complex phosphotyrosine peptide mix. The second panel shows the peptides that did not bind to the monoclonal P-Tyr-100 antibody-resin, and the third panel shows the peptides that did bind and elute from the antibody-resin. The bottom panel shows the bound and eluted peptide fraction after treatment with a phosphatase enzyme, to remove phosphate groups from phosphopeptides, reducing the observed mass by 80. Lines drawn between the third panel and the bottom panel show the relationships between phosphopeptides and dephosphorylated phosphopeptides.

FIG. 8—depicts a MALDI-TOF mass spectrum of the unpurified and purified phospho-Akt substrate peptide mix, using alpha-cyano-4-hydroxycinnamic acid as matrix. Peaks labeled with stars are phosphorylated peptides, peaks labeled with circles correspond to nonphosphorylated peptides, and peaks labeled with squares are metastable-decomposition phosphopeptide products. The top panel shows the peptide mix before purification and the bottom panel shows the peptide mix after purification.

FIG. 9—depicts a MALDI-TOF mass spectrum of the unpurified and purified 14-3-3 binding motif peptide mix, using alpha-cyano-4-hydroxycinnamic acid as matrix. Peaks labeled with stars are phosphorylated peptides, peaks labeled with circles correspond to nonphosphorylated peptides, and peaks labeled with squares are metastable-decomposition phosphopeptide products. Peaks labeled with filled stars are phosphopeptides that are not expected to bind to the 14-3-3 binding motif antibody because their sequences do not fit the antibody's known specificity. The top panel shows the peptide mix before purification and the bottom panel shows the peptide mix after purification.

FIG. 10—depicts a MALDI-TOF mass spectrum of the peptides purified by immobilized P-Tyr-100 antibody from a mixture containing a digested crude 3T3 cell extract, the phosphotyrosine peptide mix, and the phospho-Akt substrate peptide mix, using alpha-cyano-4-hydroxycinnamic acid as matrix (top panel). Peaks labeled with stars are phosphorylated peptides. The bottom panel shows the bound and eluted peptide fraction after treatment with a phosphatase enzyme, to remove phosphate groups from phosphopeptides, reducing the observed mass by 80. Arrows drawn between the top panel and the bottom panel show the relationships between phosphopeptides and dephosphorylated phosphopeptides.

FIG. 11—depicts a MALDI-TOF mass spectrum of the peptides purified by immobilized phospho-Akt substrate antibody from a mixture containing a digested crude 3T3 cell extract, the phosphotyrosine peptide mix, and the phospho-Akt substrate peptide mix, using alpha-cyano-4-hydroxycinnamic acid as matrix (top panel). Peaks labeled with stars are phosphorylated peptides, and peaks labeled with squares are metastable-decomposition phosphopeptide products. The bottom panel shows the bound and eluted peptide fraction after treatment with a phosphatase enzyme, to remove phosphate groups from phosphopeptides, reducing the observed mass by 80. Arrows drawn between the top panel and the bottom panel show the relationships between phosphopeptides and dephosphorylated phosphopeptides.

FIG. 12—depicts a MALDI-TOF mass spectrum of the peptides purified by immobilized 14-3-3 binding motif antibody from a mixture containing a digested crude 3T3 cell extract and the 14-3-3 binding motif peptide mix, using alpha-cyano-4-hydroxycinnamic acid as matrix. The top panel shows the peptide mix before purification, and the middle panel shows the peptide mix after purification. Peaks labeled with stars are phosphorylated peptides, peaks labeled with circles correspond to nonphosphorylated peptides, and peaks labeled with squares are metastable-decomposition phosphopeptide products. The bottom panel shows the bound and eluted peptide fraction after treatment with a phosphatase enzyme, to remove phosphate groups from phosphopeptides, reducing the observed mass by 80.

FIG. 13—depicts a Western blot of A431 cells overexpressing the epidermal growth factor receptor (EGFR) and probed with P-Tyr-100 antibody. Induction of EGFR expression is shown by the major band that appears after treating the cells with EGF.

FIG. 14—depicts a MALDI-TOF mass spectrum of modified peptides (phosphotyrosine) isolated from an A431 cell extract with P-Tyr-100 antibody-resin, using alpha-cyano-4-hydroxycinnamic acid as matrix. This cell line overexpresses the EGF receptor and was treated with EGF to induce phosphorylation at specific sites in the EGF receptor, as shown in FIG. 13. Peaks labeled with stars are phosphopeptides, and peaks labeled with circles correspond to nonphosphorylated peptides. Phosphopeptides purified from the digested lysate with P-Tyr-100 antibody-resin corresponded to two known major phosphorylation sites in the EGF receptor, as expected (top panel). The fraction was treated with phosphatase and reanalyzed (bottom panel) to confirm isolation of phosphopeptides. Lines drawn between the top and bottom panels indicate the relationships between phosphopeptides and dephosphorylated phosphopeptides.

FIG. 15—depicts a Western blot of 3T3 cells stably transfected to express active Src protein kinase constitutively and probed with P-Tyr-100 antibody. Comparison to untransfected cells shows the effect of Src expression on the number and level of proteins recognized by the P-Tyr-100 antibody.

FIG. 16—depicts a MALDI-TOF mass spectrum of modified peptides isolated from an extract of 3T3 cells transfected with Src protein kinase (as shown in FIG. 15) with immobilized P-Tyr-100 antibody, using alpha-cyano-4-hydroxycinnamic acid as matrix (top panel). Peaks labeled with stars are phosphorylated peptides, and peaks labeled with circles correspond to nonphosphorylated peptides. This bound-and-eluted peptide fraction was treated with phosphatase and reanalyzed (bottom panel) to confirm isolation of phosphopeptides.

FIG. 17—depicts an LC-MS/MS spectrum of one of the modified peptides purified from an extract of 3T3 cells transfected with Src protein kinase (as shown in FIG. 15) with immobilized P-Tyr-100 antibody. Portions of the spectrum were amplified to show low-intensity product ions. Sequest assigned this particular spectrum to a phosphotyrosine-peptide from enolase A. The peptide sequence and pertinent Sequest scores are shown. Peaks labeled "b" indicate product ions that contain the amino-terminus of the peptide, and "y" indicates product ions that contain the carboxyl-terminus. The number following the "b" or "y" label indicates the number of peptide residues in that ion. Doubly-protonated ions, i.e., ions with a charge (z) of 2, are labeled "++".

FIG. 18—depicts a Western blot of Jurkat cells treated with TPA and probed with phospho-(Ser) PKC substrate antibody. Comparison to untreated cells shows the effect of TPA treatment on the number and level of proteins recognized by the phospho-PKC substrate antibody.

FIG. 19—depicts a MALDI-TOF mass spectrum of modified peptides isolated from a TPA-treated Jurkat cell extract (as shown in FIG. 18) with immobilized phospho-PKC substrate motif antibody, using alpha-cyano-4-hydroxycinnamic acid as matrix (top panel). Peaks labeled with stars are phosphorylated peptides, peaks labeled with circles correspond to nonphosphorylated peptides, and peaks labeled with squares are metastable-decomposition phosphopeptide products. This bound-and-eluted peptide fraction was treated with phosphatase and reanalyzed (bottom panel) to confirm isolation of phosphopeptides.

FIG. 20—depicts various chromatograms obtained by LC-MS/MS analysis of the modified peptides purified from a TPA-treated Jurkat cell extract (as shown in FIG. 18) with immobilized phospho-PKC substrate motif antibody. The top panel shows where survey MS scans were collected (the y-axis value is the height of the tallest peak in each individual spectrum), and the second panel shows where MS/MS spectra were collected (the y-axis value is the sum of the heights of all peaks in each individual spectrum). The third, fourth, and fifth panels show where neutral loss of 49, 32.7, and 24.5, respectively, was detected (the y-axis value is the height of the neutral-loss ion). The peaks in each chromatogram are labeled with their corresponding spectrum numbers.

FIG. 21—depicts properties of the peptides that were observed to undergo neutral-loss during the LC-MS/MS analysis shown in FIG. 20, such as mass, phosphate content, and correspondence to peaks in the MALDI-TOF mass spectrum shown in FIG. 19.

FIG. 22—depicts some of the MS/MS spectra (left panels) and $MS^3$ spectra (right panels) acquired during LC-$MS^3$ analysis of the modified peptides purified from a TPA-treated Jurkat cell extract (as shown in FIG. 18) with immobilized phospho-PKC substrate motif antibody. Each $MS^3$ spectrum is grouped with its corresponding MS/MS spectrum, which caused the data-dependent $MS^3$ spectrum to be acquired. Sequest was able to assign parent proteins with good confidence to the three $MS^3$ spectra shown.

FIG. 23—depicts the MS/MS spectra (left panels) and $MS^3$ spectra (right panels) that confirm an assignment made by Sequest to one of the spectra in FIG. 22. The top panels show the spectra collected for a biological peptide and assigned by Sequest to UFD1_HUMAN residues 333–343 with phosphoserine at residue 335. The bottom panels are the spectra collected for a peptide that was synthesized with this sequence and phosphorylation site. The close correspondence of the biological peptide spectra and the synthetic peptide spectra confirms the assignment made by Sequest. Portions of the MS/MS spectra were amplified to show weak-intensity product ions.

FIG. 24—depicts a Western blot of 3T3 cells stably transfected to express active Akt protein kinase constitutively and treated with PDGF. The extract was analyzed by SDS-PAGE, blotted, and probed, using untransfected, untreated cells as a negative control. The top panel is probed with a general Akt antibody, the second panel with an antibody specific for phosphorylation at Akt residue Thr308, and the third panel with an antibody specific for phosphorylation at Akt residue Ser 473. The bottom panel is probed with phospho-(Ser/Thr) Akt substrate motif antibody. This shows that activation of Akt protein kinase is accompanied by an increase in the number and level of proteins recognized by the phospho-Akt substrate antibody. Other blotting experiments showed the major protein recognized by the phospho-Akt substrate antibody is the ribosomal protein S6.

FIG. 25—depicts a MALDI-TOF mass spectrum of modified peptides purified from an extract of 3T3 cells transfected with Akt protein kinase and treated with PDGF (as shown in FIG. 24), using alpha-cyano-4-hydroxycinnamic acid as matrix (top panel). Immobilized phospho-(Ser/Thr) Akt substrate motif antibody was used to purify modified peptides from the digested extract. Peaks labeled with stars are phosphorylated peptides, peaks labeled with circles correspond to nonphosphorylated peptides, and peaks labeled with squares are metastable-decomposition phosphopeptide products. All four phosphopeptides in the top panel are accompanied by metastable-decomposition products arising from neutral loss of phosphate. Two of these fit the expected masses for phosphopeptides from the ribosomal protein S6 (2,254.5 and 2,334.4). This fraction was treated with phosphatase and reanalyzed (bottom panel) to confirm isolation of phosphopeptides. Lines drawn between the top and bottom panels indicate the relationships between phosphopeptides and dephosphorylated phosphopeptides.

FIG. 26—depicts various chromatograms obtained by LC-MS/MS analysis of the modified peptides purified from a PDGF-treated 3T3 cell extract (as shown in FIG. 24) with immobilized phospho-(Ser/Thr) Akt substrate motif antibody. The top panel shows where survey MS scans were collected (the y-axis value is the height of the tallest peak in each individual spectrum), and the second panel shows where MS/MS spectra were collected (the y-axis value is the sum of the heights of all peaks in each individual spectrum). The third, fourth, and fifth panels show where neutral loss of 49, 32.7, and 24.5, respectively, was detected (the y-axis value is the height of the neutral-loss ion). The peaks in each chromatogram are labeled with their corresponding spectrum numbers.

FIG. 27—depicts properties of the peptides that were observed to undergo neutral-loss during the LC-MS/MS analysis shown in FIG. 26, such as mass, phosphate content, and correspondence to peaks in the MALDI-TOF mass spectrum shown in FIG. 25.

FIG. 28—depicts three MS/MS spectra acquired during the LC-MS/MS analysis shown in FIG. 26. These three spectra have been tentatively assigned to the multiply phosphorylated peptide from the ribosomal protein S6 with one (panel 1), two (panel 2), or three (panel 3) phosphate groups. Neutral loss of one, two, or three phosphate groups is readily apparent.

FIG. 29—depicts a Western blot of COS-1 cells treated with insulin and an analog of cAMP and probed with phospho-(Ser) 14-3-3 binding motif antibody. Comparison to untreated cells shows the effect of treatment on the number and level of proteins recognized by the phospho-(Ser) 14-3-3 binding motif antibody.

FIG. 30—depicts a MALDI-TOF mass spectrum of modified peptides isolated from a treated COS-1 cell extract (as shown in FIG. 29) with immobilized phospho-(Ser) 14-3-3 binding motif antibody, using alpha-cyano-4-hydroxycinnamic acid as matrix (top panel). Peaks labeled with stars are phosphorylated peptides, peaks labeled with circles correspond to nonphosphorylated peptides, and peaks labeled with squares are metastable-decomposition phosphopeptide products.

FIG. 31—depicts various chromatograms obtained by LC-MS/MS analysis of the modified peptides purified from a treated COS-1 cell extract (as shown in FIG. 29) with immobilized phospho-(Ser) 14-3-3 binding motif antibody. The top panel shows where survey MS scans were collected (the y-axis value is the height of the tallest peak in each individual spectrum), and the second panel shows where MS/MS spectra were collected (the y-axis value is the sum of the heights of all peaks in each individual spectrum). The third, fourth, and fifth panels show where neutral loss of 49, 32.7, and 24.5, respectively, was detected (the y-axis value is the height of the neutral-loss ion). The peaks in each chromatogram are labeled with their corresponding spectrum numbers.

FIG. 32—depicts properties of the peptides that were observed to undergo neutral-loss during the LC-MS/MS analysis shown in FIG. 31, such as mass, phosphate content, and correspondence to peaks in the MALDI-TOF mass spectrum shown in FIG. 30.

FIG. 33—depicts two MS/MS spectra acquired during the LC-MS/MS analysis of two different samples, one prepared with phospho-(Ser/Thr) Akt substrate motif antibody (FIG. 26) (left panels of this figure), the other prepared with phospho-(Ser) 14-3-3 binding motif antibody (FIG. 31) (right panels of this figure). In addition to prominent neutral-loss ions, the spectra have another prominent product ion in common. These spectra are thought to correspond to peptides that are present in both samples, due to similar induction conditions and to overlapping motifs recognized by the antibodies used for purification.

FIG. 34—depicts an LC-MS/MS spectrum of one of the modified peptides purified from a treated COS-1 cell extract (as shown in FIG. 29) with immobilized phospho-(Ser) 14-3-3 binding motif antibody. Portions of the spectrum were amplified to show low-intensity product ions. Sequest assigned this particular spectrum to a phosphoserine-peptide from heat shock 27 kDa protein. The peptide sequence and pertinent Sequest scores are shown. Peaks labeled "b" indicate product ions that contain the amino-terminus of the peptide, and "y" indicates product ions that contain the carboxyl-terminus. The number following the "b" or "y" label indicates the number of peptide residues in that ion. Doubly-protonated ions, i.e., ions with a charge (z) of 2, are labeled "++".

DETAILED DESCRIPTION OF THE INVENTION

Figure 1:
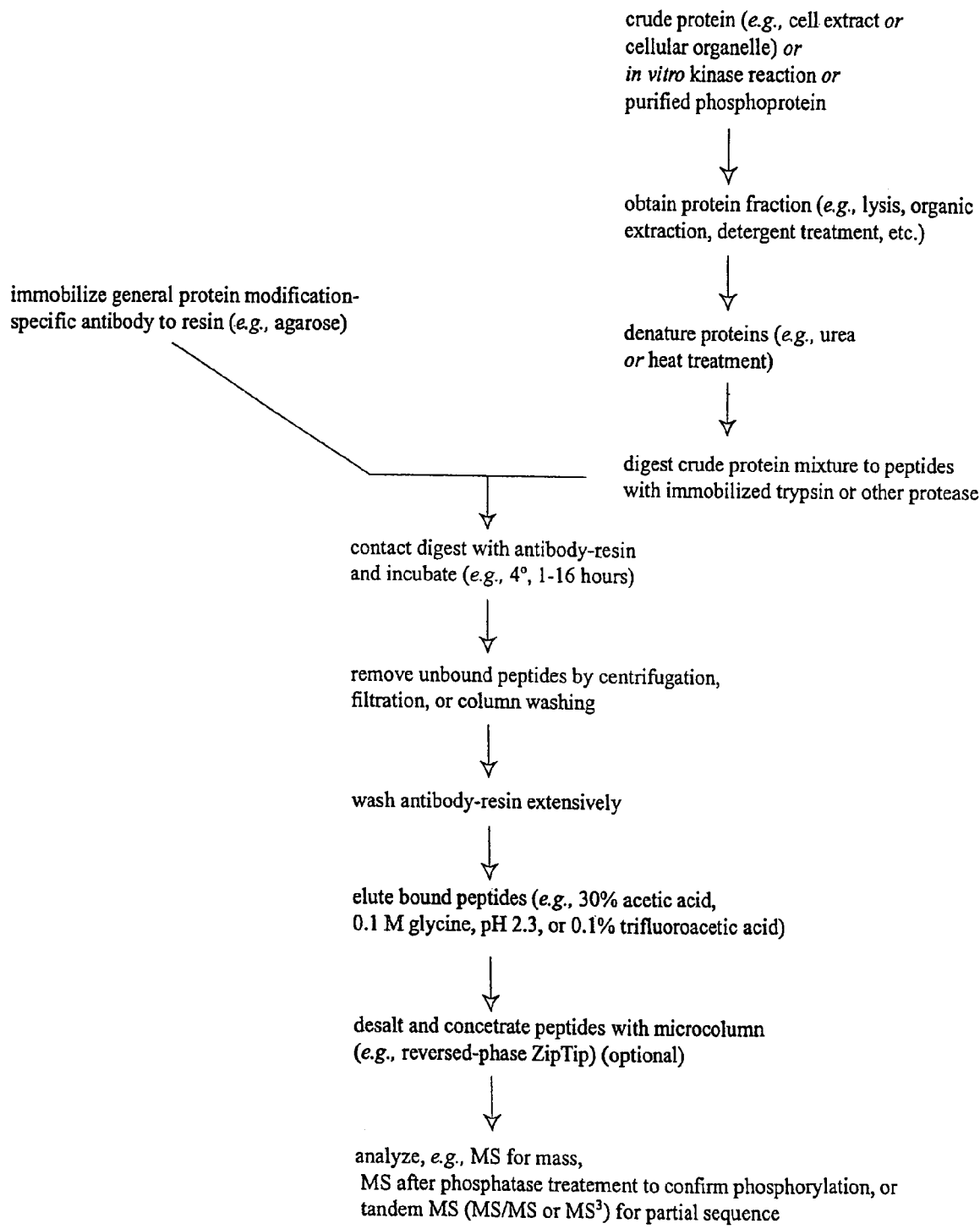
FIG. 1—is a flow-diagram representation of the method of the invention.

In accordance with the present invention, there is provided a general method for isolating a modified peptide (derived from a post-translationally modified protein) from a complex mixture of peptides, such as a digested cell lysate. In general, the method comprises the steps of: (a) obtaining a proteinaceous preparation from an organism, the protein preparation comprising modified peptides from two or more different proteins; (b) contacting the proteinaceous preparation with at least one immobilized modification-specific antibody; and (c) isolating at least one modified peptide specifically bound by the immobilized antibody in step (b). In a preferred embodiment, the method further comprises the step of (d) characterizing modified peptide(s) isolated in step (c) by mass spectrometry (MS), tandem mass spectrometry (MS-MS), and/or $MS^3$ analysis, or other equivalent method.

In another preferred embodiment, the invention provides a method for isolating a phosphopeptide from a complex mixture of peptides, the method comprising the steps of: (a) obtaining a proteinaceous preparation from an organism, wherein the proteinaceous preparation comprises phosphopeptides from two or more different proteins; (b) contacting the proteinaceous preparation with at least one immobilized motif-specific, context-independent antibody that binds a motif comprising at least one phosphorylated amino acid; (c) isolating at least one phosphopeptide specifically bound by the immobilized antibody in step (b); and (d) characterizing said modified peptide isolated in step (c) by mass spectrometry (MS), tandem mass spectrometry (MS-MS), and/or $MS^3$ analysis. In a preferred embodiment, step (a) further comprises digesting said proteinaceous preparation to produce a complex mixture of peptides. In another preferred embodiment, the motif of step (b) comprises all or part of a kinase consensus substrate motif or a protein-protein binding motif, or consists of a single phosphorylated amino acid.

In some preferred embodiments, the methods further comprise the step of (e) utilizing a search program to substantially match the spectra obtained for the isolated, modified peptide during the characterization of step (d) with the spectra for a known peptide sequence, thereby identifying the parent protein(s) of said modified peptide. In other preferred embodiments, the method further includes a quantification step employing, e.g. SILAC or AQUA, to quantify isolated peptides in order to compare peptide levels to a baseline or control state.

The method of the invention enables the single-step isolation (and subsequent characterization) of multiple different modified peptides, corresponding to a multitude of different modified proteins and signaling pathways, with a single antibody. The method is, therefore, suitable for genome-wide (e.g. cell-wide or organism-wide) profiling of activation states, and is readily automatable. The method allows, for example, the rapid, cell-wide profiling of modification states, such as phosphorylation, of many different proteins in a test cell or fluid (e.g. a diseased cell) as compared to a reference cell or fluid (e.g. a normal fluid from a healthy organism).

Motif-specific, context-independent antibodies may be advantageously employed in the disclosed methods. These antibodies bind short, modified motifs comprising one or more amino acids including at least one modified residue in a manner that is highly independent of the differing protein context in which the motif occurs in multiple signaling proteins within a genome. Motif-specific, context-independent antibodies, their production, and their applications are described in U.S. Ser. No. 09/148,712, Comb et al. (WO 00/14536). Genome-wide profiling of proteins using motif-specific, context-independent antibodies is generally described.

The isolation method of the present invention represents a significant advance over conventional methods for identifying modification sites in proteins, particularly with respect to the following:

(i) the method is useful for biological samples that have not been, or cannot be, radioactively labeled;

(ii) complex mixtures of peptides can be resolved in a single-step and there is no need for timely and costly purification before analysis;

(iii) the method utilizes affinity-chromatography and thus is more specific than existing methods, such as IMAC, since only modified peptides are purified, and unmodified peptides do not contaminate the purified, modified peptide fraction, even when the overall level of protein phosphorylation is very low;

(iv) the method specifically isolates the type of modified residue targeted by the affinity purification, thus, from one complex, unpurified mixture, the method can be used to isolate predefined, non-overlapping subsets of modified peptides (e.g. phosphotyrosine-containing peptides can be purified using a general protein modification antibody for phosphotyrosine, etc.);

(v) since the method is based on a stable antibody-antigen interaction, it does not have to be adjusted as different samples are analyzed;

(vi) the recognized problem with existing protein isolation methods of having non-specific peptides or proteins binding to, and co-eluting with, bound modified proteins is obviated since peptides, not proteins, are purified; accordingly, the present method eliminates the background associated with the non-specific co-isolation of proteins other than the desired modified protein; and (vii) the method is simpler and easier to use than existing methods, and is, therefore, particularly well-suited to high-throughput automation and reproduction.

As used herein, the following terms have the meanings indicated:

"peptide" means a fragment of a whole protein, e.g. a protease cleavage fragment, having a sequence two or more amino acids long;

"modified peptide" means a peptide having an amino acid sequence comprising at least one, but alternatively more than one, post-translationally-modified amino acid, for example (but not limited to), a phosphorylated amino acid such as phosphotyrosine, phosphoserine, or phosphothreonine, or an acetylated amino acid, such as acetyl-lysine; modified peptides may contain multiple modified residues of the same type (e.g. two or more phosphorylated residues) or may contain multiple modified residues of differing type (e.g. a phosphorylated residue and a glycosylated residue);

"complex mixture of peptides" means a substantially unpurified mixture of a plurality of different peptides corresponding to two or more different parent proteins, typically including both modified and unmodified peptides;

"proteinaceous preparation" means a preparation of proteins and/or peptides from one or more cells, tissues, or biological fluids of an organism, whether unpurified or purified (e.g. IMAC pre-purified), for example a crude cell extract, a proteolytic digest, serum, and the like;

"antibody" means a natural or recombinant antibody, polyclonal or monoclonal, derivative or fragment thereof, including $F_{ab}$, $F_{ab'}$, $F_{(ab')2}$ and F(v) fragments;

"modification-specific antibody" means an antibody that binds at least one modified amino acid, either alone or as part of a modified motif comprising multiple amino acids, including a general modification-specific antibody or a motif-specific, context-independent antibody;

"general modification-specific antibody" means an antibody that specifically binds a single modified amino acid, for example a general phosphotyrosine-specific antibody or a general acetyl-lysine specific antibody; the term includes, but is not limited to, a motif-specific, context-independent antibody that binds a motif consisting of a single modified amino acid;

"motif-specific, context-independent antibody" means an antibody that specifically recognizes a short amino acid motif (typically comprising 1 to 6 invariant amino acids) comprising at least one modified amino acid in a manner that is highly independent of the amino acid sequence surrounding (flanking) the motif in the peptide (i.e. it recognizes the modified motif in many, if not most, peptides in which it occurs), but does not substantially recognize peptides containing the unmodified form of the motif; (the production of such antibodies, which recognize a plurality of peptides or proteins within a genome that contain the target motif, has been previously described in Comb et al., WO 00/14536, supra.); the antibody may bind a motif consisting of a single modified amino acid or a motif comprising multiple amino acids including at least one modified amino acid (e.g. all or part of a kinase consensus substrate motif);

"parent protein" means the protein(s) from which a given peptide is (or potentially is) derived;

"phosphopeptide" means a peptide comprising at least one, but alternatively more than one, phosphorylated amino acid; and "protein-protein binding motif" means a short, modified motif that mediates signal transduction protein binding to a target protein, for example, 14-3-3 binding motifs, PDK1 docking motifs, SH2 domains, phosphotyrosine binding domains, and the like.

The teachings of all references cited in this specification are hereby incorporated herein by reference. Further aspects, advantages and uses of the invention are described in more detail below.

Proteinaceous Preparations

Proteinaceous preparations containing complex mixtures of peptides for isolation of modified peptides according to the method of the invention may be obtained from any desired organism. For example, the preparation may be obtained from bacteria, yeast, worms, amphibia, fish, plants, parasites, insects, or mammals. In a preferred embodiment, the organism is a mammal. In another preferred embodiment, the mammal is a human. The method can be applied to a proteinaceous preparation from one or more cell types or fluid samples derived from any organism. Proteinaceous preparations may be obtained, for example, by growing cells in tissue culture according to standard methods, harvesting the cells from culture media by centrifugation, and lysing the cells by sonication or other standard means of disrupting cells.

Proteinaceous preparations may also be obtained directly from tissue samples. In a preferred embodiment, the tissue sample is a biopsy sample. These small pieces of living tissue, typically weighing less than 500 milligrams, are taken directly from an organism and used directly without growth in tissue culture. The use of such living tissue allows direct analysis of the biological state of the tissue without introducing artifacts that may arise as a consequence of growth in culture. Any desired cell type from a given organism may be utilized. For example, tumor cells (e.g. from breast, prostate, etc.) may be cultured or obtained by biopsy to study proteins with roles in cancer. Neural cells lines are available to characterize proteins involved in neurotransmission. Fat cells can be cultured or obtained by biopsy to study proteins involved in the hormonal mechanisms of fat deposition. Proteinaceous preparations from tissue samples may contain peptides or proteins from multiple cell lines or types. In addition, cell lines with specific, desirable features could be engineered genetically, e.g., to overexpress a protein thought to have an important regulatory role in a specific pathway, e.g. cell lines overexpressing Akt protein. In other preferred embodiments, proteinaceous preparations are obtained from bodily fluids, such as serum, urine, spinal fluid, or synovial fluid. Preparations from blood samples may also be employed, whether cells, e.g. erythrocytes, are first removed or not.

Proteinaceous preparations are obtained by standard methods, e.g. for cells and tissues, by sonication, homogenization, abrasion, enzymatic digestion, or chemical solubilization. Generally the method used to lyse cells will be the one most commonly used for that specific cell type, e.g., enzymatic lysis for bacteria, abrasion for plant cells, and sonication for animal cells, but other desired methods may be suitably employed. Proteinaceous preparations for use in the method of the invention need not be extensively purified prior to the immunoaffinity isolation step. For example, urine samples or serum samples may be directly analyzed. This allows less sample processing, which increases the likelihood of identifying low-level modifications and makes it less likely that fractionation methods will bias or skew the profile of experimentally assigned modifications.

The mixture can be a crude cell lysate (for example, from tissue culture, a biopsy, or serum), a partially fractionated lysate (for example, a highly purified membrane or organelle), or a known and well-defined composition (for example, an in vitro modification reaction, that is, a protein modification enzyme allowed to react with one or more substrate proteins). However, if desired, simple purifications may be carried out to remove non-protein elements and/or non-signaling, structural proteins by standard methods, e.g. by centrifugation to remove erythrocytes, ultracentrifugation to remove cellular debris and cytoskeletal proteins, or by treatment with class-specific enzymes such as nucleases to remove DNA and RNA. In a preferred embodiment, the proteinaceous preparation is a crude cell extract or fluid, which has not been extensively purified.

Preferably, proteinaceous preparations are obtained so as to reflect the baseline, in vivo activation state, e.g. phosphorylation state, of proteins in a given cell, e.g. a breast cancer cell. However, proteinaceous preparations may be obtained from cells or organisms pre-treated with inducers. For example, cells grown in tissue culture can be exposed to chemicals such as calyculin or okadaic acid, which broadly elevate cellular phosphoprotein levels by inhibiting cellular phosphatases. Alternatively, a considerably narrower and more specific set of phosphoproteins in pathways can be induced by treatment with hormones, such as epidermal growth factor, that activate certain signaling pathways. Organisms can also be treated with drugs or infectious agents, and the effects of these treatments can be evaluated by isolating and analyzing specific tissues or fluids from the organism.

To obtain a complex mixture of peptides, the proteinaceous preparation, which contains a great variety of different proteins, is digested with a suitable proteolytic enzyme, e.g. trypsin or chemical cleavage reagent. Any suitable enzyme that yields a significantly digested proteinaceous preparation (i.e. mostly peptides as opposed to proteins) may be employed, for example endoproteinases Lys-C, Glu-C, Asp-N, chymotrypsin, and thermolysin. In a preferred embodiment, the enzyme is trypsin. If desired, digestion with two or more different proteolytic enzymes may be carried out to yield smaller peptides suitable for mass spectrometry analysis (e.g., peptides of about 30 amino acids in length or less, for current MS methods). Digestion of proteins may be carried out in an enzymatic solution or with immobilized proteolytic enzymes (e.g. trypsin-POROS resin, available from Applied Biosystems, Inc., Framingham, Mass.; trypsin-Matrix F7m, available from MoBiTec, Marco Island, Fla.), which can easily be removed from the digest by centrifugation or filtration before the preparation is contacted with the immobilized antibody. If soluble proteolytic enzymes are used, the digests are preferably treated with inhibitors such as PMSF or alpha-2-macroglobulin before the proteinaceous preparation is contacted with the immunoaffinity purification device, so that the proteolytic enzyme will not degrade the immobilized antibody molecules. Alternatively, soluble proteolytic enzymes are removed by pre-fractionating peptides by solid phase extraction prior to contact with the immobilized antibody. Digestions are conducted for a period of time sufficient for complete digestion, that is, for cleavage of all peptide bonds that can be cleaved by the protease. However, if the digestion is incomplete, intentionally or not, the overlap between partially digested peptides can provide further evidence that the phosphorylation site has been assigned correctly, i.e., when the same phosphorylation site is found in more than one peptide because the peptides overlap due to incomplete digestion, the site assignment is more convincing. In a preferred embodiment, a protease that can cleave at a large variety of residues, e.g., chymotrypsin, thermolysin, or elastase, is used for digestion in a manner that deliberately generates peptides with overlapping sequences.

Preferably, proteinaceous preparations for use in the method of the invention contain modified peptides, e.g. phosphopeptides, from two or more different proteins, and in most cases contain modified peptides from a multitude of different proteins. The proteinaceous preparation typically contains a complex mixture of many different types of modified, as well as unmodified, peptides. For example, such mixtures may contain peptides modified by phosphorylation, acetylation, methylation, sulfation, nitrosylation, or glycosylation, among others. See, e.g. Krishna et al., *Adv. Enzymol. Relat. Areas Mol. Biol.* 67: 265–98 (1993); Parekh et al., *Curr. Opin. Biotechnol.* 8: 718–23 (1997).

In a preferred embodiment, the proteinaceous preparation contains phosphopeptides from two or more different proteins. Accordingly, these complex mixtures of modified peptides reflect the activation state, e.g. phosphorylation state, of signaling pathways in a given organism or cell type on a genome-wide or cell-wide basis, thus providing a snap-shot of activation states in that organism. The complex mixture of modified peptides in the proteinaceous preparation reflects the baseline, in vivo activation status in the given organism or cell line, but may, as discussed above, reflect activation status in a treated cell, so as to reflect the effect of treatment upon activation status.

In certain preferred embodiments, the proteinaceous preparation comprises a digested biological sample selected from the group consisting of a digested crude cell extract, a digested tissue sample, a digested serum sample, a digested blood sample, a digested urine sample, a digested synovial fluid sample, and a digested spinal fluid sample. The digested preparation may be obtained using at least one proteolytic enzyme, such as trypsin. In a preferred embodiment, the proteolytic enzyme is immobilized. In another preferred embodiment, the proteolytic enzyme is soluble, and the said digested preparation is treated with a proteolysis inhibitor prior to the contacting step (b).

In one preferred embodiment the method is coupled with quantitative mass spectrometry approaches, so that modified peptides are identified and at the same time their levels in the sample are measured. The absence of a modified peptide is more meaningful when quantitative mass spectrometry approaches are used, because that peptide has been sought and not found, as opposed to overlooked. In addition, modified peptides that are present in two samples may be present at very different levels, but this difference is not easily recognized in qualitative identification studies, even though it may be a key feature of the system being studied. SILAC (stable isotope labeling by amino acids in cell culture) can be used for relative quantification of two cell culture samples, e.g., a cell line treated with a drug can be compared to the same cell line left untreated. See, e.g. Ong et al., *Mol. Cell. Proteomics* 5: 376–86 (2002). Another quantitative mass spectrometry strategy is termed Aqua for absolute quantification. See Gerber, Rush et al. *Proc. Natl. Acad. Sci. U.S.A.* 100: 6940–5 (2003). In Aqua a sample is compared to a panel of synthetic peptide standards, which serve as a reference control. Unlike SILAC, Aqua is better suited for the development of assays based on mass spectrometry, and it can be applied to tissue samples as well as cell cultures.

Immunoaffinity Isolation

The proteinaceous preparation, which contains a complex mixture of modified and unmodified peptides from a plurality of different proteins, is contacted with an immobilized, modification-specific antibody (e.g. anti-phosphothreonine) in order to isolate many, if not most, peptides containing the modification for which the immobilized antibody is specific. Peptides with the appropriate modification bind to the immobilized antibody, while unmodified peptides and/or peptides with other modifications do not. Thus, immunoaffinity purification according to the disclosed method allows the one-step isolation of a broad range of desired peptides (originating from different proteins) from substantially unpurified, complex mixtures of peptides.

In a preferred embodiment, the antibodies are covalently-linked to an inert chromatography resin, such as agarose, polystyrene, or silica, by standard techniques. Briefly, the carbohydrate groups of the antibody molecules are oxidized to reactive aldehyde groups, which are then covalently bonded to the hydrazide groups of derivatized chromatography resins. See, e.g. Hoffman et al., *J. Immunol. Methods* 9: 113–120 (1988). The carbohydrate groups of the antibody are not required for antigen recognition, so the chemical modification does not interfere with their ability to bind peptides. Using this standard method or others, antibodies are attached to chromatography supports at high concentrations, and because the antibodies are attached covalently to the resin, they do not leach off the support and contaminate purified samples. Alternatively antibodies may be immobilized by non-covalent attachment to protein A or protein G, which have been previously covalently linked to agarose resin, as in another preferred embodiment. It is simpler to immobilize antibodies to protein A- or protein G-agarose than it is to covalently immobilize antibodies to agarose. However antibodies immobilized to protein A or protein G supports have the disadvantage that they can be used only once, because the interaction of the antibody with protein A or protein G is disrupted by the conditions used to elute peptides from the antibody. When the complex mixture of peptides in the proteinaceous preparation is contacted with the antibody-resin, in either batch or column format, the antibody-resin selectively binds the modified peptides, even when they are present at low levels (i.e. picomole amounts).

For example, in batch format, the proteinaceous preparation is contacted with the antibody-resin by mixing as a slurry, and the antibody-resin with bound peptides is then removed by centrifugation, filtration, etc. Alternatively, in column format, the covalently-linked antibody-resin is contained within/packed in a chromatography column, and the proteinaceous preparation is passed through the column, so peptides that are recognized by the immobilized antibody are retained on the column and unrecognized peptides pass through the column. The antibody-resin may, in another preferred embodiment, be contained within a micropipette tip.

Column size, flow rates, and conditions (e.g. pH, choice of buffer) are selected in accordance with standard techniques. For low-level samples, a substance such as BSA, detergent, or polymer may be added to the proteinaceous preparation prior to contact with the immobilized antibody in order to prevent non-specific peptide loss through adsorption. The immunoaffinity purification step may be optimized, if desired, to ensure that all modified peptides in the sample are quantitatively bound to and eluted from the antibody-resin (i.e. little, if any, desired modified peptide is unbound). For example, the molar ratio of antibody to modified peptides, the amount of antibody per unit mass of antibody-resin, the length of time the sample contacts the antibody-resin (including recirculating the sample through an antibody-resin column), the temperature at which contact occurs, the inclusion of additives (e.g., salts, detergents, organic solvents, or polymers) that may enhance interaction of modified peptides with the antibody-resin, etc., may, if desired, each be optimized by the skilled artisan in practicing the method of the invention. Generally the metric for evaluating optimization is maximizing the number of modified peptides observed during analysis, with some emphasis given to minimizing the number of unmodified peptides that are isolated, which is a measure of the specificity of the method for modified peptides. This can be evaluated by MALDI-TOF mass spectrometry, before and after treatment with phosphatase, an enzyme that removes phosphate from peptides and lowers the measured masses of phosphopeptides. It can also be evaluated by the actual peptide sequences determined by tandem mass spectrometry. Other optimizations are possible, e.g., reducing the amount of time needed to analyze a sample without reducing the number of modified peptides identified and increasing the number of modified peptides identified by using different types of separation systems or mass spectrometers for analysis, e.g., capillary electrophoresis for separating peptides instead of reversed-phase HPLC, or quadrupole-time-of-flight hybrid mass spectrometry instead of ion trap mass spectrometry for analysis.

In a preferred embodiment, immunoaffinity isolation is carried out by utilizing a device consisting of one or more modification-specific antibodies immobilized to a rigid, non-porous or macroporous resin particle, packed into a thin capillary column, with an internal diameter of about 50 to 300 micrometers. While capillary columns of this type containing reversed-phase or ion exchange supports are already widely used, prior to the instant invention, capillary columns packed with immunoaffinity supports, as disclosed herein, have not been described. Immunoaffinity isolation devices of the invention may be constructed of any suitable material, for example, fused silica capillaries. The ends of the capillaries are drawn to fine tips, so the internal diameter at the tip is 3 micrometers or less, using an electronic microcapillary puller. The capillaries are then packed with chromatography resin using a Jorgensson and Kennedy pressure bomb, to force the resin slurry into the column through the back end. See Gatlin et al. *Anal. Biochem.* 263: 93–101 (1998). Resin particles are larger than the diameter of the capillary tip, so the resin accumulates in the column and is packed by pressure applied through the bomb. When the packed column has reached the desired length, the pressure is relieved, the empty back of the capillary is trimmed away, and the column is stored or used.

A preferred resin is POROS, a rigid macroporous resin developed at Perseptive Biosystems for use in perfusion chromatography. Resin particles are about 20 micrometers in diameter and are of uniform size. The resin is sold commercially through Applied Biosystems (Framingham, Mass.), including chemically derivatized resins for covalently attaching proteins such as antibodies. Other suitable types of resins known to those of skill in the art may be employed, for exampled, magnetic DynaBeads from Dynal.

This immunoaffinity isolation column can be adapted to be used as (i.e. coupled to) part of an electrospray source on a mass spectrometer, so that peptides can be readily analyzed after isolation with minimal sample loss. The capillary column itself is fitted directly to the mass spectrometer and acts as a fritless electrospray interface. For example, using standard low-volume HPLC fittings, the column is inserted into a plastic (PEEK) micro-tee fitting (shaped like the letter T). A capillary line from the HPLC solvent delivery system is attached to the opposite side of the micro-tee fitting, in line with the column, so different solvents or a gradient of solvents can be delivered at low flow rates, typical less than 1 microliter/minute, through the column to elute samples bound to the column. A gold rod is inserted into the third stem of the micro-tee, perpendicular to the solvent delivery lines and column, to supply the electrical connection from the mass spectrometer through a liquid-metal junction. All three devices are secured in the fitting with standard PEEK micro-fingertight fittings and tubing sleeves. The source normally used with the mass spectrometer is removed and replaced by a metal platform that holds this micro-tee assembly. The position of the capillary column tip can be precisely controlled by making adjustments with an XYZ micromanipulator on the platform, so the position of the spraying column tip relative to the mass spectrometer orifice is optimized for maximum ion current signal. In this way microcolumn liquid chromatography and micro-electro-spray ionization may be combined into one device.

The solutions used to elute bound samples from immunoaffinity columns, e.g., 30% acetic acid or 0.1 M glycine, pH 2.3, typically are not compatible with direct analysis by electrospray mass spectrometry. However, the immunoaffinity purification device can be used as the first component of a two-dimensional HPLC system, where an immunoaffinity purification column and a reversed-phase column are directly connected. A two-dimensional HPLC system using a strong cation exchange column upstream of a reversed phase column has been described. See, e.g. Washburn et al. *Nat. Biotech.* 19: 242–247 (2001).

The liquid stream from the HPLC system is diverted to waste during the immunoaffinity purification step. As samples elute from the immunoaffinity purification column, they bind to the downstream reversed-phase capillary column, but the solution components used for elution do not bind and are diverted to waste. The bound samples can then be eluted from the reversed-phase column using solvents that are compatible with direct analysis by electrospray mass spectrometry. Alternatively, the immunoaffinity step can be done off-line, using a solid-phase extraction cartridge in a micropipette tip, as described below, and then applied to a reversed-phase capillary column in an LC-MS/MS system. In both cases, the capillary columns are mounted in the mass spectrometer and samples are ionized as they elute from the column as described in Gatlin, supra.

Immunoaffinity isolation devices comprising capillary columns as described herein are useful not only for peptides that bind and elute from the column, but also for peptides that bind to the antibodies with lower affinity and whose passage through the column is retarded, extending the usefulness of the method. These columns would be reusable and have lifetimes comparable to other types of capillary HPLC columns. See, e.g. Gatlin, supra.

In another preferred embodiment, the immunoaffinity isolation device is a solid-phase extraction cartridge in a micropipette tip. Devices that have been constructed with reversed-phase and other types of HPLC supports (e.g., ZipTips from Millipore) have been described. See e.g., Erdjument-Bromage et al, *J. Chromatogr. A* 826: 167–181 (1998). These devices are attached to standard laboratory pipetting devices and are used in the same manner as pipette tips: as the sample is aspirated into the tip, it becomes bound to the chromatography support, which is then washed before eluting the sample in a small volume for analysis. The tip, for example, may be fabricated by embedding immobilized antibody-resin in a gel matrix in the dispensing end of a standard micropipette tip. See, e.g. Chirica et al., *Anal. Chem.* 72: 3605–3610 (2000). Taking advantage of the general stability of antibody molecules, these devices may be supplied dry; the end user would then rehydrate and condition the gel containing immobilized antibody immediately before use. These high-capacity, small-volume tips would be used to fractionate (i.e. isolating desired peptide) one sample and then discarded. Immunoaffinity separation may also be performed with other types of solid supports, such as porous filtration membranes or sample supports for MALDI-TOF mass spectrometry. See, e.g. Weller, *Fresenius J. Anal. Chem.* 366: 635–645 (2000); Liang et al. *Anal. Chem.* 70: 498–503 (1998).

Immunoaffinity isolation according to the method of the invention may be carried out without additional chromatography steps (e.g., reversed-phase or ion exchange chromatography). However, in some preferred embodiments, additional chromatography methods may be employed in conjunction with, and prior to, the single-step immunoaffinity isolation of the present method. For example, a digested cell lysate can be applied to a reversed-phase solid-phase extraction cartridge and fractionated by increasing the organic solvent concentration as the cartridge is washed in steps. Each fraction would thus be enriched for certain peptides, with minimal overlap between fractions, and the fractionated peptides could be more concentrated than the peptides in the unfractionated digested cell lysate. In the same manner, the digested cell lysate could be prefractionated with an ion-exchange solid-phase extraction cartridge, which would be developed by washing the cartridge in steps with increasing concentrations of salt.

In one preferred embodiment of the method, immobilized metal affinity chromatography (IMAC) is employed as an upstream pre-purification/fractionation step prior to immunoaffinity isolation as disclosed herein. As discussed earlier, although IMAC can enrich phosphopeptides from peptide mixtures, it has several important limitations (such as purification of phosphopeptides without specificity for the particular phosphorylated residue, purification of acidic peptides that are not phosphorylated, incomplete purification of phosphopeptides (i.e., some peptides do not bind or elute from the IMAC support), and poor reproducibility (which makes it difficult to compare samples)) which render it unsuitable for the selective and facile isolation of phosphopeptides from complex mixtures. Despite its limitations as a stand-alone technology, however, IMAC may be desirably employed as a bulk phosphopeptide enrichment/pre-purification step upstream of the method of the present invention.

For example, IMAC may be performed at very low stringency, in order to bind as many phosphopeptides as possible without regard for the much larger number of acidic non-phosphopeptides that would also bind to the IMAC support under these conditions. After elution from the IMAC column, the peptides would be fractionated further by the method of the invention, which would separate acidic non-phosphopeptides from phosphopeptides and which would further separate phosphopeptides into discrete subsets based on the particular residue that is phosphorylated. For example, peptides that contain phosphotyrosine and peptides that contain the Akt substrate binding motif would be separated from each other and could be isolated from the same IMAC-prepurified digested cell lysate. Thus the method of the invention may be desirably practiced in conjunction with other methods of phosphopeptide purification.

In another preferred embodiment, the method of the invention is used with several non-overlapping modification-specific antibodies in series to extract well-defined, distinct modified peptide populations from a single sample. For example, peptides containing phosphotyrosine are first extracted from a digested cell extract using immobilized phosphotyrosine antibody; the digested extract is then separated from the phosphotyrosine antibody-resin and treated with a second immobilized antibody, e.g., phosphothreonine-proline antibody, to extract phosphopeptides containing phosphothreonine-proline motifs. This process, which we have termed "rational fractionation" or "modified peptide sorting", can be repeated for as many steps as there are non-overlapping modification-specific antibodies. When each group of extracted, modified peptides is analyzed by mass spectrometry, identification of modified sites is simpler than for modified peptides that have been purified in bulk because the majority of peptides in each group are highly likely to contain a predetermined modification, e.g., phosphotyrosine or phosphothreonine-proline. With this strategy, sample complexity is addressed before analysis rather than after analysis, resulting in a larger number of high-confidence identifications.

Modification-Specific Antibodies

In accordance with the invention, immunoaffinity isolation is carried out by using at least one modification-specific antibody that specifically recognizes a given type of post-translational modification, e.g. phosphorylation, acetylation, methylation, nitrosylation, glycosylation, etc. Preferably, the modification-specific antibody is: (i) a general modification-specific antibody, that is, an antibody that binds a single modified amino acid residue, e.g. phosphothreonine, but does not recognize the unmodified amino acid residue, and/or (ii) a motif-specific, context-independent antibody produced by the method described in Comb et al., WO 00/14536, supra (also described below). Motif-specific, context-independent antibodies against many different phosphorylated kinase consensus substrate motifs and protein-protein binding motifs are commercially available. (See CELL SIGNALING TECHNOLOGY, INC. 2003-04 Catalogue & Technical Reference, pages 12–24).

The use of such modification-specific antibodies (both general and/or motif-specific, context-independent) thus allows the single-step isolation of many, if not most, peptides in a complex mixture that contain the modification or motif, regardless of the peptide sequence surrounding the modification or motif (i.e. these antibodies are not "site-specific" and hence are not limited to recognition of particular longer peptide sequences presenting a uniquely-occurring site epitope).

In a preferred embodiment of the method, the modification (on the peptides to be isolated) comprises phosphorylation and the modified peptide(s) isolated comprise(s) a phosphopeptide. Particularly preferred phosphorylated residues are phosphotyrosine, phosphoserine, phosphothreonine, or phosphohistidine. Although the invention is demonstrated in the Examples using phospho-specific antibodies, it will be recognized by those of skill in the art that other modification-specific antibodies may be readily employed, for example, acetylation-specific antibodies. Virtually any desired modified peptide may be isolated, as described in "Proteinaceous Preparations" above.

In certain preferred embodiments, motif-specific, context-independent antibodies are advantageously employed in the disclosed method to isolate many, if not most, peptides containing a desired modified motif. These antibodies and their production have previously been described. See Comb et al., WO 00/14536, supra. The antibodies bind to short, modified motifs, which, because of their small size and degenerate sequences, occur more than once in a given genome (i.e. occur in two or more different proteins, as opposed to larger, unique epitopes or "sites" that statistically occur only once) and thus serve, biologically, as consensus sequences and conserved binding sites for, e.g. kinases, in multiple proteins in cellular signaling pathways.

The invention may utilize antibodies specific for any desired motif of interest, e.g. signaling pathway motifs, comprising one or more modified amino acids. In certain preferred embodiments of the disclosed method, the modification-specific antibody used to isolate peptides comprises a motif-specific, context-independent antibody that recognizes a motif comprising at least one phosphorylated amino acid. In one preferred embodiment, the motif consists of a single phosphorylated amino acid, such as phosphotyrosine, phosphothreonine, or phosphoserine. In another preferred embodiment, the motif comprises all or part of a kinase consensus substrate motif or a protein-protein binding motif.

For example, in preferred embodiments, motif antibodies specific for all or part of any of the following kinase consensus or protein-protein binding motifs are used for immunoaffinity isolation: MAPK consensus substrate motifs, CDK consensus substrate motifs, PKA consensus substrate motifs, AKT consensus substrate motifs, PKC consensus substrate motifs, PDK1 docking motif (bulky ring), phosphothreonine-X-arginine, ATM/ATR consensus substrate motifs, 14-3-3 binding motifs, p85 PI3K binding motif, phosphothreonine-proline motif, Arg-X-Tyr/Phe-X-phosphoserine motif, and phosphoserine/phosphothreonine-Phe motif. (See, e,g. CELL SIGNALING TECHNOLOGY 2003–04 Catalogue at p.14). Context-independent antibodies against any desired kinase consensus substrate motif or protein-protein binding motif may be advantageously employed in the method of the invention; such motifs are well described in the literature (see, e.g., Kemp et al., *Trends in Biochem. Sci.* 15: 342–46 (1990); Kemp et al., *Methods in Enzymology* 200: 62–81 (1991); al-Obeidi et al., *Biopolymers* 47: 197–223 (1998); see also L. Cantley, overview in Cell Signaling Technology, Inc. 2000–2001 Catalogue at p. 198.)

The preparation of motif-specific, context-independent antibodies, previously described in Comb et al., WO 00/14536, supra (the disclosure of which are incorporated by reference in their entirety) is carried out briefly as follows:

(1) Motif-specific antibodies that react with any protein or peptide containing specific target residues independently of the surrounding amino acids may be obtained by synthesizing a highly degenerate peptide library. In one preferred embodiment, the library comprises XXXXXXJ*XXXXXXC where X=all 20 amino acids except cysteine and J*=a modified (*) amino acid (J). It will be appreciated that a shorter or longer library may be generated and less than all of the surrounding amino acids may be varied. For example, one to four X residues may be selectively biased for 1 or 2 specific amino acids, while the remaining X residues are highly degenerate. In one preferred embodiment, the peptide library is about 6 to 14 residues long. While one preferred embodiment utilizes one fixed amino acid (either modified or unmodified) in a varied surrounding context, other preferred embodiments may utilize a motif comprising several fixed amino acids. Likewise, the surrounding sequence of the library may be varied at more than one position simultaneously, or, as in the preferred embodiment, varied at only one surrounding sequence position per degenerate molecule, such that a library is produced which is completely degenerate at every position except the fixed residue(s). The peptide library can be synthesized by standard Fmoc solid phase peptide synthesis using an ABI peptide synthesizer and using mixtures of each amino acid during degenerate coupling reactions.

The incorporation of unmodified amino acids at fixed positions may be selected to mimic conserved motifs, for example zinc fingers or repeating arginine residues.

(2) In order to produce as equal a representation of each amino acid as possible at each degenerate position, several rounds of altering the amino acid composition, synthesizing, and peptide sequencing are conducted. Amino acid sequence analysis at several different positions along the peptide is conducted to verify a random amino acid representation at each position and that the random representation is maintained throughout the synthesis. It will be recognized by one of skill in the art that the number of rounds may vary in order to achieve an equal distribution of all amino acids at each position.

(3) The highly diverse peptide library is used as an antigen, preferably by covalent coupling to a carrier. In a preferred embodiment, keyhole limpet hemocyanin (KLH) emulsified in Freund's adjuvant is used as the coupling agent, and the coupled peptide library injected intradermally into a host, such as female New Zealand white rabbits. Booster injections may be given in incomplete Freund's adjuvant until an immune response is obtained. Antibody titer is measured by a suitable method, such as ELISA against the motif-specific peptide libraries. Antisera raised in this manner may be used in either crude or purified preparations, as outlined below.

(4) Antisera from the most promising hosts are purified, for example over protein A, and adsorbed over a J (non-modified) peptide library column. In the preferred embodiment, the nonadsorbed fraction (flow through) is then applied to a J* column, eluted at suitable pH, dialyzed and tested for J* specificity by a suitable method, such as ELISA using J* and J as antigen.

(5) Antibodies affinity purified in this fashion recognize the J* peptide library but do not react with the J library and exhibit a high degree of specificity for J*. These antibodies may be further tested for lack of reactivity against the unmodified form of the target modified amino acid, J*, or a J* homologue, utilizing a suitable method, such as ELISA.

(6) Antibodies may be further tested by western blotting, or another suitable method, using cell extracts prepared from cells treated with and without a selected protein modification enzyme inhibitor, such as protein phosphatase inhibitor okadaic acid. Treatments that increase protein modification will increase the number of antibody reactive proteins as well as the intensity of reactivity. The J* specific antibodies will react with a relatively small number of proteins from control extracts but will react with a very large number following treatment. The antibodies will show no reactivity with the inactive-non-modified versions of these proteins, demonstrating a high degree of J* specificity and suggesting broad cross-reactivity to many different modified-target containing proteins.

(7) The degree of context-independence may be more carefully examined, for example, by ELISA analysis against individual J* peptides that are mixed together or tested individually. Such analysis can indicate if poor reactivity occurs with certain motifs, such as when J* is followed by proline, for example.

(8) The context-dependence of J* antibody recognition may be further examined using an immobilized grid of modified-peptide libraries. In addition to a fixed target residue, J*, each different library is synthesized to contain an additional fixed amino acid at different positions relative to J* but with all other positions containing all 20 amino acids except cysteine. Each peptide library is coated, for example, on the bottom of an ELISA well and exposed to the J* antibodies. Antibodies that do not react with a particular spot (peptide library) on the grid do not bind when the specified amino acid is present at the specified position. This analysis determines whether or not a particular amino acid at a particular position relative to J* will allow or block binding.

Alternatively, purified antibodies can be linked to resin, allowed to bind the modified or unmodified library, unbound sequences washed away, and bound sequences recovered and subject to amino acid sequencing to determine the amount of each amino acid present at each position in the library. This information will indicate what amino acids are tolerated at each position.

Antibodies suitable for use in the method of the present invention may be polyclonal or monoclonal, or may be a fragment thereof, e.g. an $F_{ab}$ fragment, or a derivative thereof, e.g. a humanized antibody. A single antibody, e.g. a general phosphothreonine antibody, may be used in the immunoaffinity step, or two or more antibodies may be simultaneously used to isolate peptides containing different modifications, e.g. acetylated lysine and phosphothreonine. Alternatively, isolation of peptides with one modification may first be carried out with one immobilized antibody, and then peptides with other modifications may subsequently be purified using other immobilized antibodies and/or resins. This process, which we have termed "rational fractionation" or "modified peptide sorting", can be repeated for as many steps as there are non-overlapping modification-specific antibodies.

Following contact with the immobilized antibody, the antibody/resin is thoroughly washed to remove unbound peptides and then peptides bound to the antibody/resin (i.e. those containing the desired modification) are isolated from the resin by eluting with a small volume of an acidic solution, e.g. 30% acetic acid, or other suitable eluting solution. The eluted peptides are analyzed directly as described below, or concentrated and desalted with a micropipette tip containing reversed-phase resin, and then analyzed. If desired, peptide sequence and/or parent protein information is obtained by mass spectroscopy.

In certain circumstances, analysis of purified peptides (as described below) may indicate that some undesired peptides that lack the target motif are co-purified along with peptides that contain the desired target motif. In such cases, the number or stringency of the resin washes may be increased to eliminate non-specific peptide binding. Stringency of washes may be increased according to techniques well known in the art, for example, by including additives that reduce background binding, such as detergents, organic solvents, or polymers.

Analysis of Isolated Peptides

Isolated peptides containing the desired modification may be analyzed by standard methods to determine peptide sequence, activation state, and mass. In certain preferred embodiments, modified peptides isolated according to the method of the invention are analyzed by mass spectrometry (MS) methods, since MS is presently the most sensitive method for analyzing peptides. MS requires less analyte material to provide high-quality information about peptides than other current methods. It will be recognized by the skilled artisan that equivalent or subsequently improved methods of analyzing modified peptides are within the scope of the invention. For example, at present, peptides of about 30 amino acids in length or less are most suitable for MS analysis, but future improvements in methods may allow the analysis of longer peptides.

Accordingly, in a preferred embodiment, the general method of the invention further comprises the step of (d) characterizing the modified peptide(s) isolated in step (c) by mass spectrometry (MS), tandem mass spectrometry (MS-MS), and/or $MS^3$ analysis. In one preferred embodiment, matrix-assisted laser desorption/ionization time-of-flight (MALDI-TOF) mass spectrometry is utilized to measure the masses of purified peptides. MALDI-TOF mass spectrometry is useful for rapidly screening samples before analyzing them by other, more complex methods such as tandem mass spectrometry (MS/MS)(see below), and is both sensitive and simple. For proof-of-principle experiments or diagnostic assays, where the objective of the isolation is to determine if an expected peptide is present among the purified modified peptides, the mass of the purified peptide(s) is calculated from the peptide's known sequence and searched for in the mass spectrum.

MALDI-TOF mass analysis of peptides is a rapidly evolving field, and the preferred methods for preparing isolated modified peptides for analysis and carrying out such analysis is likely to change over time. Nonetheless, MALDI-TOF analysis is carried out according to standard methods (see, e.g. Courchesne et al., *Methods in Mol. Biol.* 112: 487–511 (1999)), and improvements in these methods are within the scope of the present invention. For example, isolated peptides are prepared for MALDI-TOF analysis using only a small portion, 1 to 20%, of the isolated (purified) modified peptide-containing fraction, and analyzed by mixing directly with a equal volume of saturated matrix solution, e.g. alpha-cyano-4-hydroxycinnamic acid, and drying the peptide-matrix solution on the MALDI-TOF sample plate. Other suitable matrix solutions may be alternatively employed. If necessary, a larger sample aliquot can be concentrated and desalted with a micropipette tip containing reversed-phase matrix before mixing it with matrix solution.

To confirm that purified peptides contain the desired modification, a small portion of the sample is preferably analyzed before and after treatment with an enzyme that removes the modified group from the peptide. For example, where the modified peptides being purified are phosphopeptides, phosphate is removed using a suitable phosphatase, e.g. calf intestinal phosphatase. See, e.g. Larsen et al. *Proteomics* 1: 223–238 (2001). This is a simple and reliable assay to confirm that peptides are modified, and to count the number of modified groups present in each peptide. For example, phosphatase treatment will reduce the observed peptide mass by 80 for each phosphate group in the peptide. The mass of a peptide that is not phosphorylated will not change as a result of phosphatase treatment. Similarly, any suitable modification-specific enzyme known in the art may be selected to confirm that peptides isolated according to the method of the invention contain the desired modification. See e.g., Krishna, supra.

If phosphopeptides are being isolated, metastable decomposition may result in the presence of additional peaks in the mass spectrum. Metastable decomposition of phosphopeptides has been noted by others and can be used to recognize and assign phosphopeptides in a MALDI-TOF mass spectrum (Annan and Carr, *Anal. Chem.* 68: 3413–21 (1996)). The peaks for decomposition products are broader than the peaks for phosphopeptides because the decomposition products form after ionization and the instrument is configured to focus ions that are stable during analysis. For similar reasons, the expected mass shift for loss of phosphate is −98, but −84 mass shifts are observed because, unlike a stable ion, the mass of a decomposition product changes during analysis. Analysis of a large number of synthetic phosphopeptides by MALDI-TOF mass spectrometry has indicated that some peptides containing phosphoserine or phosphothreonine—but not phosphotyrosine—residues undergo metastable decomposition. Accordingly, metastable decomposition is a reliable indicator of peptides that contain phosphoserine or phosphothreonine. Metastable decomposition may be observed in the MALDI-TOF spectra of some peptides that contain phosphoserine or phosphothreonine, without additional sample treatment steps and without consuming more sample.

In other types of applications, for example in a genome-wide analysis employing the disclosed method, it may not be possible to identify the modified peptides isolated from the complex mixture present in a proteinaceous preparation simply by measuring peptide masses because many different peptide sequences could produce each mass observed in the isolated modified peptide fraction. Accordingly, in another preferred embodiment, modified peptides isolated from complex mixtures (e.g. crude cell extracts) are analyzed by tandem mass spectrometry (MS/MS or $MS^3$), where peptide ions isolated in one stage of mass spectrometry are deliberately fragmented by collisions in the mass spectrometer, and then the fragment masses are measured. See, e.g. Yates, *Methods in Enzymology* 271: 351–377 (1996). The fragment masses observed for each peptide are a property of that peptide's sequence and are a more specific indicator of the parent protein than the peptide's mass, i.e. the fragment masses are related to the peptide's sequence and can be used to identify the protein from which the peptide originated. If the sequence of the peptide's parent protein is known, then the peptide can be unambiguously matched to its parent protein without directly interpreting a sequence from the fragment mass spectrum.

A particular peptide's measured mass and partial sequence is sufficient to unambiguously match it to its parent protein. See e.g. Eng et al. *J. Am. Soc. Mass Spectrom.* 5: 976–989 (1994). Parent protein sequences are increasingly becoming available as the genomes of common biological model organisms become known. MS/MS spectra can be collected rapidly (<400 msec per peptide) and in a data-dependent manner through instrument-control software, so very complex samples are amenable to analysis. With nano-spray infusion methods, sample volumes of 2 microliters can be analyzed for an hour or longer. See e.g. Wilm et al., *Anal. Chem.* 68: 1–8 (1996). Accordingly, in a preferred embodiment of the disclosed method, modified peptides isolated in step (c) are characterized by tandem MS, for example liquid chromatography (LC)-MS/MS (as described in Example IV).

If phosphopeptides are being isolated, it may be observed that during the fragmentation process of MS/MS, peptides containing phosphoserine or phosphothreonine often form an ion by simple loss of phosphate to produce a neutral-loss ion that has a mass 98 lower than the unfragmented parent ion. If the parent ion has a charge of +1, the neutral-loss ion has a mass-to-charge value (m/z) of 98/1 or 98 lower than the parent ion mass-to-charge value. Likewise, phosphopeptide parent ions with charges of +2, +3, or +4 will give neutral-loss ions with m/z values that are 49, 32.7, and 24.5 lower than the parent ion.

Neutral loss during MS/MS is the same process as metastable decomposition during MALDI-TOF mass spectrometry. Therefore many of the phosphopeptides showing neutral loss during LC-MS/MS are expected to be the same phosphopeptides that give metastable decomposition during MALDI-TOF mass spectrometry. For each neutral-loss MS/MS spectrum, the parent ion mass (m) can be calculated from the parent ion mass-to-charge value (m/z) and the charge (z) inferred from the neutral loss value (+2 for neutral loss of 49, +3 for 32.7, and +4 for 24.5). Some individual peptides may be observed to undergo neutral loss as +2, +3, and +4 ions. A comparison of datasets can confirm that the same peptides are detected by both mass analysis methods.

Additional steps can be incorporated into the method of the invention as needed to identify modified peptides that give high levels of neutral loss during MS/MS and correspondingly low levels of peptide background fragmentation. One approach is to analyze these peptides with a mass spectrometer that uses a different fragmentation mechanism, expecting this will change the distribution of unproductive neutral-loss fragmentation to productive peptide backbone fragmentation. For example, analysis with ion trap mass spectrometers may exacerbate neutral loss because fragmentation is induced by gradually increasing the energy of the trapped peptide ion over a relatively long period of time, whereas analysis with a triple quadrupole mass spectrometer may allow more backbone fragmentation because the peptide ions become energized for fragmentation more suddenly. A second approach is to chemically treat modified peptides that have been purified by the method of the invention in a manner that removes the group that undergoes neutral loss during MS/MS but leaves a "remnant" indicating where the group was. For example, phosphate groups can be removed chemically from phosphopeptides by beta-elimination. See, e.g., Byford, *Biochem J.* 280: 261–5 (1991). Exposing the peptides briefly to a base, such as NaOH, LiOH, or $Ba(OH)_2$, results in the removal of phosphoric acid from phosphoserine and phosphothreonine, leaving dehydroalanine and dehydroaminobutyric acid, respectively, which can be distinguished from serine and threonine residues in the peptide by mass: residue masses are 69 for dehydroalanine, 87 for serine, 167 for phosphoserine, and 83 for dehydroaminobutyric acid, 101 for threonine, 181 for phosphothreonine. Beta-eliminated peptides can be analyzed by tandem mass spectrometry directly or after further reaction with a Michael addition reagent. See, e.g., Molloy and Andrews, *Anal Chem.* 73: 5387–94 (2001).

Following MS/MS characterization, modified peptides may be unambiguously identified by analyzing the product ion spectra with a search program in an attempt to match the spectra obtained for the modified peptide with the spectra for a known peptide sequence, thereby identifying the parent protein(s) of the modified peptide. For example, Sequest, a program that correlates an experimental spectrum to a library of theoretical spectra derived from protein sequence databases to find a best-fit match, may advantageously be used for such a search. It will be recognized that equivalent search programs may be employed in the practice of disclosed method. Accordingly, in a preferred embodiment, the method of the invention further comprises the step of (e) utilizing a search program to substantially match the spectra obtained for the modified peptide during the characterization of step (d) with the spectra for a known peptide sequence, thereby identifying the parent protein(s) of the modified peptide.

In certain cases, if phosphopeptides are being isolated, it may be observed that, during MS/MS, some phosphopeptides undergo neutral loss to a very high degree, with very little residual fragmentation along the peptide backbone (which is needed to produce spectra of a quality high enough for unambiguous assignments). In such cases, analysis of MS/MS product ion spectra using a search program (such as Sequest) in an attempt to assign a phosphorylation site and parent protein to each peptide may not result in unambiguous assignments. This is a common limitation encountered during MS/MS analysis of peptides containing phosphoserine and phosphothreonine. See e.g., DeGnore et al., *J. Am. Soc. Mass Spectrom.* 9: 1175–1188 (1998). Even when phosphopeptides lose phosphate by neutral loss, the position of the phosphorylation site can be determined, as long as there is sufficient residual backbone fragmentation, because neutral loss leaves an unusual residue at the phosphorylation site: phosphoserine becomes dehydroalanine, and phosphothreonine becomes dehydroaminobutyric acid.

Accordingly, in a preferred embodiment of the disclosed method, isolated modified peptides may be further characterized by $MS^3$ (for example LC-$MS^3$, as in a preferred embodiment) analysis; that is, the neutral-loss ions may be subjected to an additional level of MS to give sufficient backbone fragmentation for identification. This process is simpler to implement on ion trap mass spectrometers than on other types of mass spectrometers. As peptides elute from the LC system, a survey MS scan is performed, and MS/MS spectra are collected for the three most abundant ions, if they are above a pre-set intensity threshold and if they have not been recently analyzed by MS/MS already. However, if neutral loss of 49, 32.7, or 24.5 is detected during MS/MS, then before collecting another MS/MS spectrum or another survey MS scan, the instrument first isolates the neutral loss ion, fragments it, and measures the product ion masses. In the case of phosphopeptides, if the neutral-loss ion no longer contains phosphate, it is more likely to fragment like a non-phosphorylated peptide and give a useful product ion spectrum. With certain modifications to the instrument control software, $MS^3$ spectra can be collected in the same data-dependent manner as MS/MS spectra, and the $MS^3$ spectra can be analyzed further with Sequest. See Tomaino and Rush et al. *Abstract ThOE* 3:00, presented at the 50$^{th}$ ASMS Conference on Mass Spectrometry and Allied Topics, Jun. 6, 2002.

Following $MS^3$ analysis, peptides may again be identified using a search program such as Sequest. In the event that a given peptide is unambiguously identified but the program is unable to distinguish between multiple possible phosphorylation sites, the most likely phosphorylation site may be chosen by comparing the sites to the known specificity of the modification-specific antibody used in the isolation. For example, two possible phosphorylation sites (encompassing Ser 585 and Ser 588 of PTN6_HUMAN) were distinguished by noting that the sequence context of one possible site but not the other fits the known specificity of the phospho-(Ser) PKC substrate motif antibody used to isolate the peptide (see Example V).

In cases where peptides comprising multiple modification sites are isolated, it may be difficult to obtain unambiguous assignments because of the high level of neutral loss with very little residual fragmentation along the peptide backbone. At present, for example, multiply-phosphorylated peptides cannot be analyzed effectively by LC-$MS^3$ using the currently available version of Sequest software. The current data-dependent acquisition software isolates and fragments the most abundant neutral-loss ion; for multiply phosphorylated peptides this corresponds to the peptide with one phosphate removed by neutral loss, leaving one or more phosphate groups to undergo neutral loss during $MS^3$. However, the acquisition software is being revised (per personal communication) to recognize multiples of neutral loss and to isolate and fragment the ion with the highest level of neutral loss, even if it is not the most intense product ion. It is expected, therefore, that further analysis of multiply-modified peptides with revised acquisition software will allow the parent proteins and modification sites of some of these peptides to be assigned. Accordingly, the scope of the present invention includes such future revisions and versions of acquisition software, such as Sequest.

Following assignment of a peptide sequence and phosphorylation site to a spectrum, the assignment may be confirmed by establishing that a synthetic peptide with that sequence and phosphorylation site gives the same spectrum. This establishes a formal link between a specific phosphopeptide and its spectrum. This is a simple and convincing way to further evaluate marginal Sequest assignments, for example, or to confirm assignments that are considered especially important.

A simple confirmation method is essential to strategies that attempt to assign phosphorylation sites globally, such as the method of the invention. Neutral loss of phosphate from phosphoserine or phosphothreonine can make it difficult to assign a peptide sequence to an MS/MS spectrum and occasionally assignments will be ambiguous. In contrast to global methods, when analyzing a single phosphorylated protein, e.g., isolated as a stained band by SDS-PAGE, the non-phosphorylated peptides from the protein will be available for analysis and will help to identify the protein, making assignment of phosphopeptides simpler, because the set of possibilities can be restricted to peptides that originate from that identified protein instead of a much larger database of proteins. However, in a global proteomic method, such as the method disclosed herein, where, for example, phosphopeptides are isolated and analyzed separately from non-phosphorylated peptides, often the only peptide from a particular protein will be the isolated phosphopeptide, and unambiguous assignments are likely to be more difficult to achieve. Assignments that are not unambiguous can be confirmed by synthesizing a peptide with the assigned sequence and phosphorylation site and analyzing it by LC-MS/MS or LC-$MS^3$ to determine whether it produces the same spectrum as the biological peptide.

As described above, the tendency of some phosphopeptides to undergo moderate to excessive neutral loss of phosphate can make it difficult to assign a sequence to the spectrum of a particular phosphopeptide. Programs such as Sequest provide a ranked list of assignments for each spectrum. For non-phosphorylated peptides the top-ranked assignment made by Sequest is often correct, but for phosphopeptides the correct assignment may not have the highest rank because of the additional complexities in the spectrum due to neutral loss and the inability of Sequest to recognize and take into account these neutral loss peaks. However a unique feature and advantage to antibody-based isolation methods, such as the present invention, is that the known specificity of the antibody can be used to screen marginal assignments, i.e., assignments that are not top-ranked, to find ones worth pursuing further. That is, antibody-based isolation methods have an inherent advantage over other isolation methods because the antibody's specificity can be used to partially compensate for some of the limitations associated with MS/MS analysis of phosphopeptides.

As discussed above, in practicing the immunoaffinity isolation methods of the invention, a device for isolating modified peptides from the proteinaceous preparation may be coupled directly to a mass spectrometer so that peptides are analyzed as they elute from the immunoaffinity-isolation device, enabling the mass spectrometer to analyze even more complex mixtures of peptides. For example, a liquid chromatography system fractionates complex peptide mixtures into simpler mixtures, which are then analyzed immediately by the mass spectrometer without intervening sample-handling steps. In this manner, the method of the invention may be readily automated, so as to allow the efficient, high-throughput isolation of modified peptides from complex mixtures.

To increase the tolerance for complex samples even further, the liquid chromatography system may be multi-modal, i.e. it can operate in two or more separation modes sequentially. For example, one set of modified peptides may be eluted from an ion-exchange support onto a reversed-phase support, followed by a reversed-phase separation into the mass spectrometer, and then another set of modified peptides may be analyzed by a more potent elution from the ion-exchange support onto the reversed-phase support and a second reversed-phase separation into the mass spectrometer, and so forth, iteratively. See, e.g. Washburn, supra.

It is also contemplated that one dimension of multi-modal liquid chromatography could be immunoaffinity purification, using general modification-specific antibodies to purify post-translationally modified peptides, as described herein. In this sense the immunoaffinity column would resemble a so-called enzyme reactor column, a column of immobilized protein used upstream of a mass spectrometer to catalyze a reaction on the sample to be analyzed. See e.g. Amankwa et al. *Protein Sci.* 4: 113–125 (1995).

Identification of Novel Sites; Antibodies

The immunoaffinity isolation methods of the invention allow the efficient and rapid isolation and identification of peptides comprising protein modification sites from complex mixtures. Modified peptides isolated according to the method of the invention may comprise known modification sites on a particular protein, or may comprise novel sites of modification previously unreported. For example, unknown phosphorylation sites of a particular protein may be identified in accordance with the method of the present invention. Similarly, the methods of the invention may isolate and identify sites whose modification (e.g. phosphorylation) is known, per se, but whose modification in a particular cell, tissue, disease state, etc. is not known. Thus, the disclosed methods enable, in part, the identification of modification sites of particular proteins that are relevant (i.e. the proteins are activated or de-activated) to a particular disease state.

The identification of novel protein modification sites enables the generation of new antibody reagents which are specific for the novel protein site in its phosphorylated form. For example, the identification of a novel phosphorylation site (e.g. a particular phosphoserine site) according to the method of the invention enables the generation of phospho-specific antibodies which bind to that protein only when phosphorylated at the novel site. If a motif-specific, context-independent antibody is employed for the immunoaffinity isolation, novel sites identified will match the specificity of the motif-antibody employed. These modification-specific antibodies against novel sites will be highly useful reagents for the detection of protein modification, as well as for diagnostic or therapeutic uses.

Once a novel modification site is identified, modification-specific antibodies to that site may be generated by standard techniques familiar to those of skill in the art. The antibodies may be polyclonal or monoclonal. Anti-peptide antibodies may be prepared by immunizing an appropriate host with a synthetic phospho-peptide antigen comprising the novel modification site, according to standard methods. See, e.g., ANTIBODIES: A LABORATORY MANUAL, Chapter 5, p. 75–76, Harlow & Lane Eds., Cold Spring Harbor Laboratory (1988); Czernik, *Methods In Enzymology*, 201: 264–283 (1991); Merrifield, *J. Am. Chem. Soc.* 85: 21–49 (1962)). Monoclonal antibodies may be produced in a hybridoma cell line according to the well-known technique of Kohler and Milstein. *Nature* 265: 495–97 (1975); Kohler and Milstein, *Eur. J. Immunol.* 6: 511 (1976); see also, CURRENT PROTOCOLS IN MOLECULAR BIOLOGY, Ausubel et al. Eds. (1989). Motif-specific, context-independent antibodies may also be produced against the novel site identified if the site is a motif conserved among a plurality of different signaling proteins. See Comb et al., WO 00/14536, supra.

Modification-specific antibodies generated against novel sites and/or motifs identified by the immunoaffinity methods of the invention may be screened for epitope and modification-specificity according to standard techniques. See, e.g. Czernik et al., *Methods in Enzymology*, 201: 264–283 (1991). For example, in the case of a novel phosphorylation site, the antibodies (whether polyclonal or monoclonal) may be screened against a phospho and non-phospho peptide library by ELISA to ensure specificity for both the desired antigen (i.e. that epitope including the novel phosphorylation site/residue) and for reactivity only with the phosphorylated form of the antigen. Peptide competition assays may be carried out to confirm lack of reactivity with other non-target protein phosphoepitopes. The antibodies may also be tested by Western blotting against cell preparations containing the parent protein, e.g. cell lines over-expressing that protein, to confirm reactivity with the desired phosphorylated target. Specificity against the desired phosphorylated epitopes may also be examined by construction of parent/target protein mutants lacking phosphorylatable residues at positions outside the desired epitope known to be phosphorylated, or by mutating the desired phospho-epitope and confirming lack of reactivity.

In accordance with the present invention, two novel protein phosphorylation sites were identified by the practice of the disclosed immunoaffinity isolation methods: (i) a novel ubiquitin fusion degradation protein 1 (UFD1) phosphorylation site (Ser335, comprising the sequence GQS*LR) was identified using phospho-(Ser) PKC substrate motif antibody for immunoaffinity isolation of modified peptides from a Jurkat cell extract, and (ii) a novel protein-tyrosine phosphatase 1c (PTN6) phosphorylation site (Ser588, comprising the sequence KGS*LK) was identified using the same PKC substrate motif antibody for immunoaffinity isolation of modified peptides from Jurkat cell extracts (see Example V).

Phospho-specific antibodies that bind either UFD1 or PTN6, respectively, only when phosphorylated at these novel sites can now readily be prepared, according to standard techniques. Synthetic phospho-peptide antigens comprising the UFD1 or PTN6 sequence surrounding and including phospho-Ser335 or Ser588, respectively, may be selected and constructed in accordance with well known techniques, and used as immunogens to produce poly- or mono-clonal antibodies. See, e.g., ANTIBODIES: A LABORATORY MANUAL, supra, Czernik, *Methods In Enzymology*, supra. The phospho- and epitope-specificity of these antibodies may be confirmed as described above.

Accordingly, in a preferred embodiment, the invention also provides an antibody that binds ubiquitin fusion degradation protein 1 (UFD1) only when phosphorylated at serine 335, but does not substantially bind to UFD1 when not phosphorylated at this residue. The UFD1 (pSer335) antibody of the invention also does not substantially bind to proteins other than UFD1, although some limited cross-reactivity may be observed with proteins containing sites highly homologous to the UFD1 phospho-Ser335 site.

In another preferred embodiment, the invention provides an antibody that binds protein-tyrosine phosphatase 1c (PTN6) only when phosphorylated at serine 588, but does not substantially bind to PTN6 when not phosphorylated at this residue. The PTN6 (pSer588) antibody of the invention also does not substantially bind to proteins other than PTN6, although some limited cross-reactivity may be observed with proteins containing sites highly homologous to the PTN6 phospho-Ser588 site.

Profiling and Diagnostic Applications

As noted above, the invention enables the rapid, efficient, and direct isolation of modified peptides from complex mixtures, such as crude cell extracts or biological fluids, without the need for costly and time-consuming pre-purification of desired peptides or proteins. The method makes possible the single-step immunoaffinity isolation of multiple different modified peptides, corresponding to a multitude of different modified proteins and signaling pathways, with a single antibody. Accordingly, the methods disclosed herein are suitable and highly useful for genome-wide (e.g. cell-wide) profiling of activation states, for example. The simplicity of the disclosed method also makes it readily automatable, as only a single immunoaffinity isolation step is required.

Facile isolation of modified peptides aids in the identification and assignment of modification sites in a great variety of different proteins. These protein modifications occur in response to significant events in the life of a cell, and in some cases the modifications provide a potential target for diagnosing or preventing the event. As the genome sequences of various organisms continue to become known, the need to find and assign these modifications in a given organism will become even more pronounced. In a broad context, the invention is useful not only to assign modification sites in well-defined in vitro complexes, but also to generate genome-wide or cell-wide activation/modification profiles, that is, to determine how global protein modification changes within a given cell or tissue in response to environmental changes, such as stress, inflammation, disease, drug treatment, etc.

In contrast to conventional proteomics methods, which focus on how global protein levels change in response to a particular treatment, the present invention focuses on cellular changes in protein modification resulting from a given event, such as disease or treatment. Protein modification, such as phosphorylation and dephosphorylation, serves as a molecular switch for modulating many important biological processes, including cellular transformation and cancer, programmed cell death, cell cycle control, and metabolism. Thus, one advantage offered by the present invention is that it provides a means of focusing on these molecular switching events, which can occur without an accompanying change in the amount of a specific protein in a cell, i.e. a cellular response may be triggered by a change in the modification state of a specific signaling protein, and not by a change in the amount of that protein in the cell.

The immunoaffinity isolation methods of the invention will be useful for the diagnosis of a condition known to be associated with the activation (or de-activation) of a given modification site on a protein. For example, a phosphorylation site on a certain cell signaling protein which is a known marker of a given disease may be isolated (from a clinical tissue or fluid sample) in accordance with the invention to identify the phosphorylation status (i.e. activation status) of the marker in a patient. This marker activation information will assist in the diagnosis of disease and/or identify subjects at risk of disease. Accordingly, in a preferred embodiment of the disclosed method, the modified peptide isolated in step (c) corresponds to a known marker of disease.

The methods of the invention will be useful for profiling protein activation (i.e. modification) states in a target cell or fluid, on a genome-wide, or pathway-wide basis, in response to environmental changes such as disease or drug treatment. For example, biopsy samples may be obtained from cancer patients and analyzed against normal, reference tissue or cells from the same patient. Alternatively, the method will be useful both for discovering modified protein markers for specific types of cancer, and as a diagnostic assay for those cancers, perhaps helping to mark their stage of progression. Accordingly, in one preferred embodiment of the method, the modified peptide(s) characterized in step (d) comprise(s) an unknown modification site of a parent protein. For example, the method may be advantageously employed to identify phosphorylation sites on particular cell signaling proteins that are elevated or reduced in cancerous tissue, as opposed to normal tissue. In a similar manner, the method will be useful to evaluate the cellular effects of a therapeutic drug (i.e. changes in protein modification) to gauge if it is having the desired effect, or to determine when its dosage may induce toxicity. For example, cells or tissue treated with a test drug intended to reduce phosphorylation of a particular protein known to be associated with a certain disease state may be monitored to determine the phosphorylation state of that protein and/or others. The method could also be used to monitor the stages and severity of an infectious disease by monitoring changes in cell-wide modification state during the course of the disease.

Accordingly, in a preferred embodiment, the isolation method of the invention further comprises the step of (e) comparing the modification state of the modified peptide characterized in step (d) with the modification state of a corresponding peptide in a reference sample, thereby to compare protein activation in the proteinaceous preparation with protein activation in the reference sample. In one preferred embodiment, the proteinaceous preparation corresponds to a diseased organism and the reference sample corresponds to a normal organism, whereby comparison of protein activation provides information on activation changes resulting from the disease. In a second preferred embodiment, the proteinaceous preparation is obtained from a tissue biopsy cell or a clinical fluid sample and the reference sample corresponds to a diseased organism, whereby the comparison of protein activation provides information useful for diagnosis of the disease. In a third preferred embodiment, the protein preparation corresponds with an organism or preparation treated with at least one test compound and the reference sample corresponds with an untreated organism or preparation, whereby the comparison of protein activation provides information on activation changes resulting from treatment with the test compound.

In another preferred embodiment, the comparison of protein activation described above identifies the modified peptide characterized in step (d) as corresponding to a parent protein not previously reported as so modified in the disease.

The isolation of modified peptides relevant to a given disease as outlined above may be carried out for virtually any disease in which aberrant signal transduction (i.e. protein activation/modification) is involved or suspected of being involved. In a preferred embodiment of the method, the disease is cancer. Similarly, the modified peptide isolation may be employed to monitor the effects of virtually any test compound or drug on protein modification. In a preferred embodiment, the test compound comprises a cancer therapeutic. In a particularly preferred embodiment, the test compound comprises a kinase inhibitor, such as STI-571 (Gleevac®), an inhibitor of AbI kinase for the treatment of leukemia.

In the profiling and diagnostic applications described here, the proteinaceous preparation from which modified peptides will be isolated may correspond, for example, to a diseased cell or fluid, tissue biopsy cell or clinical fluid sample, or test cell treated with a test drug or fluid from an organism treated with a test drug, and the reference sample may correspond to a normal cell or fluid, diseased cell or fluid, or untreated cell or fluid from an untreated organism, whereby the profiling provides information useful in changes in, e.g. modification state, resulting from disease or drug treatment, or diagnosis of disease. Alternatively, the reference sample may correspond to a state of aberrant signaling (i.e. a diseased sample) and the proteinaceous preparation may correspond to a normal organism, for example, a patient being tested for the presence of a marker of disease or susceptibility to disease.

The isolation and profiling methods of the invention will be particularly useful in the high-throughput identification of modification states on known or unknown proteins on a genome-wide basis, so as to provide a link between genomic and proteomic information and actual disease states. The method is readily automatable, and thus, for example, may be advantageously employed by pharmaceutical companies wishing to efficiently and rapidly identify markers of disease for diagnostic or therapeutic applications.

Quantification of Isolated Peptides

In one preferred embodiment the method may employ additional procedures to allow quantification of modified peptides prepared according to the method of the invention. For example, in SILAC (stable isotope labeling by amino acids in cell culture) cell cultures are grown in culture media that has been depleted of specific amino acids, e.g., arginine and lysine, and then supplemented with these amino acids in "normal isotope" or stable, "heavy isotope" forms. See, e.g. Ong et al., *Mol. Cell. Proteomics* 5: 376–86 (2002). Cells grown in heavy-isotope media can be treated with a drug candidate that is expected to inhibit one specific protein kinase, while the same cells grown in normal-isotope media are left untreated. When these samples are prepared for analysis by the method of the invention, the cells are harvested and mixed at a one-to-one ratio. In all subsequent steps these two admixed samples are handled as one sample, so any mass spectrometry intensity differences between the samples can be attributed only to drug treatment and not to sample handling or run-to-run analysis variations. Differences in the samples are traced to the drug-treated or untreated sample on the basis of the presence or absence, respectively, of the heavy-isotope in the analyzed peptides during mass spectrometry. SILAC provides relative quantification and is considered to be a promising key method for discovering biomarkers by comparative, quantitative mass spectrometry. An alternative method for quantification is Aqua (absolute quantification). See Gerber, Rush et al. *Proc. Natl. Acad. Sci. U.S.A.* 100: 6940–5 (2003). In this method, the modified peptide to be quantified is synthesized as a heavy-isotope peptide, which can then serve as an internal quantification standard. A known amount of the heavy-isotope peptide is added to the sample prior to digestion with a protease. Because the heavy-isotope peptide standard is chemically identical to the biologically derived peptide to be quantified, they will co-purify by the method of the invention and will be mass analyzed at the same time. By multiplying the known amount of heavy-isotope peptide standard by the measured ratio of biological peptide to peptide standard, the absolute amount of biological peptide in the sample is determined. In contrast to the SILAC method, the Aqua strategy provides absolute quantification and can be used with a wide variety of sample types other than cell cultures. The Aqua method is a preferred embodiment of the method of the invention when it is desirable to quantify a limited number, e.g., 1 to 60, of modified peptides such as in the development of quantitative assays based on mass spectrometry. A key element of the Aqua strategy is identifying peptides that can be measured quantitatively because it is known they can be detected when analyzed by mass spectrometry, in contrast to peptides that are selected by a de novo process and that expected to be present but cannot be detected. In a preferred embodiment, the method of the invention is first used to determine the peptides that are suitable for measurement by the Aqua strategy and then later used as part of an Aqua-based mass spectrometry quantification assay. A third method for quantification is based on chemical modification of peptides with normal-isotope and heavy-isotope chemical modification reagents, e.g., reagents that react with peptide amino groups or carboxylic acid groups. See, e.g., Zhang et al. *Nat Biotechnol.* 21: 660–6 (2003). This follows the same overall strategy as the SILAC method, except samples are mixed after the chemical modification step and samples other than cell cultures can be analyzed.

The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE I

A. Isolation of Phosphotyrosine-Containing Peptides from a Peptide Mixture

To establish that phosphopeptides can specifically be purified from complex mixtures without contamination from nonphosphorylated peptides, the method of the invention was used to isolate phosphotyrosine (p-Tyr)-containing peptides from a mixture of phosphorylated and nonphosphorylated synthetic peptides. A phosphotyrosine peptide mix comprising 5 phosphotyrosine-containing peptides and their 5 nonphosphorylated partner peptides was prepared (Table 1); note the nonphosphorylated peptides have the same sequences as the phosphorylated peptides but are not phosphorylated, that is, they contain tyrosine instead of phosphotyrosine. Peptides were synthesized by Fmoc chemistry on a Rainin/Protein Technologies Symphony peptide synthesis instrument and using Fmoc-Tyr(PO(OBzl)OH)—OH as the phosphotyrosine monomer. See Perich, *Lett. Pept. Sci.* 6: 91 (1999). The peptide mixture covers a broad mass range designed to resemble a protein digest.

TABLE 1

Components of the Phosphotyrosine Peptide Mix

| Sequence | Calculated Protonated Peptide Mass |
|---|---|
| KIEKIGEGTY*GVVYKGRHK (SEQ ID NO: 1) | 2,242.174 |
| KIEKIGEGTYGVVYKGRHK (SEQ ID NO: 2) | 2,162.208 |
| RLIEDNEY*TARQGAKC (SEQ ID NO: 3) | 1,946.879 |
| RLIEDNEYTARQGAKC (SEQ ID NO: 4) | 1,866.912 |

TABLE 1-continued

Components of the Phosphotyrosine Peptide Mix

| Sequence | Calculated Protonated Peptide Mass |
|---|---|
| LQERRKY*LKHRC (SEQ ID NO: 5) | 1,709.878 |
| LQERRKYLKHRC (SEQ ID NO: 6) | 1,629.911 |
| RQGKDY*VGAIPVDC (SEQ ID NO: 7) | 1,600.719 |
| RQGKDYVGAIPVDC SEQ ID NO: 8 | 1,520.752 |
| GKDGRGY*VPATC (SEQ ID NO: 9) | 1,303.550 |
| GKDGRGYVPATC (SEQ ID NO: 10) | 1,223.583 |

Y* = phosphotyrosine
Y = tyrosine

The MALDI-TOF mass spectrum of the mixture before immunoaffinity purification is shown in FIG. 2. Peaks labeled with a star correspond to phosphorylated peptides, and peaks labeled with open circles correspond to the nonphosphorylated partner peptides.

P-Tyr-containing peptides were specifically isolated from the diverse peptide mixture by contacting the phosphotyrosine peptide mix (46 nmol total) with a phosphotyrosine monoclonal antibody P-Tyr-100 immobilized to agarose resin (Cell Signaling Technology, Inc., product number 9419) (100 µl). The antibody was incubated with the peptides as a slurry, in a batch purification format. The slurry was left at room temperature for 10 minutes and on ice for 1 hour. The unbound peptides were removed by centrifugation through a plastic frit, and the retained antibody-resin was washed extensively (twice with 1 ml of ice-cold phosphate buffered saline containing 0.5% NP-40, twice with 1 ml of ice-cold phosphate buffered saline, and once with water). To elute bound phosphopeptides, the antibody-resin was resuspended in 400 µl 30% acetic acid, left at room temperature for 10 minutes, and centrifuged. The eluted peptide fraction was dried and resuspended in 80 µl water (the volume of the phosphotyrosine peptide mix before treatment with antibody-resin), and a 1 µl aliquot was diluted and analyzed by MALDI-TOF mass spectrometry, as described above (FIG. 3). FIG. 4 shows the mass spectrum of the phosphotyrosine peptide mix before (top panel) and after (bottom panel) immunoaffinity purification. Note that the fraction eluted from the antibody-resin contains all 5 phosphopeptides but none of the nonphosphorylated peptide partners. Accordingly, the method of the invention specifically isolates all desired phosphopeptides containing a phosphotyrosine, regardless of the different sequences in which the phosphotyrosine occurs, from a complex mixture of phosphorylated and nonphosphorylated peptides.

B. Isolation of Phosphothreonine-Containing Peptides from a Peptide Mixture

The method of the invention was further demonstrated using a second general protein modification antibody, a phosphothreonine polyclonal antibody P-Thr-polyclonal to purify peptides containing phosphothreonine from a mixture of phosphorylated and nonphosphorylated synthetic peptides. The mixture consists of 4 synthetic peptides: 2 phosphothreonine-containing peptides and their 2 nonphosphorylated partner peptides (see Table 2). The MALDI-TOF mass spectrum, obtained as described above, of the phosphothreonine peptide mix before immunoaffinity purification according to the invention is shown in FIG. 5.

TABLE 2

Components of the Phosphothreonine Peptide Mix

| Sequence | Calculated Protonated Peptide Mass |
|---|---|
| DTQIKRNT*FVGTPFC (SEQ ID NO: 11) | 1,806.825 |
| DTQIKRNTFVGTPFC (SEQ ID NO: 12) | 1,726.859 |
| CKEGLGPGDTTST*F (SEQ ID NO: 13) | 1,491.620 |
| CKEGLGPGDTTSTF (SEQ ID NO: 14) | 1,411.653 |

T* = phosphothreonine,
T = threonine

A P-Thr-polyclonal antibody (Cell Signaling Technology, Inc., product number 9381) was linked to agarose resin using a hydrazide chemistry (the same chemistry used to produce the P-Tyr-100 agarose resin used in Example 1A above), using a commercially available crosslinking kit (BiORad Affi-Gel HZ Immunoaffinity Kit, product number 153-6060) and following the manufacturer's instructions. Each milliliter of resin was reacted with 1 milligram of antibody. P-Thr-containing phosphopeptides were specifically isolated from this mixture by contacting the phosphothreonine peptide mix (20 µmol total) with this antibody-resin (100 µl), and incubating the resin and peptides at 4° C. overnight. The resin was recovered and washed, and the bound peptides were eluted, processed, and analyzed as described above. FIG. 6 shows the MALDI-TOF mass spectra of the unbound and bound peptide fractions. The unbound fraction contains all 4 peptides, including the phosphopeptides; under the particular conditions utilized, which were not optimized, some of each isolated phosphopeptide has passed through the column. The bound fraction contains both phosphopeptides but does not contain the nonphosphorylated peptide partners. Accordingly, the method of the invention selectively isolates all desired phosphopeptides containing a phosphothreonine, regardless of the different sequences in which the phosphothreonine occurs, from a mixture of phosphorylated and nonphosphorylated peptides.

C. Isolation of Phosphotyrosine-Containing Peptides from Low-Level Samples

The isolation of modified peptides from low-level samples (i.e. where the amount of each modified peptide is about 1 mol or less) according to the method of the invention was demonstrated using low-picomole amounts of phosphotyrosine peptides from the 10-peptide mix and the immobilized phosphotyrosine antibody P-Tyr-100, as described above in Part IA. P-Tyr-containing phosphopeptides were isolated from this complex mixture, by contacting the 1.0-peptide mix (24 pmol total) with the P-Tyr-100 antibody-resin (CST product number 9419) (10 µl). The peptide mixture contained 100 ng BSA to reduce non-specific peptide loss through adsorption. The resin was recovered and washed extensively (twice with 0.5 ml PBS containing 0.5% NP40, twice with 0.5 ml PBS, and five times with 0.5 ml water). Phosphopeptides bound to the antibody-resin were eluted by washing the resin three times with 5 μl 0.1 M glycine, pH 2.3. The three elutions were combined, and an aliquot was desalted with a ZipTip device (Millipore Corp., part number ZTC18S096), since glycine interferes with MALDI-TOF mass analysis.

FIG. 7 shows the mass spectrum for the low-level 10-peptide mix before (top panel) and after (third panel) immunoaffinity purification according to the method of the invention. Peaks labeled with a star correspond to phosphorylated peptides, and peaks labeled with circles correspond to the nonphosphorylated partner peptides. All 5 phosphopeptides, although present at low (picomole) levels, were bound and eluted from the antibody-resin (third panel). Of the 10 peptides in the mix, only 3 were detected in the unbound fraction (second panel), and they were all nonphosphorylated peptides. The bound peptide fraction was neutralized, treated with calf intestinal alkaline phosphatase, an enzyme that can remove phosphate from phosphopeptides, and re-analyzed to confirm the phosphopeptide assignments (FIG. 7, bottom panel). As expected, the phosphopeptides were completely dephosphorylated to produce ions with masses 80 lower than the phosphopeptides. This was particularly helpful in assigning the peaks at 1,869 and 1,523 to phosphopeptide synthesis artifacts and the peaks at 1,867 and 1,521 to non-phosphopeptides. Accordingly, the method of the invention selectively isolates all desired phosphopeptides, even at low levels, that contain a phosphotyrosine, regardless of the different sequences in which the phosphotyrosine occurs, from a low-level mixture of phosphorylated and nonphosphorylated peptides.

D. Isolation of Akt Substrate Phosphopeptides from a Peptide Mixture

The method of the invention was further demonstrated using a motif-specific, context-independent polyclonal antibody, phospho-(Ser/Thr) Akt substrate antibody, to purify phosphopeptides containing the phospho-Akt substrate motif from a mixture of phosphorylated and nonphosphorylated synthetic peptides. The Akt protein kinase plays a central role in cell growth (Marte and Downward, *Trends Biochem. Sci.* 22: 355–358 (1997)), angiogenesis (Jiang et al., *Proc. Natl. Acad. Sci. USA* 97: 1749–1753 (2000)), and transcriptional regulation (Scheid and Woodgett, *Curr. Biol.* 10: R191–194 (2000)). The Akt protein kinase is able to phosphorylate protein substrates at threonine or serine residues when the target residue occurs within the consensus sequence motif RXRXX(T/S), where R is arginine, X is any amino acid, and T/S indicates the target threonine or serine.

Phospho-(Ser/Thr) Akt substrate polyclonal antibody (Cell Signaling Technology, Inc., product number 9611) recognizes a plurality of different phosphorylated proteins that contain the consensus sequence motif when phosphorylated, but does not recognize the analogous unphosphorylated motif. The specificity of the phospho-(Ser/Thr) Akt substrate antibody is that it binds preferentially to proteins and peptides that contain phosphothreonine or phosphoserine preceded by lysine or arginine at positions −5 and −3, i.e., (K/R)X(K/R)XX(T*/S*) (SEQ ID NO: 15), in a manner substantially independent of the surrounding amino acid sequence (i.e. the context of the motif). It is now demonstrated here that this antibody can be used to purify peptides that contain the phosphorylated Akt consensus substrate motif.

Akt motif-containing phosphopeptides were selectively isolated from a mixture of phosphorylated and nonphosphorylated synthetic peptides according to the method of the invention. The mixture consisted of 8 synthetic peptides: 3 phosphothreonine-containing peptides, 1 phosphoserine-containing peptide, and their 4 nonphosphorylated partner peptides (Table 3). The phospho-Akt substrate consensus sequence is present in all 4 phosphopeptides in this mixture, and it is known from ELISA that these phosphopeptides are recognized by and can bind to the phospho-Akt substrate antibody.

TABLE 3

Components of the Phospho-Akt Substrate Peptide Mix

| Sequence | Calculated Protonated Peptide Mass |
|---|---|
| CSPRRRAAS*MDNNSKFA (SEQ ID NO: 16) | 1,989.889 |
| CSPRRRAASMDNNSKFA (SEQ ID NO: 17) | 1,909.923 |
| CLKDRQGT*HKDAEIL (SEQ ID NO: 18) | 1,805.872 |
| SRPRSCT*WPLPREI (SEQ ID NO: 19) | 1,777.856 |
| CRSLT*GKPKLFIIQA (SEQ ID NO: 20) | 1,754.938 |
| CLKDRQGTHKDAEIL (SEQ ID NO: 21) | 1,725.906 |
| SRPRSCTWPLPREI (SEQ ID NO: 22) | 1,696.906 |
| CRSLTGKPKLFIIQA (SEQ ID NO: 23) | 1,674.972 |

Phosphopeptides were isolated from this peptide mixture by contacting the phospho-Akt substrate peptide mix (5 pmol each peptide) with phospho-(Ser/Thr) Akt substrate antibody immobilized to agarose resin (Cell Signaling Technology, Inc., part number 9619) (20 μl, 2 μg/μl). The antibody was incubated with the peptides as a slurry at 4° C. for 2 hours. Unbound peptides were removed by centrifugation, and the antibody-resin was washed extensively (two times with 0.5 ml ice-cold PBS containing 0.5% NP-40, two times with 0.5 ml ice-cold PBS, and three times with 0.5 ml ice-cold water). Bound peptides were eluted with three 10 aliquots of 0.1 M glycine, pH 2.3. A 5 μl portion of the fraction containing bound and eluted peptides was desalted and concentrated with a reversed-phase ZipTip microcolumn before analysis by MALDI-TOF mass spectrometry, as described above.

FIG. 8 shows the mass spectra of the phospho-Akt substrate peptide mix before (top panel) and after (bottom panel) immunoaffinity purification. Peaks labeled with a star correspond to phosphopeptides, peaks labeled with an open circle correspond to nonphosphorylated peptides, and peaks labeled with a square are phosphopeptides that have undergone metastable decomposition and neutral-loss of phosphate (discussed in Example V below). The fraction of peptides that bound to and eluted from the immobilized antibody (bottom panel) contains all 4 phosphopeptides but does not contain the nonphosphorylated partner peptides. Accordingly, the method of the invention selectively isolates all peptides in this synthetic peptide mixture that contain the phospho-Akt substrate motif, whether they contain phosphothreonine or phosphoserine residues. As desired, peptides that contain the nonphosphorylated consensus motif are not isolated.

E. Isolation of 14-3-3 Binding Motif #1 Phosphopeptides from a Peptide Mixture

The method of the invention was further exemplified using a second motif-specific, context-independent monoclonal antibody, phospho-(Ser) 14-3-3 binding motif antibody, to purify phosphopeptides containing the 14-3-3 binding motif from a mixture of phosphorylated and nonphosphorylated synthetic peptides. The 14-3-3 proteins regulate several biological processes through phosphorylation-dependent protein-protein interactions (Muslin et al., Cell 84, 889–897 (1996)). Nearly all binding partners of 14-3-3 proteins contain at least one of two different phosphoserine-containing consensus sequences (Yaffe et al. Cell 91, 961–971 (1997)). One consensus sequence, motif #1, is (R/K)SXS*XP, where R/K indicates arginine or lysine, S is serine, X is any amino acid, S* is phosphoserine, and P is proline.

Phospho-(Ser) 14-3-3 binding motif monoclonal antibody (4E2) (Cell Signaling Technology, Inc., product number 9606) is a motif-specific antibody that recognizes phosphopeptides that contain this consensus binding motif #1. The 14-3-3 binding motif antibody is highly specific for peptides and proteins that contain this motif (phosphoserine surrounded by proline at the +2 position and arginine or lysine at the −3 position, i.e., (K/R)XXS*XP (SEQ ID NO: 24). Recognition is specific for the phosphorylated form of the motif and is substantially independent of the surrounding amino acid sequence (i.e. the context of the motif). This antibody weakly cross-reacts with analogous sequences containing phosphothreonine instead of phosphoserine in this motif.

To identify other proteins that bind to 14-3-3 proteins or to profile known binding partners on a genome-wide (cell-wide) basis, immobilized 14-3-3 binding motif antibody may be employed to immunoaffinity purify phosphopeptides from a proteinaceous preparation in accordance with the method of the invention. To demonstrate the feasibility of this, this antibody was first employed to selectively isolate phosphopeptides from a mixture of phosphorylated and nonphosphorylated synthetic peptides when the phosphopeptides contain motif sequences that match the antibody's known specificity. The mixture consisted of 13 synthetic peptides (Table 4). Four peptides in the mixture contained sequences that match the antibody's known specificity, 3 with phosphoserine (SEQ ID NOs: 26, 28, 29) and 1 with phosphothreonine (SEQ ID NO: 27). It is known by ELISA that these three phosphoserine-containing peptides are recognized by and can bind to the 14-3-3 binding motif #1 antibody. The peptide mixture contained 9 other peptides that should not bind to 14-3-3 binding motif antibody: 2 phosphotyrosine-containing peptides, 2 phospho-Akt substrate motif peptides, and 5 nonphosphorylated partner peptides.

TABLE 4

Components of the 14-3-3 Binding Motif Peptide Mix

| Sequence | Calculated Protonated Peptide Mass |
|---|---|
| CSPRRRAAS*MDNNSKFA (SEQ ID NO: 25) | 1,989.889 |
| CSPRRRAASMDNNSKFA (SEQ ID NO: 26) | 1,909.923 |
| FRGRSRS*APPNLWAC (SEQ ID NO: 27) | 1,797.836 |
| SRPRSCT*WPLPREI (SEQ ID NO: 28) | 1,777.856 |
| TRSRHSS*YPAGTEEC (SEQ ID NO: 29) | 1,760.705 |
| CAEYLRSIS*LPVPVL (SEQ ID NO: 30) | 1,738.896 |
| LQERRKY*LKHRC (SEQ ID NO: 31) | 1,709.878 |
| SRPRSCTWPLPREI (SEQ ID NO: 32) | 1,696.906 |
| TRSRHSSYPAGTEEC (SEQ ID NO: 33) | 1,680.739 |
| CAEYLRSISLPVPVL (SEQ ID NO: 34) | 1,658.929 |
| MSGRPRTTS*FAESC (SEQ ID NO: 35) | 1,609.649 |
| RQGKDY*VGAIPVDC (SEQ ID NO: 36) | 1,600.719 |
| RQGKDYVGAIPVDC (SEQ ID NO: 37) | 1,520.752 |

A 14-3-3 binding motif #1 antibody (Cell Signaling Technology, Inc., product number 9606) was linked to agarose resin using a hydrazide chemistry (the same chemistry used to produce the P-Tyr-100 agarose resin used in Example 1A above), using a commercially available crosslinking kit (BiORad Affi-Gel HZ Immunoaffinity Kit, product number 153-6060) and following the manufacturer's instructions. Each milliliter of resin was reacted with 1 milligram of antibody. Phosphopeptides were selectively isolated from the 14-3-3 binding motif peptide mixture by contacting the peptide mix (10 pmol each peptide) with this antibody-resin (10 μl, 1 μg/μl). The antibody was incubated with the peptides as a slurry at room temperature for 1 hour and 4° C. for 1 hour. Unbound peptides were removed by centrifugation, and the antibody-resin was washed extensively (twice with 1 ml ice-cold PBS and once with 1 ml ice-cold water). Bound peptides were eluted with one 30 μl aliquot of 0.1 M glycine, pH 2.0. A 9 μl portion of the eluted peptides was desalted and concentrated with a reversed-phase ZipTip microcolumn before analysis by MALDI-TOF mass spectrometry, as described above.

The mass spectra of the peptide mix before (top panel) and after (bottom panel) immunoaffinity purification are shown in FIG. 9. Peaks labeled with a star correspond to phosphopeptides, and peaks labeled with an open circle correspond to nonphosphorylated peptides. Peaks labeled with filled stars are phosphopeptides that are not expected to bind to the 14-3-3 binding motif antibody because their sequences do not fit the antibody's known specificity. Of the four phosphopeptides in the mixture that contain the 14-3-3 binding motif, three were isolated by the 14-3-3 binding motif antibody, and they correspond to the major peaks in the fraction of peptides that bound to and eluted from the immobilized antibody (FIG. 9, bottom panel). One 14-3-3 binding motif phosphopeptide was not isolated (SEQ ID NO: 29, calculated protonated peptide mass of 1,738.9), but it also could not be detected in the untreated peptide mix, i.e. it may be a poorly ionizing peptide. The phosphothreonine-containing peptide, which contains a slightly variant motif (phosphothreonine in place of phosphoserine), was also isolated (SEQ ID NO: 27, calculated protonated peptide mass of 1,777.8); it was, in fact, expected to cross-react weakly with the antibody. Two peptides that do not contain sequences that match the antibody's specificity were isolated, one was a phosphopeptide containing the phospho-Akt substrate motif (SEQ ID NO: 35, calculated protonated peptide mass of 1,608.6) and the other was unphosphorylated (SEQ ID NO: 25, calculated protonated peptide mass of 1,910.9). Several peaks in the bound and eluted fraction (1,941, 1,770, 1,642, 1,526) are also present in the bound and eluted fraction of a negative control, antibody-resin treated with buffer instead of peptide mixtures. These artifactual peaks appear to originate from the antibody-resin preparation and can probably be avoided by manufacturing a new lot of antibody-resin from highly purified antibody or by pre-eluting the antibody-resin before applying peptide mixtures.

This result further establishes the generality of the method of the invention by showing that desired phosphopeptides can be isolated/enriched by immunoaffinity purification, as described herein. As previously discussed, in certain cases, as here, some peptides that contain the target sequence motif may not be isolated, and/or other peptides that do not contain the target motif may be inadvertently or artifactually purified, for reasons that are unclear. Nevertheless, the completeness and specificity of the disclosed method represents a substantial advance over alternative phosphopeptide purification methods. As previously described, it is anticipated that, in cases where undesired peptides lacking the target motif are co-isolated along with desired peptides, the former may be avoided by increasing the number or stringency of the resin washes to remove non-specifically bound peptides.

EXAMPLE II

A. Isolation of Phosphotyrosine-Containing and Phospho-Akt Substrate Peptide Subsets from a Digested Crude Cell Extract Example I demonstrates that several phosphorylation-specific antibodies can be employed in the method of the invention to selectively separate desired phosphopeptides from non-phosphopeptides. The antibodies may be general modification-specific antibodies or motif-specific, context-independent antibodies that recognize a short non-unique motif comprising several invariant residues, which motif is present on a plurality of different peptides or proteins within a genome. As shown in Example I, the antibodies can distinguish phosphopeptides from non-phosphopeptides even when the only difference between the peptides is the presence or absence of a phosphate group. In the present Example, it is shown that desired phosphopeptides may be selectively isolated by the method of the invention from a complex mixture containing phosphopeptides of different types. The method of the invention isolates the phosphopeptide subset that would be expected on the basis of the antibody's specificity. It is also shown that the results obtained by applying the method to crude cell extracts closely resemble the results obtained by applying the method to well-defined synthetic peptide mixtures.

The exemplary preparation for the isolation described herein was composed of a digested crude cell extract to which the phosphotyrosine peptide mix and the phospho-Akt substrate peptide mix have been added. The crude cell extract was made from 3T3 mouse fibroblast cells that had been stably transfected to express active Akt protein kinase constituitively and that had been treated with 50 ng/ml platelet-derived growth factor (PDGF) for 15 minutes. The cells were washed, harvested, and lysed by sonication, proteins in the lysate were denatured, and the lysate was cleared by centrifugation. The extract was then digested to peptides with endoproteinase Glu-C immobilized to F7m, a polyvinyl matrix bead (MoBiTec, part number P5101), and the immobilized Glu-C was removed by centrifugation. The digested extract was treated with phospho-(Ser/Thr) Akt consensus substrate motif antibody (Cell Signaling Technology, Inc., product number 9611) to remove endogenous peptides recognized by this antibody.

This depleted digested extract was mixed with the phosphotyrosine peptide mix (Table 1) and the phospho-Akt substrate peptide mix (Table 3), so that each peptide was present at a concentration of 10 pmol/ml and the background of peptides from the digested extract was 250 µg/ml. This peptide-extract mixture (1 ml) was treated with either immobilized P-Tyr-100 antibody (Cell Signaling Technology, Inc., part number 9419) or immobilized phospho-Akt substrate antibody (20 µl, 2 µg/µl). After 2 hours at 4° C., each antibody-resin was collected by centrifugation and extensively washed (three times with 1 ml ice-cold PBS and two times with 1 ml ice-cold water). Bound peptides were then eluted with two 15 µl aliquots of 0.1 M glycine, pH 2.3. Before analysis by MALDI-TOF mass spectrometry, as described above, a 9 µl portion of the fraction containing bound and eluted peptides was desalted and concentrated with a reversed-phase ZipTip microcolumn.

For P-Tyr-100 antibody, a general modification-specific antibody, the spectrum shows that the antibody isolated 3 of the 5 phosphotyrosine peptides but none of the 4 phospho-Akt substrate phosphopeptides, which do not contain phosphotyrosine, and none of the 9 non-phosphopeptides, as expected due to the antibody's specificity (FIG. 10, top panel). Peaks labeled with a star correspond to phosphopeptides, and peaks labeled with an open circle correspond to nonphosphorylated peptides. Comparison to FIG. 4 shows the 2 phosphotyrosine-containing peptides that were not identified from the peptide-extract mixture gave low signals from a relatively simple mixture of synthetic peptides. These peptides may ionize poorly when other peptides are present because they poorly compete for protons.

For the phospho-Akt substrate antibody, a motif-specific, context-independent antibody, the spectrum shows the antibody isolated 3 of the 4 phosphopeptides from the phospho-Akt substrate peptide mix but none of the 5 phosphotyrosine peptides (FIG. 11, top panel). Comparison to FIG. 8 shows that the single phospho-Akt substrate peptide that was not identified from the peptide-extract mixture gave low signals from a synthetic peptide mix.

The phosphopeptide assignments shown in FIGS. 10 and 11 were confirmed by treating a portion of the bound peptide fraction with calf-intestinal phosphatase, which can remove phosphate from phosphopeptides. As expected, most assigned phosphopeptides were dephosphorylated to produce ions with masses 80 lower than the phosphopeptides (FIGS. 10 and 11, bottom panels). Accordingly, desired phosphopeptides may be selectively isolated from a complex mixture according to the method of the invention.

B. Isolation of Phosphopeptides Containing the 14-3-3 Binding Motif from a Digested Crude Cell Extract As another example confirming that results obtained with crude cell extracts closely resemble the results obtained with well-defined synthetic peptide mixtures, the method of the invention was employed to isolate 14-3-3 binding motif-containing phosphopeptides from a complex mixture comprising a cell extract and a mixture of synthetic peptides.

The exemplary preparation for the isolation described herein was composed of a digested crude cell extract to which the 14-3-3 binding motif #1 peptide mix (Table 4) has been added. An endoproteinase Glu-C-digested crude cell extract was prepared from 3T3 mouse fibroblast cells stably transfected to express active Akt protein kinase constitutively, as described in Example II(A) above. This digested extract was mixed with the 14-3-3 binding motif peptide mix (Table 4), so that each peptide was present at a concentration of 10 pmol/ml and the background of peptides from the digested extract was 0.5 mg/ml.

Immobilized 14-3-3 binding motif antibody was prepared by mixing 1 mg of 14-3-3 binding motif antibody and 0.1 ml of protein A agarose resin (Roche, product number 1 134 515) overnight at 4° C. Unbound antibody was removed by washing the resin three times with cold PBS. The amount of antibody bound to protein A agarose was shown to be 4 mg antibody/ml resin by measuring the absorbance at 280 nm of the antibody solution before and after immobilization.

The peptide-extract mixture (1 ml) was treated with immobilized 14-3-3 binding motif #1 antibody (20 µl, 1 µg/µl). After 2 hours at 4° C., the antibody resin was collected by centrifugation and extensively washed (twice with 1 ml ice-cold PBS and once with 1 ml ice-cold water). Bound peptides were then eluted with one 30 µl aliquot of 0.1% trifluoroacetic acid. Before analysis by MALDI-TOF mass spectrometry, as described above, a 9 µl portion of the fraction containing bound and eluted peptides was desalted and concentrated with a reversed-phase ZipTip microcolumn.

FIG. 12 shows the peptides that were bound and eluted from the 14-3-3 antibody-resin. Peaks labeled with a star correspond to phosphopeptides, and peaks labeled with an open circle correspond to nonphosphorylated peptides. Comparison of FIG. 12 and FIG. 9 shows the method isolated the same four 14-3-3 motif phosphopeptides from the synthetic peptide mix, even when the mixture was diluted into a large background of potentially interfering, non-binding peptides from a digested cell extract. Accordingly, desired phosphopeptides may be selectively isolated from a complex mixture according to the method of the invention.

EXAMPLE III

Isolation of Phosphotyrosine-Containing Peptides from an Extract of Cells

Overexpressing Epidermal Growth Factor Receptor

The selective isolation of modified peptides from a complex mixture according to the method of the invention was further demonstrated using a digested whole cell extract and a general phosphotyrosine antibody to isolate known phosphopeptides. A model system, the A431 epidermoid carcinoma cell line overexpressing the human epidermal growth factor receptor (EGFR), was selected since the modification (phosphorylation) of sites on this protein is well-studied. Activation of EGFR family members is associated with many tumors. Five sites of in vivo autophosphorylation have been identified in EGFR: three major sites (Tyr-1068, Tyr-1148, and Tyr-1173) and two minor sites (Tyr-992 and Tyr-1086) (Downward et al., *J. Biol. Chem.* 260: 14538–546 (1985); Hsuan et al., *Biochem. J.* 259: 519–27 (1989); Margolis et al., *EMBO J.* 9: 4375–380 (1990); Walton et al., *J. Biol. Chem.* 265: 1750–54 (1990)). EGFR is the major phosphorylated protein expected to be expressed in this cell line.

A cell preparation was obtained as follows: A431 cells were treated with 20 ng/ml EGF for 5 minutes and then washed and harvested. The cells were lysed by sonication, proteins in the lysate were denatured, and the lysate was cleared by centrifugation. The cell extract was analyzed by SDS-PAGE and Western blotting to show the level of phosphorylated EGFR (FIG. 13). Compared to untreated cells (FIG. 13, lane 1), the major protein recognized by P-Tyr-100 antibody in EGF-treated cells is EGFR (lane 2). Proteins in the extract supernatant were digested to peptides with trypsin immobilized to POROS resin (Applied Biosystems, part number 2-3127-00), and the immobilized trypsin was removed by centrifugation.

To selectively isolate phosphotyrosine-containing peptides from the complex mixture of peptides contained in the proteinaceous preparation, the trypsin-digested crude extract (about 2.5 mg protein/mL) was contacted with an immobilized general tyrosine modification antibody, P-Tyr-100 antibody-resin (Cell Signaling Technology, Inc., product number 9419) (20 µl). The slurry was incubated and processed as described above, except that the first wash was with 0.5 ml PBS containing 0.1% Tween 20. FIG. 14 (top panel) shows the mass spectrum for the bound peptide fraction from this complex mixture (digest). Peaks labeled with a star correspond to two known phosphotyrosine sites in EGF receptor: the protonated tryptic peptide containing pTyr-1148 has an expected mass of 2,316.0, and the peptide containing pTyr-1086 has an expected mass of 2,479.2. Note that these EGF receptor peptides were expected to be the major phosphotyrosine peptides in the bound fraction, because the cell line overexpresses the EGF receptor.

To confirm these assignments, the isolated (i.e. bound) peptide fraction was treated with a phosphatase enzyme, as described above, and the treated fraction re-analyzed by MALDI-TOF mass spectrometry, as described above (FIG. 14, bottom panel). As expected, these two phosphopeptides were completely dephosphorylated to produce new ions with masses 80 lower than the phosphopeptides, corresponding to the removal of one phosphate group from each peptide. Accordingly, the method of the invention selectively isolates modified peptides, e.g. those containing phosphotyrosine, from a complex mixture that is present in a proteinaceous preparation (digested crude cell extract). Similar isolations may be carried out for any desired proteinaceous preparation using a desired, immobilized modification-specific antibody.

EXAMPLE IV

Isolation of Phosphotyrosine-Containing Peptides from an Extract of Cells Expressing Activated Src Protein Kinase or Activated Abl Protein Kinase To demonstrate that the set of phosphopeptides isolated by the general phosphotyrosine antibody is a property of the cell extract, the method of the invention was applied to a digested whole cell extract different from the one used in Example III. Here, the exemplary system is 3T3 mouse fibroblast cells stably transfected to express active Src protein kinase constituitively. The Src family of protein kinases is important in the regulation of cell growth and differentiation (Thomas and Brugge, *Annu. Rev. Cell. Dev. Biol.* 13, 513–609 (1997)). Src protein kinase participates in many different signaling pathways and can affect diverse biological processes. Src is known to phosphorylate its target proteins on Tyr residues, i.e., it is a tyrosine-specific kinase.

A digested cell extract was prepared by harvesting 3T3 cells expressing Src protein kinase. The cells were lysed by sonication, proteins in the lysate were denatured, and the lysate was cleared by centrifugation. To show that activated Src protein kinase had phosphorylated many target proteins, the cell extract was analyzed by SDS-PAGE and Western blotting (FIG. 15). Activation of Src protein kinase was shown by blotting extracts of untransfected (lane 1) and Src-transfected (lane 2) 3T3 cells and probing the blot with P-Tyr-100 antibody (Cell Signaling Technology, Inc., product number 9411). The level and extent of tyrosine phosphorylation was much greater in cells that had been stably transfected with Src protein kinase than in untransfected cells.

Proteins in the extract were digested to peptides with immobilized trypsin, and the immobilized trypsin was removed by centrifugation. Immobilized P-Tyr-100 antibody was prepared by mixing 1 mg of P-Tyr-100 and 0.1 ml of protein G-agarose resin (Roche, product number 1 243 233) overnight at 4° C. Unbound antibody was removed by washing the resin three times with cold PBS. The amount of antibody bound to protein G-agarose was shown to be 5 mg antibody/ml resin by measuring the absorbance at 280 nm of the antibody solution before and after immobilization.

Phosphotyrosine-containing peptides were isolated from the complex mixture of peptides contained in the proteinaceous preparation by contacting the trypsin-digested extract (about 12 mg, 1 mg/ml) with phosphotyrosine antibody P-Tyr-100 that was bound to protein G resin (20 μl, 5 mg antibody/ml resin) in batch format at 4° C. for 16 hours. Unbound peptides were removed by centrifugation, and the antibody-resin was extensively washed (three times with 1 ml ice-cold PBS and twice with 1 ml ice-cold water). Bound peptides and antibody were then eluted with 100 μl of 0.1% trifluoroacetic acid, and the eluted peptides were separated from eluted antibody by centrifugation through a Microcon YM-10 membrane (Millipore, product number 42407), which retains molecules with molecular weights above 10,000. Before analysis by MALDI-TOF mass spectrometry, a 9 μl portion of the YM-10 flow-through fraction was desalted and concentrated with a reversed-phase ZipTip microcolumn.

The masses of the peptides that bound to and eluted from the phosphotyrosine antibody were measured by MALDI-TOF mass spectrometry before (FIG. 16, top panel) and after (bottom panel) treating the peptide fraction with shrimp alkaline phosphatase, which can remove phosphate groups from phosphopeptides and produce ions with masses 80 lower than phosphopeptides for each phosphate group in the peptide, to confirm the eluted peptides are phosphorylated (FIG. 16, bottom panel). The masses of eight peptides bound and eluted from phosphotyrosine antibody-resin gave new ions with masses 80 lower than the phosphopeptides after treatment with phosphatase, indicating they are phosphopeptides.

The peptides that bound to and eluted from the phosphotyrosine antibody were further analyzed by LC-MS/MS. A 25 μl portion of the peptide fraction was desalted and concentrated with a reversed-phase ZipTip microcolumn and eluted with 2 μl 0.1% trifluoroacetic acid, 40% acetonitrile. An 0.4 μl aliquot of the eluted fraction was mixed with an ACHA matrix solution and analyzed by MALDI-TOF mass spectrometry, and it gave a spectrum similar to the one shown in FIG. 16. The remainder of the eluted fraction was analyzed by LC-MS/MS.

LC-MS/MS analysis was performed with a ThermoFinnigan Surveyor HPLC system coupled to a ThermoFinnigan LCQ Deca ion trap mass spectrometer. To reduce its acetonitrile concentration to a level that would allow peptides to bind to a reversed-phase support, the sample was diluted 10-fold with 0.5% acetic acid, 0.005% HFBA (heptafluorobutyric acid, Pierce Endogen, part number 25003), 5% acetonitrile containing 1% formic acid. Using a pressure cell, the diluted sample was loaded onto a capillary column (75 μm internal diameter, 15 μm tip, fused silica PicoTip, New Objective, part number FS360-75-15-N) that had been packed with Magic C18AQ reversed-phase resin (5 μm particles, 100 Angstrom pores, Michrom Bioresources, part number 9996610000) and equilibrated with 0.5% acetic acid, 0.005% HFBA, 5% acetonitrile. Peptides were eluted from the column by a linear gradient of increasing acetonitrile concentration at a nominal flow rate of 250 nl/min.

To induce electrospray at the tip of the column, 2,000 V was applied to a liquid junction upstream of the column at a cross used to modulate the flow rate from the HPLC pump, as described by Gatlin et al., supra. ThermoFinnigan Xcalibur software was used for instrument control and data acquisition. As peptides eluted from the LC column, MS/MS spectra were collected in a "top-three" data-dependent manner: the method performed a survey MS scan and then collected MS/MS spectra for the three most abundant ions, if they were above a pre-set intensity threshold and if they were not recently analyzed by MS/MS already (recognized by using the dynamic exclusion feature of Xcalibur software).

Peptides were identified by analyzing all the MS/MS product ion spectra with Sequest, a program that correlates an experimental spectrum to a library of theoretical spectra derived from protein sequence databases to find a best-fit match. One unambiguously identified phosphopeptide is a phosphotyrosine-containing peptide from enolase A (FIG. 17), an abundant enzyme. The residue identified as a phosphorylation site by this method is known to be phosphorylated in cells transfected with Src (see, e.g. Tanaka et al. *J. Biochem (Tokyo)* 117: 554–559 (1995) and Cooper et al. *J. Biol. Chem.* 259: 7835–7841 (1984)). This phosphopeptide corresponds to a prominent peak detected during MALDI-TOF mass spectrometry, labeled "1,885.2" in FIG. 16, demonstrating, the same phosphopeptides detected during MALDI-MS can be further analyzed by LC-MS.

Accordingly, immunoaffinity isolation of modified peptides by the disclosed method detected a site known to be phosphorylated under these cell culture conditions and, as expected, the assigned site fits the antibody's known specificity. This result, isolation of a known enolase phosphopeptide from a digested extract of mouse cells, is in stark contrast to the results reported in Marcus et. al., supra., where, following the failure to isolate a phosphotyrosine-containing peptide from gel-purified human enolase (the same protein), it was expressly concluded that immunoaffinity purification of phosphopeptides is almost impossible.

In a separate study the method of the invention was used to extract phosphotyrosine peptides from NIH/3T3 cells expressing one of two constituitively active tyrosine kinases, v-Abl and c-Src Y527F. These cell lines were left untreated during cell culturing so the bulk of the tyrosine phosphorylation in the cell is expected to originate from the action of the constituitively active kinase expressed in the cell. The objective was to determine whether the method of the invention can be used to detect phosphorylation indicative of Abl or Src activation in the same cellular background.

Lysates were prepared from $2\times10^8$ cells for both cell lines and digested in 2 M urea with trypsin after treatment with DTT and iodoacetamide to alkylate cysteine residues. Before the immunoaffinity step, peptides were prefractionated by reversed-phase solid phase extraction using Sep-Pak $C_{18}$ columns (1 ml column volume per $2\times10^8$ cells) to separate peptides from other cellular components. The solid phase extraction cartridges were eluted with steps of 5, 15, 25, and 40% acetonitrile. Each lyophilized peptide fraction was redissolved in 1 ml PBS and treated with phosphotyrosine antibody (P-Tyr-100, Cell Signaling Technology product number 9411) immobilized on protein G-Sepharose (Roche) (60 μg antibody, 15 μl resin) overnight at 4° C. Antibody-resin was thoroughly washed, and immunoaffinity-purified peptides were eluted with 75 μl of 0.1% TFA. A portion of this fraction (40 μl) was concentrated with Stage tips and analyzed by LC-MS/MS, using a ThermoFinnigan LCQ Deca XP Plus ion trap mass spectrometer. Peptides were eluted from a 10 cm×75 μm reversed-phase column with a 45-min linear gradient of acetonitrile delivered at 280 nl/min. MS/MS spectra were evaluated using the program Sequest with the NCBI mouse protein database.

More phosphopeptides were found in 3T3-Src (179) than in 3T3-Abl (83), which was consistent with the level of phosphotyrosine detected by western blotting. Substantial overlap was observed between the tyrosine phosphorylation sites found in 3T3-Abl and in 3T3-Src: 62 of the 186 phosphotyrosine sites found in 3T3/Src were also found in 3T3-Abl. The overlap may be attributed to activation of a Src-like kinase in 3T3-Abl cells, which were found to contain IIEDNEpYTAR, (SEQ ID NO: 43) the activation loop phosphopeptide from the Src-family members Hck and Lyn, or LIEDNEpYTAR, (SEQ ID NO: 44) which is found in other Src-family members such as Fyn, Lck, Src, and Yes. It is clear that at least one Src-family kinase has been activated in 3T3-Abl cells, but we cannot specify the activated enzyme because Src-family kinases are so closely related and these two peptides have identical mass. Some of the phosphotyrosine sites from known cell signaling proteins found in 3T3-Abl and 3T3-Src are shown in Table 5.

TABLE 5

Selected phosphopeptides found in 3T3-Abl and 3T3-Src

| Protein Name‡ | Abl | Src | Sequence |
|---|---|---|---|
| Tyrosine kinase | | | |
| * Eph receptor A2 | | • | VLEDDPEATpYTTSGGK SEQ ID NO: 45 |
| * Eph receptor A4 | • | • | VLEDDPEAApYTTR SEQ ID NO: 46 |
| Eph receptor B3 | | • | VYIDPFTpYEDPNEAVR SEQ ID NO: 47 |
| focal adhesion kinase | • | • | THAVSVSETDDpYAEIIDEEDTYTMPSTR SEQ ID NO: 48 |
| * focal adhesion kinase | • | • | YMEDSTpYpYK SEQ ID NO: 49 |
| focal adhesion kinase | | • | GSIDREDGSFQGPTGNQHIpYQPVGKPDPAAPPK SEQ ID NO: 50 |
| * hemopoietic cell kinase | • | • | IIEDNEpYTAR SEQ ID NO: 51 |
| * fer protein kinase | | • | QEDGGVpYSSSGLK SEQ ID NO: 52 |
| * Src | | • | LIEDNEpYTAR SEQ ID NO: 53 |
| Ser/Thr kinase cdc2a | • | • | IGEGTpYGVVYK SEQ ID NO: 54 |
| * DYRK1a | • | • | IYQpYIQSR SEQ ID NO: 55 |
| DYRK3 | | • | pYEVLKIIGKGSFGQVAR SEQ ID NO: 56 |
| * GSK3 beta | • | • | GEPNVSpYICSR SEQ ID NO: 57 |
| * HIPK 1 | • | • | AVCSTpYLQSR SEQ ID NO: 58 |
| * HIPK 3 | | • | TVCSTpYLQSR SEQ ID NO: 59 |
| * MAPK1 | | • | VADPDHDHTGFLTEpYVATR SEQ ID NO: 60 |
| * p38 MAP Kinase | | • | HTDDEMTGpYVATR SEQ ID NO: 61 |
| pre-mRNA protein kinase | • | • | LCDFGSASHVADNDITPpYLVSR SEQ ID NO: 62 |
| Cdc42 BP kinase beta | | • | LPDFQDSIFEpYFNTAPLAHDLTFR SEQ ID NO: 63 |
| Adaptor | | | |
| abl-interactor 1 | • | • | TLEPVKPPTVPNDpYMTSPAR SEQ ID NO: 64 |
| caveolin | • | • | YVDSEGHLpYTVPIR SEQ ID NO: 65 |
| Cbl-b | | • | ASQDpYDQLPSSSDGSQAPARPPKPR SEQ ID NO: 66 |
| DOK1 | • | • | TVPPPVPQDPLGSPPALpYAEPLDSLR SEQ ID NO: 67 |

TABLE 5-continued

Selected phosphopeptides found in 3T3-Abl and 3T3-Src

| Protein Name‡ | Abl | Src | Sequence |
|---|---|---|---|
| DOK1 | • | • | IPPGPSQDSVpYSDPLGSTPAGAGEGVHSK<br>SEQ ID NO: 68 |
| DOK1 | • | • | LTDSKEDPIpYDEPEGLAPAPPR<br>SEQ ID NO: 69 |
| DOK1 | | • | LKEEGYELPYNPATDDpYAVPPPR<br>SEQ ID NO: 70 |
| DOK1 | • | • | GFSSDTALpYSQVQK<br>SEQ ID NO: 71 |
| GAB1 | | • | DASSQDCpYDIPR<br>SEQ ID NO: 72 |
| p130 Cas | • | • | TQQGLpYQAPGPNPQFQSPPAK<br>SEQ ID NO: 73 |
| p130 Cas | | • | VGQGYVYEAAQTEQDEpYDTPR<br>SEQ ID NO: 74 |
| p130 Cas | • | • | EETpYDVPPAFAK<br>SEQ ID NO: 75 |
| PI3K p85 beta subunit | • | • | EYDQLpYEEYTR<br>SEQ ID NO: 76 |
| SHB adaptor protein | | • | VTIADDpYSDPFDAK<br>SEQ ID NO: 77 |
| Shc1 | • | • | ELFDDPSpYVNIQNLDK<br>SEQ ID NO: 78 |
| similar to SHB adapt. pro. B | • | • | LDpYCGGGGGGDPGGGQR<br>SEQ ID NO: 79 |
| Crk | | • | RVPCApYDK<br>SEQ ID NO: 80 |
| disabled homolog 2 | | • | GPLNGDTDpYFGQQFDQLSNR<br>SEQ ID NO: 81 |
| DOK1 | | • | KPLpYWDLpYGHVQQQLLK<br>SEQ ID NO: 82 |
| DOK1 | | • | GLpYDLPQEPR<br>SEQ ID NO: 83 |
| DOK1 | | • | LKEEGpYELPpYNPATDDpYAVPPPR<br>SEQ ID NO: 84 |
| HGF reg. tyr. kinase subs. | | • | VCEPCpYEQLNK<br>SEQ ID NO: 85 |
| intersectin 2 | | • | GEPEALpYAAVTK<br>SEQ ID NO: 86 |
| p130 Cas | | • | VGQGYVpYEAAQTEQDEpYDTPR<br>SEQ ID NO: 87 |
| p130 Cas | | • | HPLILAAPPPDSPAAEDVpYDVPPPAPDLpYDVPPGLR<br>SEQ ID NO: 88 |
| p130 Cas | | • | VLPPEVADGSVVDDGVpYAVPPPAER<br>SEQ ID NO: 89 |
| PI3K p85 reg. subunit | | • | LNEWLGNENTEDQpYSLVEDDEDLPHHDEK<br>SEQ ID NO: 90 |

TABLE 5-continued

Selected phosphopeptides found in 3T3-Abl and 3T3-Src

| Protein Name‡ | Abl | Src | Sequence |
|---|---|---|---|
| PLC gamma 1 | | • | IGTAEPDpYGALYEGR<br>SEQ ID NO: 91 |
| Shc1 | | • | MAGFDGSAWDEEEEEPPDHQpYpYNDFPGK<br>SEQ ID NO: 92 |
| Src-assoc. adaptor protein | | • | SVYLQEFQDKGDAEDGDEpYDDPFAGPADTISLASER<br>SEQ ID NO: 93 |
| Src-assoc. adaptor protein | | • | IpYQFTAASPK<br>SEQ ID NO: 94 |
| Src-assoc. adaptor protein | | • | SQPIDDEIpYEELPEEEEDTASVK<br>SEQ ID NO: 95 |
| Stam2 | | • | LVNEAPVYSVpYSK<br>SEEQ ID NO: 96 |
| Wiskott-Aldrich syn.-like | | • | VIpYDFIEK<br>SEQ ID NO: 97 |

‡ * indicates activation loop peptides.
• indicates phosphopeptides found in 3T3-Abl or 3T3-Src.

In 3T3-Src cells, phosphorylation was detected in the activation loop of a Src-family kinase, most likely Tyr-424 of Src. Tyrosine phosphorylation was also found in proteins that are known to be substrates of Src, e.g., the non-receptor tyrosine kinase FAK, the adaptor protein p130Cas, the actin-binding protein cortactin, the phospholipid-binding protein annexin A2, and the STAM-interacting protein Hrs. FAK was phosphorylated at Tyr-397, which creates a binding site for Src-family kinases, and at its activation loop sites Tyr-576 and Tyr-577, which are known to be phosphorylated by Src-family kinases. Seven tyrosine phosphorylation sites were found in p130Cas, all in the Src-substrate region of p130Cas and six containing the YXXP motif, which when phosphorylated results in the interaction of p130Cas with several signaling proteins. Some phosphorylation sites map to putative Src substrates, e.g., SCAP2 is a homolog of the Src-associated phosphoprotein SKAPP55 and was found to be phosphorylated at Tyr-260, which in SKAPP55 is thought to be phosphorylated by the Src-family kinase Fyn.

EXAMPLE V

Isolation of Peptides Containing the Phospho-(Ser) PKC Substrate Motif from an Extract of Jurkat Cells Treated with Tetradecanoyl Phorbol Acetate The method of the invention was further demonstrated using a motif-specific, context-independent polyclonal antibody, phospho-(Ser) PKC substrate motif antibody, to purify phosphopeptides containing the phospho-(Ser) PKC substrate motif from a digested whole cell extract. Protein kinase C (PKC) family members are involved in a number of cellular processes such as secretion, gene expression, proliferation and muscle contraction (see e.g. Nishikawa et al. *J. Biol. Chem.* 272: 952–960 (1997) and Pearson and Kemp *Methods Enzymol.* 200: 62–81 (1991)). Conventional PKC isozymes phosphorylate protein substrates at serine or threonine residues when the target residue occurs within the consensus sequence motif (R/K)(R/K)X(S/T)(hyb)(R/K) (SEQ ID NO: 38), where R/K indicates arginine or lysine, X is any amino acid, S/T indicates the target serine or threonine, and hyb is a hydrophobic amino acid.

Phospho-(Ser) PKC substrate motif antibody (Cell Signaling Technology, Inc., product number 2261) recognizes a plurality of different phosphorylated proteins that contain the consensus sequence motif when phosphorylated but does not recognize the analogous unphosphorylated motif. The specificity of the phospho-(Ser) PKC substrate antibody is that it binds preferentially to proteins and peptides that contain phosphoserine preceded by arginine or lysine at positions −2 and +2 and a hydrophobic residue at the +1 position, i.e., (R/K)XS*(hyb)(R/K) (SEQ ID NO: 39), in a manner substantially independent of the surrounding amino acid sequence. The antibody does not recognize the nonphosphorylated motif or the motif containing phosphothreonine. It is demonstrated here that this antibody can be used in accordance with the method of the invention to purify peptides that contain this phospho-(Ser) PKC substrate motif, to identify other proteins that may be phosphorylated by conventional PKC isozymes on a genome-wide (cell-wide) basis.

For this example, the model system was Jurkat cells, a human cell line derived from an acute T cell leukemia, that had been treated for 10 minutes with a potent activator of protein kinase C, tetradecanoyl phorbol acetate (TPA). The cells were washed, harvested, and lysed by sonication, proteins in the lysate were denatured, and the lysate was cleared by centrifugation.

To show that TPA had activated protein kinase C and caused an increased level of PKC-specific protein phosphorylation, the cell extract was analyzed by SDS-PAGE and Western blotting (FIG. 18). Induction of PKC substrate phosphorylation was shown by probing a blot of TPA-treated cell extract (lane 2) and untreated cell extract (lane 1) with phospho-(Ser) PKC substrate antibody (Cell Signaling Technology, Inc., product number 2261). This showed that TPA treatment altered the phosphorylation state of a large number of different proteins that contain the phospho-(Ser) PKC substrate motif.

Proteins in the extract were digested to peptides with endoproteinase Glu-C immobilized to F7m, a polyvinyl matrix bead (MoBiTec, part number P5101), and the immobilized Glu-C was removed by centrifugation. Immobilized phospho-(Ser) PKC substrate antibody was prepared as described above for immobilized P-Tyr-100 antibody (Example IV). The immobilized antibody was evaluated as described above and found to contain 4 mg antibody per ml of resin.

Phosphopeptides containing the phospho-(Ser) PKC substrate motif were purified from the Glu-C-digested crude cell extract with the antibody immobilized to protein G-agarose resin. The digest (about 40 mg, 1 mg/ml protein) was contacted with immobilized antibody-resin (40 µl, 4 mg/ml) in batch format at 4° C. for 16 hours, and unbound peptides were removed by centrifugation. The antibody-resin was washed extensively (three times with 1 ml ice-cold PBS and twice with 1 ml ice-cold water). Bound peptides were then eluted with 150 µl 0.1% trifluoroacetic acid, and the eluted peptides were separated from eluted antibody by centrifugation through a Microcon YM-10 membrane (Millipore, product number 42407), which retains molecules with molecular weights above 10,000. Before analysis by MALDI-TOF mass spectrometry, a 9 µl portion of the YM-10 flow-through fraction was desalted and concentrated with a reversed-phase ZipTip microcolumn.

MALDI-TOF Analysis

The masses of the peptides that bound to and eluted from the phospho-(Ser) PKC substrate antibody were measured by MALDI-TOF mass spectrometry (FIG. 19, top panel). Phosphatase treatment and metastable decomposition (bottom panel) showed that the antibody-purified peptide fraction contains several candidate phosphopeptides with phosphoserine or phosphothreonine, as expected based on the antibody's specificity. In FIG. 19, peaks labeled with a star correspond to phosphopeptides, peaks labeled with an open circle correspond to nonphosphorylated peptides, and peaks labeled with a square are phosphopeptides that have undergone metastable decomposition and neutral-loss of phosphate.

Phosphopeptide peaks detected during MALDI-TOF mass spectrometry (FIG. 19, top panel) are accompanied by companion peaks that are broader and apparently 84 lower in mass, e.g., the peak with a mass of 1989 has a partner peak at 1905, etc. These companion peaks correspond to metastable decomposition products of phosphopeptides, formed by neutral-loss of phosphate while the phosphopeptide ions are traveling to the detector of the mass spectrometer. The peaks for decomposition products are broader than the peaks for phosphopeptides because the decomposition products form after ionization and the instrument is configured to focus ions that are stable during analysis. For similar reasons, the expected mass shift for loss of phosphate is −98, but −84 mass shifts are observed because, unlike a stable ion, the mass of a decomposition product changes during analysis. Metastable decomposition of phosphopeptides has been noted by others and can be used to recognize and assign phosphopeptides in a MALDI-TOF mass spectrum (Annan and Carr, supra.). Analysis of a large number of synthetic phosphopeptides by MALDI-TOF mass spectrometry indicates that some peptides containing phosphoserine or phosphothreonine (but not phosphotyrosine) residues undergo metastable decomposition. For this reason, metastable decomposition is a reliable indicator of peptides that contain phosphoserine or phosphothreonine.

The phosphorylation state of the peptide fraction was also evaluated by treating it with shrimp alkaline phosphatase, which can remove phosphate groups from phosphopeptides to produce ions with masses 80 lower than phosphopeptides for each phosphate group in the peptide. All phosphopeptide candidates were affected by phosphatase treatment, and four phosphopeptides gave dephosphorylated peptides that were 80 lower in mass than the peptides before treatment (FIG. 19, bottom panel).

LC-MS/MS Analysis

The peptides that bound to and eluted from the phospho-(Ser) PKC substrate motif antibody were further analyzed by LC-MS/MS. A 40 µl portion of the peptide fraction was desalted and concentrated with a reversed-phase ZipTip microcolumn and eluted with 2 µl 0.1% trifluoroacetic acid, 40% acetonitrile. An 0.4 µl aliquot of the eluted fraction was mixed with an ACHA matrix solution and analyzed by MALDI-TOF mass spectrometry, and it gave a spectrum similar to the one shown in FIG. 19. An 0.8 µl aliquot of the eluted fraction was analyzed by LC-MS/MS.

LC-MS/MS analysis was performed as described above (Example IV). The chromatogram obtained by analyzing this sample is shown in FIG. 20. The first panel of FIG. 20 shows where survey MS scans were collected, and the second panel shows where MS/MS spectra were collected.

The third, fourth, and fifth panels show where neutral loss of 49, 32.7, and 24.5, respectively, was detected. During the fragmentation process of MS/MS, peptides containing phosphoserine or phosphothreonine often form an ion by simple loss of phosphate to produce a neutral-loss ion that has a mass 98 lower than the unfragmented parent ion. If the parent ion has a charge of +1, the neutral-loss ion has a mass-to-charge value (m/z) of 98/1 or 98 lower than the parent ion mass-to charge value. Likewise, phosphopeptide parent ions with charges of +2, +3, or +4 will give neutral-loss ions with m/z values that are 49, 32.7, and 24.5 lower than the parent ion. The occurrence and intensities of neutral-loss ions are plotted in the third, fourth, and fifth panels of FIG. 20 to help locate candidate phosphopeptides. The neutral loss plots show that phosphopeptide candidates tend to elute early in the chromatogram, as expected for phosphopeptides due to the hydrophilicity of phosphate groups, and that neutral loss is observed in many of the MS/MS spectra, suggesting this sample is highly enriched with phosphopeptides.

As discussed, neutral loss during MS/MS is the same process as metastable decomposition during MALDI-TOF mass spectrometry. As expected, many of the phosphopeptides showing neutral loss during LC-MS/MS (FIG. 20, panels 3–5) are the same phosphopeptides that gave metastable decomposition during MALDI-TOF mass spectrometry (FIG. 19, top panel), see FIG. 21. For each neutral-loss MS/MS spectrum, the parent ion mass (m) can be calculated from the parent ion mass-to-charge value (m/z) and the charge (z) inferred from the neutral loss value (+2 for neutral loss of 49, +3 for 32.7, and +4 for 24.5). Some individual peptides were observed to undergo neutral loss as +2, +3, and +4 ions. For example, LC-MS/MS spectra 533, 534, and 535 show neutral loss and correspond to +4, +3, and +2 ions, respectively, of a candidate phosphopeptide labeled "2,413.3" in FIG. 19. Both MALDI-TOF mass spectrometry and LC-MS/MS give this peptide a mass of 2,413, and the neutral loss observed during both mass analysis methods show the peptide contains one phosphate. A comparison of datasets shows the same peptides are detected by both mass analysis methods, and all the neutral-loss MS/MS spectra show the peptides contain one phosphate group (FIG. 21).

All the MS/MS product ion spectra were analyzed with Sequest in an attempt to assign a phosphorylation site and parent protein to each peptide, but this did not result in unambiguous assignments. During MS/MS nearly all phosphopeptides underwent neutral loss to a very high degree with very little residual fragmentation along the peptide backbone, which is needed to produce spectra of a quality high enough for unambiguous assignments. In general backbone fragmentation was at the same level as chemical noise, obscuring the features needed to identify the peptides. As noted above, this is a common limitation encountered during MS/MS analysis of peptides containing phosphoserine and phosphothreonine. See e.g., DeGnore et al., supra. Even when phosphopeptides lose phosphate by neutral loss, the position of the phosphorylation site can be determined as long as there is sufficient residual backbone fragmentation, because neutral loss leaves an unusual residue at the phosphorylation site: phosphoserine becomes dehydroalanine, and phosphothreonine becomes dehydroaminobutyric acid.

LC-MS$^3$ Analysis

Some phosphopeptides in this sample were identified by LC-MS$^3$, that is, the neutral-loss ions were subjected to an additional level of MS to give sufficient backbone fragmentation for identification. This process is simpler to implement on ion trap mass spectrometers than on other types of mass spectrometers. As peptides elute from the LC system, a survey MS scan is performed, and MS/MS spectra are collected for the three most abundant ions, if they are above a pre-set intensity threshold and if they have not been recently analyzed by MS/MS already. However, if neutral loss of 49, 32.7, or 24.5 is detected during MS/MS, then before collecting another MS/MS spectrum or another survey MS scan, the instrument first isolates the neutral loss ion, fragments it, and measures the product ion masses. If the neutral-loss ion no longer contains phosphate, it is more likely to fragment like a non-phosphorylated peptide and give a useful product ion spectrum. With certain modifications to the instrument control software, MS$^3$ spectra can be collected in the same data-dependent manner as MS/MS spectra, and the MS$^3$ spectra can be analyzed further with Sequest. See Tomaino and Rush et al., supra.

Data-dependent LC-MS$^3$ was performed on the remainder of the eluted fraction, an 0.8 μl aliquot. FIG. 22 compares the MS/MS spectra (left panels) and the MS$^3$ spectra (right panels) for three phosphopeptides that were identified by this method. Each MS/MS spectrum contains predominantly one product ion, an intense peak differing from the parent ion mass by 32.7, consistent with loss of one phosphate from a phosphopeptide ion with a charge of +3. Nearly all other peaks in the spectrum are at least 20-fold less intense than the neutral-loss ion. The MS/MS spectra collected during LC-MS$^3$ analysis of this sample are very similar to the MS/MS spectra collected during LC-MS/MS analysis, described above, and illustrate how neutral loss can dominate MS/MS spectra of peptides containing phosphoserine or phosphothreonine. Because neutral loss of 32.7 was detected during MS/MS, the mass spectrometer automatically subjected the neutral-loss ion to MS$^3$ to produce the spectra shown in the right panels. These show several product ions of varying intensities distributed throughout the spectra, and as expected they resemble MS/MS spectra of non-phosphorylated peptides.

Using Sequest a phosphorylation site and parent protein can be assigned to each of the three MS$^3$ spectra shown in FIG. 22. As noted in FIG. 21, all three of these assigned phosphopeptides correspond to candidate phosphopeptides identified during MALDI-TOF mass spectrometry. Panel 1 corresponds to PTN6_HUMAN, residues 576–595, with phosphorylation at Ser-585 or Ser-588. Although Sequest unambiguously identified the peptide, in this example, it could not distinguish the two possible phosphorylation sites. However, the sites can be distinguished based on the known specificity of the phospho-(Ser) PKC substrate antibody: the sequence context of Ser-588 (<u>KGS*LK</u>) fits the antibody's specificity but the sequence context of Ser-585 does not (E <u>KS*KG</u>) [underlined residues match the specificity motif (R/K)XS*(hyb)(R/K)].

PTN6 is protein-tyrosine phosphatase 1c, also known as hematopoietic cell protein-tyrosine phosphatase, relevant because the phosphopeptides in this experiment were purified from a human cell line derived from an acute T cell leukemia (Jurkat cells). Brumell et al. (J. Biol. Chem. 272: 875–882 (1997)) have suggested that this specific tyrosine phosphatase is inhibited by PKC-mediated serine phosphorylation, but the specific phosphorylation site has not been identified. Presently, the method of the invention has identified Ser-588 as a possible site of PKC-mediated serine phosphorylation.

Panels 2 and 3 correspond to two overlapping peptides from UFD1_HUMAN that contain the same phosphorylation site. Sequest assigned residues 322–343 with phosphorylation at Ser-335 to the spectrum in panel 2 and residues 333–343 with phosphorylation at Ser-335 to the spectrum in panel 3. The longer peptide is related to the shorter peptide by incomplete proteolytic cleavage: Glu-C did not cleave at Glu-332 completely. In both cases the quality of the Sequest assignments is good, and the position of the phosphorylated residue is unambiguous. The sequence context of Ser-335 (G QS*LR) partially fits the antibody's specificity. UFD1 is ubiquitin fusion degradation protein 1. This protein has not been previously shown to be phosphorylated. Presently, the method of the invention has identified Ser-335 as a novel phosphorylation site.

Confirmation of Sequence

For demonstrative purposes, one of the novel phosphorylation sites was confirmed by showing a synthetic peptide with the assigned sequence and phosphorylation site gives MS/MS and MS$^3$ spectra that are identical to the MS/MS and MS$^3$ spectra of the biological peptide, i.e., the peptide purified by the method of the invention from Glu-C-digested Jurkat cells. UFD1 333–343 phospho-Ser-335 was synthesized at Cell Signaling Technology using Fmoc chemistry. The full-length peptide was purified by HPLC and then analyzed using the same LC-MS$^3$ method described above.

The MS/MS and MS$^3$ spectra for the biological peptide (top panels) and the synthetic peptide (bottom panels) are compared in FIG. 23. Portions of the MS/MS spectra have been amplified by a factor of 10 to show ions other than the neutral-loss ion more clearly. The correspondence between the MS$^3$ spectra demonstrates that the assigned peptide sequence and phosphorylation site are correct. Even though the quality of the MS/MS spectra is compromised by a dominant neutral-loss ion, there is good correspondence between the minor peaks of the two spectra.

In this example, Sequest assigned a peptide sequence and phosphorylation site to a spectrum, and the assignment was confirmed by showing a synthetic peptide with that sequence and phosphorylation site gives the same spectrum. This establishes a formal link between a specific phosphopeptide and its spectrum. This is a simple and convincing way to further evaluate marginal Sequest assignments or to confirm assignments that are considered especially important.

Marginal Assignments

As discussed above, neutral loss of phosphate from phosphoserine or phosphothreonine can make it difficult to assign a peptide sequence to an MS/MS spectrum and occasionally assignments will be ambiguous. In a global proteomic method, where phosphopeptides are isolated and analyzed separately from non-phosphorylated peptides, often the only peptide from a particular protein will be the purified phosphopeptide, and unambiguous assignments are likely to be more difficult to achieve. Accordingly, marginal assignments may be of higher value, and may be worth pursuing further. Marginal assignments that are worth further investigation can be identified by using simple computer programs to screen the bulk results for assignments that fit the known specificity of the antibody used to isolate the phosphopeptides.

As an example of this, the MS/MS spectra of the sample described here was further screened for marginal assignments, using antibody specificity and our higher-confidence MS$^3$ results as guides. As described above, MS$^3$ analysis identified two novel phosphorylation sites in three different peptides: one mapped to PTN6 and fit the known phospho-(Ser) PKC substrate motif, and the other two mapped to UFD1 and fit the motif partially. A comparison of the peptide sequences showed a variation of the motif might be sufficient for antibody recognition: the PTN6 site contained the sequence S*LKRK, and the UFD1 site contained the sequence S*LRKK. Based on this, all the Sequest output files were searched, which listed the top 20 candidate peptide sequences for each spectrum, for marginal results that fit the consensus sequence S*L(R/K)X(R/K) (SEQ ID NO: 40).

This search found a fourth candidate phosphopeptide in an MS/MS spectrum: BRB1_HUMAN, residues 206–233 with phosphorylation at Ser-228. The sequence contains S*LRTR. This peptide has a mass of 3,297 and corresponds to a peak observed during MALDI-TOF mass spectrometry (assigned mass 3,294 in FIG. 21). It is a good example of a marginal phosphopeptide assignment: it is the fourteenth-ranked peptide after the initial round of Sequest scoring, and the eighth-ranked peptide after the final scoring round. Although there are higher-ranked peptides after the final round, they all received very poor scores in the initial round, where they were ranked ninety-fourth or worse. Nevertheless, this result is worth pursuing because the assigned peptide fits the antibody's known specificity and it fits well the higher-confidence assignments made on the basis of MS$^3$ spectra.

BRB1 is the B1 bradykinin receptor. It is known that the B1 bradykinin receptor activates protein kinase C (see Christopher et al. *Hypertension* 38: 602–605 (2001)). There are no known phosphorylation sites in the B1 bradykinin receptor, but the B2 bradykinin receptor is phosphorylated at Ser residues in response to activation of protein kinase C (see Blaukat et al. *J. Biol. Chem.* 276: 40431–40 (2001)). Furthermore, protein kinase C phosphorylation of receptors has been postulated as a general mechanism for receptor desensitization. It is therefore reasonable to presume that protein kinase C could phosphorylate B1 receptors as well. In addition, it is known that the expression of the BRB1 receptor is upregulated on T cells derived from peripheral blood of patients with multiple sclerosis, relevant because this phosphopeptide was purified from a human cell line derived from an acute T cell leukemia (see e.g., Prat et al. *Neurology* 53: 2087–2092 (1999)). The site of phosphorylation tentatively assigned here is in a domain of the protein that is predicted to be cytoplasmic. This tentative assignment may be further explored by analyzing a synthetic peptide with the assigned sequence and phosphorylation site as described above.

The ability to filter assignments and extract marginal assignments that are worth investigating further is a unique advantage of antibody-based purification methods. Without use of an antibody and knowledge of the antibody's specificity, these marginal assignments would be overlooked.

EXAMPLE VI

Isolation of Peptides Containing the Akt Substrate Motif from an Extract of Cells Expressing Activated Akt Protein Kinase Peptides containing the Akt substrate motif (RXRXXT*/ S*, T*=phosphothreonine, S*=phosphoserine) can be selectively isolated from a complex mixture of peptides, such as a digested cell lysate. The Akt protein kinase is an important regulator of cell survival and insulin signaling, but very few of its in vivo targets have been identified. Studies with synthetic peptide substrates of Akt (Alessi et al., *FEBS Lett.* 399: 333–338 (1996)) as well as the analysis of known Akt phosphorylation sites on GSK-3 (Franke et al. *Cell* 88: 435–437 (1997)), Bad (Pap et al.,

*J. Biol. Chem.* 273: 19929–19932 (1998), and Caspase-9 (Cardone et al., *Science* 282: 1318–1321 (1998)) indicate that Akt phosphorylates its substrates only at a serine or threonine in a conserved motif characterized by arginine at positions −5 and −3.

Phospho-(Ser/Thr) Akt substrate polyclonal antibody (Cell Signaling Technology, Inc., product number 9611) is a motif-specific, context-independent antibody that recognizes phosphopeptides with the consensus substrate motif RXRXX(T*/S*), where R is arginine, X is any amino acid, and T*/S* indicates phosphothreonine or phosphoserine. The specificity of the phospho-(Ser/Thr) Akt substrate antibody is that it binds preferentially to proteins and peptides that contain phosphothreonine or phosphoserine preceded by lysine or arginine at positions −5 and −3, i.e., (K/R)X(K/R)XX(T*/S*) (SEQ ID NO: 15), in a manner substantially independent of the surrounding amino acid sequence. To identify potential substrates on a genome-wide (cell-wide) basis, immobilized phospho-Akt substrate antibody was used to immunoaffinity purify phosphopeptides from a proteinaceous preparation in accordance with the method of the invention, as described below.

For this example, the model system was 3T3 mouse fibroblast cells that had been stably transfected to express active Akt protein kinase constituitively and that had been treated with 50 ng/ml platelet-derived growth factor (PDGF) for 15 minutes. The cells were washed, harvested, and lysed by sonication, proteins in the lysate were denatured, and the lysate was cleared by centrifugation.

To show that activated Akt protein kinase had phosphorylated many target proteins, the cell extract was analyzed by SDS-PAGE and Western blotting (FIG. 24). Activation of Akt protein kinase was shown by probing a blot of PDGF-treated, transfected cell extract (lane 2) and untreated, untransfected cell extract (lane 1) with Akt antibody (Cell Signaling Technology, Inc., product number 9272), phospho-Akt (Thr308) antibody (Cell Signaling Technology, Inc., product number 9275), and phospho-Akt (Ser473) antibody (Cell Signaling Technology, Inc., product number 9271). This showed that PDGF treatment altered the phosphorylation state of Akt protein kinase (panels 2 and 3) but not its overall cellular expression level (panel 1). PGDF treatment also altered the phosphorylation state of a large number of different proteins that contain the phospho-Akt substrate motif, shown by probing the blot with phospho-Akt substrate antibody (panel 4). In a separate experiment, it was shown that the major protein recognized by phospho-Akt substrate antibody after PDGF treatment (the dark band near the bottom of panel 4, lane 2) is the ribosomal protein S6, which is known to be phosphorylated in response to growth factor treatment (Ferrari and Thomas, *Crit. Rev. Biochem. Mol. Biol.* 29: 385–413 (1994)).

Proteins in the extract were digested to peptides with endoproteinase Glu-C immobilized to F7m, a polyvinyl matrix bead (MoBiTec, part number P5101), and the immobilized Glu-C was removed by centrifugation. Phosphopeptides containing the phospho-Akt substrate motif were purified from the digest with phospho-Akt substrate antibody immobilized to agarose by hydrazide chemistry, as described above for the P-Tyr-100 monoclonal antibody; each milliliter of resin was reacted with 2 milligrams of antibody. The Glu-C-digested crude cell extract (about 3.5 mg, 0.25 mg/ml protein) was contacted with immobilized phospho-Akt substrate antibody-resin (40 µl, 2 µg/µl) in batch format at 4° C. for 16 hours, and unbound peptides were removed by centrifugation. The antibody-resin was washed extensively (four times with 0.5 ml ice-cold PBS and three times with 0.5 ml ice-cold water). Bound peptides were then eluted with 120 µl 0.1 M glycine, pH 2.3. Before analysis by MALDI-TOF mass spectrometry as described above, a 9 µl portion of the eluted fraction was desalted and concentrated with a reversed-phase ZipTip microcolumn.

MALDI-TOF Analysis

The masses of the peptides that bound to and eluted from the phospho-Akt substrate antibody were measured by MALDI-TOF mass spectrometry before (FIG. 25, top panel) and after (bottom panel) treating the peptide fraction with calf intestinal phosphatase, which can remove phosphate groups from phosphopeptides and produce ions with masses 80 lower than phosphopeptides for each phosphate group in the peptide, to confirm the eluted peptides are phosphorylated. In FIG. 25, peaks labeled with a star correspond to phosphopeptides, peaks labeled with an open circle correspond to nonphosphorylated peptides, and peaks labeled with a square are phosphopeptides that have undergone metastable decomposition and neutral-loss of phosphate.

Four candidate phosphopeptide peaks (FIG. 25, top panel) are each accompanied by companion peaks that are broader and apparently 84 lower in mass, e.g., the peak with a mass of 2,404 has a partner peak at 2,320, and likewise 2,334, 2,324, and 2,254 have partner peaks at 2,250, 2,241, and 2,171, respectively. These companion peaks correspond to metastable decomposition products of phosphopeptides, formed by neutral-loss of phosphate while the phosphopeptide ions are traveling to the detector of the mass spectrometer. Metastable decomposition of phosphopeptides has been noted by others and can be used to recognize and assign phosphopeptides in a MALDI-TOF mass spectrum (Annan and Carr, *Anal. Chem.* 68: 3413–21 (1996)). As described in the previous example, it has been observed that some synthetic peptides containing phosphoserine or phosphothreonine but not phosphotyrosine residues undergo metastable decomposition. The MALDI-TOF mass spectrum in FIG. 25 indicates these candidate phosphopeptides probably contain phosphoserine or phosphothreonine, in accordance with the antibody's known specificity.

When the bound peptide fraction was treated with calf intestinal phosphatase, 3 of the 4 candidate phosphopeptides gave dephosphorylated peptides that were 80 (for one phosphate group) or 160 (for two phosphate groups) lower in mass than the peptides before treatment (FIG. 25, bottom panel): 2,404 and 2,324 differ from 2,244 by two or one phosphate groups, respectively, and 2,334 differs from 2,254 by one phosphate group. The presence of metastable decomposition peaks after phosphatase treatment indicates these peptides are still phosphorylated, i.e., the phosphopeptide with a mass of 2,404 probably contains at least three phosphate groups, and the peptide with a mass of 2,334 probably contains at least two phosphate groups. This is supported by the LC-MS/MS analysis described below, which defined the phosphate content of these peptides more precisely.

It is believed that two of the four immunoaffinity-purified peptides (FIG. 25, top panel) correspond to a known phosphopeptide from the ribosomal protein S6 (accession number P10660), which is the major protein in the PDGF-treated cell extract recognized by Western blotting with phospho-Akt substrate antibody (FIG. 24): the phosphopeptides with an observed mass of 2,254.5 and 2,334.4 fit the expected mass for the Glu-C-peptide from S6 protein QIAKR RRLSS LRAST SKSE (SEQ ID NO: 41) with 1 and 2 phosphate groups, respectively (calculated protonated peptide masses of 2,254.2 and 2,334.2). Based on the duration of PDGF treatment in this experiment and published reports on the order of phosphorylation (Ferrari et al. *J. Biol. Chem.* 266: 22770–5 (1991)), it is expected that only 2 of the 5 phosphorylation sites in this peptide are phosphorylated, Ser235 and Ser236, underlined in the peptide sequence shown above. Furthermore these two sites in the peptide fit the known specificity of the phospho-Akt substrate antibody: Ser235 fits KXRXXS*, and Ser236 fits RXRXXS*.

LC-MS/MS Analysis

The peptides that bound to and eluted from the phospho-Akt substrate antibody were further analyzed by LC-MS/MS. A 25 µl portion of the peptide fraction was desalted and concentrated with a reversed-phase ZipTip microcolumn and eluted with 2 µl 0.1% trifluoroacetic acid, 40% acetonitrile. An 0.4 µl aliquot of the eluted fraction was mixed with an ACHA matrix solution and analyzed by MALDI-TOF mass spectrometry, and it gave a spectrum similar to the one shown in FIG. 25. The remainder of the eluted fraction was analyzed by LC-MS/MS.

LC-MS/MS analysis was performed as described above (Example IV). The chromatogram obtained by analyzing this sample is shown in FIG. 26. The first panel of FIG. 26 shows where survey MS scans were collected, and the second panel shows where MS/MS spectra were collected. The third, fourth, and fifth panels show where neutral loss of 49, 32.7, and 24.5, respectively, was detected, characteristic of ions with charges of +2, +3, and +4 that have undergone neutral loss of phosphate. The occurrence and intensities of neutral-loss ions are plotted in the third, fourth, and fifth panels of FIG. 26 to help locate candidate phosphopeptides. The neutral loss plots show that phosphopeptide candidates tend to elute early in the chromatogram, as expected for phosphopeptides due to the hydrophilicity of phosphate groups, and that neutral loss is observed in many of the MS/MS spectra, suggesting this sample is highly enriched with phosphopeptides.

As noted earlier, neutral loss during MS/MS is the same process as metastable decomposition during MALDI-TOF mass spectrometry. As expected, many of the phosphopeptides showing neutral loss during LC-MS/MS (FIG. 26, panels 3–5) are the same phosphopeptides that gave metastable decomposition during MALDI-TOF mass spectrometry (FIG. 25, top panel), see FIG. 27. Most peptides showing neutral loss during MS/MS contained more than one phosphate group. The MS/MS spectra often gave a clear indication of the number of phosphate groups present in each peptide ion, which MALDI-TOF mass analysis did not provide even after treating the peptides with phosphatase.

The phosphopeptide from the ribosomal protein S6 was observed with one, two, and three phosphates, in good agreement with the MALDI-TOF results described above. FIG. 28 shows a portion of the MS/MS spectra for the S6 phosphopeptide with 1 (panel 1), 2 (panel 2), or 3 (panel 3) phosphates, the parent ions for all three spectra have a charge of +3. Panel 1 shows the spectrum of a parent ion with an m/z value of 752.51 undergoing neutral loss to give a product ion with an m/z value of 719.86, a difference of 32.65, close to the theoretical m/z difference of 32.66 for loss of 98 from an ion with a charge of +3. Only one loss of this m/z value is detected, that is, a product ion corresponding to loss of two phosphate groups (m/z of 687.20) is not detected. On this basis the mass of the peptide is 2,254.5, and it contains 1 phosphate group. Similarly panel 2 shows product ions that have lost this m/z value once and twice, allowing assignment of two phosphate groups, and panel 3 shows loss one, two, and three times, corresponding to 3 phosphate groups. In agreement with this the parent ion masses increase by 80 for each additional phosphate group. As expected, the phosphopeptides eluted earlier during reversed-phase HPLC as the phosphate content increased: with 3, 2, or 1 phosphate groups the peptide eluted at 7.3, 7.6, and 7.8 minutes respectively.

Like this group of ribosomal protein S6 phosphopeptides, LC-MS/MS analysis showed there may be a second group of related phosphopeptides, labeled "peptide A" in FIG. 27. The observed masses are 2,324.5 (with two phosphate groups) and 2,404.6 (with three phosphate groups).

All the MS/MS product ion spectra were analyzed with Sequest in an attempt to assign a parent protein and phosphorylation site to each peptide. This did not result in unambiguous assignments because of the high level of neutral loss with very little residual fragmentation along the peptide backbone. At present, this type of multiply-phosphorylated sample cannot be analyzed effectively by LC-MS$^3$ using the currently available version of the software. The current data-dependent acquisition software isolates and fragments the most abundant neutral-loss ion; for multiply phosphorylated peptides this corresponds to the peptide with one phosphate removed by neutral loss, leaving one or more phosphate groups to undergo neutral loss during MS$^3$. The acquisition software is being revised (per personal communication) to recognize multiples of neutral loss and to isolate and fragment the ion with the highest level of neutral loss, even if it is not the most intense product ion. For example for the spectrum in panel 2 of FIG. 28, the current software would select for MS$^3$ analysis the ion with an m/z value of 746.33 because it is the most intense neutral-loss ion; but the revised software will select the ion with an m/z value of 713.87 because it shows a higher level of neutral loss. It is expected that further analysis of this sample with revised acquisition software will allow the parent proteins and phosphorylation sites of some of these peptides to be unambiguously assigned.

Even without unambiguous fragmentation spectra, the tentative assignment of some of these peptides to a phosphopeptide from the ribosomal protein S6 is consistent with Western blotting results, which suggest S6 is the major phosphoprotein detected by phospho-Akt substrate antibody, and the observed masses and phosphate contents agree with published reports on phosphorylation of this protein after treatment with growth factors.

EXAMPLE VII

Isolation of Peptides Containing the 14-3-3 Binding Motif from an Extract of Cells Treated with a Cyclic AMP Analog and Insulin The method of the invention was further employed to isolate phosphopeptides containing a 14-3-3 binding motif from a complex mixture of peptides existing in a digested cell lysate. The 14-3-3 proteins regulate several biological processes through phosphorylation-dependent protein-protein interactions. A phosphoserine-containing consensus sequence, motif #1, (R/K)SXS*XP, is present in some binding partners of 14-3-3 proteins. Many protein kinases such as Akt and cAMP-dependent protein kinase (PKA) can phosphorylate this motif to initiate binding of 14-3-3 proteins.

Phospho-(Ser) 14-3-3 binding motif monoclonal antibody (4E2) (Cell Signaling Technology, Inc., product number 9606) is a motif-specific, context-independent antibody that recognizes phosphopeptides containing consensus binding motif #1. This antibody is highly specific for peptides and proteins that contain the consensus motif (R/K)XXS*XP, where R is arginine, P is proline, X is any amino acid, and S* indicates phosphoserine. This antibody weakly cross-reacts with analogous sequences containing phosphothreonine instead of phosphoserine in this motif. This antibody was used to immunoaffinity purify phosphopeptides that contain motif #1 from a proteinaceous preparation, so as to identify proteins that may be previously unrecognized binding partners of 14-3-3 proteins.

For this example, the model system was COS-1 cells, a cell line derived from transformed monkey kidney cells, that had been treated with insulin and 8-(4-chlorophenylthio)-cAMP (cpt-cAMP). Insulin induces the Akt protein kinase, and the membrane-permeable, metabolically stable cAMP analog induces the PKA kinase. The induced kinases will phosphorylate many protein sites, and among these many will be 14-3-3 binding sites, that is, some proteins will become binding partners of 14-3-3 proteins as a result of phosphorylation by the Akt, PKA, and other induced protein kinases. A culture of COS-1 cells was treated with 1 µg/ml insulin and 1 mM 8-(4-chlorophenylthio)-cAMP (cpt-cAMP) for 10 minutes. The cells were washed, harvested, and lysed by sonication, proteins in the lysate were denatured, and the lysate was cleared by centrifugation.

To show that treatment with insulin and the cyclic AMP analog had caused an increased level of protein phosphorylation at potential 14-3-3 binding sites, the cell extract was analyzed by SDS-PAGE and Western blotting (FIG. 29). Probing the treated cell extract (lane 2) and the untreated cell extract (lane 1) with phospho-(Ser) 14-3-3 binding motif antibody (Cell Signaling Technology, Inc., product number 9606) showed that this treatment altered the phosphorylation state of a significant number of different proteins that contain the 14-3-3 binding motif #1.

Proteins in the extract were digested to peptides with endoproteinase Glu-C immobilized to F7m, a polyvinyl matrix bead (MoBiTec, part number P5101), and the immobilized Glu-C was removed by centrifugation. Immobilized phospho-(Ser) 14-3-3 binding motif monoclonal antibody (4E2) was prepared as described in Example IIB and was found to contain 4 mg antibody per ml of resin.

Phosphopeptides containing the 14-3-3 binding motif were purified from the Glu-C-digested crude cell extract with phospho-(Ser) 14-3-3 binding motif monoclonal antibody bound protein G-agarose resin. The digest (about 12 mg, 0.5 µg/µl protein) was contacted with immobilized antibody-resin (40 µl, 4 µg/µl) in batch format at 4° C. for 16 hours, and unbound peptides were removed by centrifugation. The antibody-resin was washed extensively (three times with 1 ml ice-cold PBS and two times with 1 ml ice-cold water). Bound peptides were then eluted with 150 µl 0.1% trifluoroacetic acid, and the eluted peptides were separated from eluted antibody by centrifugation through a Microcon YM-10 membrane (Millipore, product number 42407), which retains molecules with molecular weights above 10,000. Before analysis by MALDI-TOF mass spectrometry, a 9 µl portion of the YM-10 flow-through fraction was desalted and concentrated with a reversed-phase ZipTip microcolumn.

MALDI-TOF Analysis

The masses of the peptides that bound to and eluted from the phospho-(Ser) 14-3-3 binding motif antibody were measured by MALDI-TOF mass spectrometry (FIG. 30). In FIG. 30, peaks labeled with a star correspond to phosphopeptides, and peaks labeled with a square are phosphopeptides that have undergone metastable decomposition and neutral-loss of phosphate.

Metastable decomposition showed that the antibody-purified peptide fraction contains several candidate phosphopeptides with phosphoserine or phosphothreonine, as expected based on the antibody's specificity. Metastable decomposition arises when phosphopeptide ions undergo neutral-loss of phosphate while traveling toward the instrument's detector and is indicated in MALDI-TOF spectra by the presence of broad companion peaks about 84 lower in mass than intact phosphopeptide ions. As noted in Examples V and VI, experience with synthetic peptides indicates metastable decomposition is a specific and reliable indicator of peptides that contain phosphoserine or phosphothreonine, so the appearance of metastable decomposition in this spectrum fits the known specificity of the antibody used for purification.

A comparison of the MALDI-TOF mass spectrum for this sample (FIG. 30) and the Akt substrate sample described in Example VI (FIG. 19) shows there may be some overlap between the two sample sets. This is expected because, for both samples, the Akt protein kinase was induced and for both samples the specificities of the antibodies used for phosphopeptide purification overlap [(R/K)XX(S*)XP for the phospho-(Ser) 14-3-3 binding motif monoclonal antibody 4E2 versus (R/K)X(R/K)XX(S*/T*) for the phospho-(Ser/Thr) Akt substrate motif polyclonal antibody]. Two peptides that the sample sets may have in common correspond to the Glu-C peptide from the ribosomal protein S6, QIAKR RRL<u>SS</u> LRAST SKSE (SEQ ID NO: 41) with 1 phosphate group and with 2 phosphate groups (see FIG. 27). Ser235 and Ser236, underlined in the peptide sequence shown above, fit the Akt substrate motif fully and the 14-3-3 binding site motif partially.

LC-MS/MS Analysis

The peptides that bound to and eluted from the phospho-(Ser) 14-3-3 binding motif antibody were further analyzed by LC-MS/MS. A 20 µl portion of the peptide fraction was desalted and concentrated with a reversed-phase ZipTip microcolumn and eluted with 2 µl 0.1% trifluoroacetic acid, 40% acetonitrile. An 0.4 µl aliquot of the eluted fraction was mixed with an ACHA matrix solution and analyzed by MALDI-TOF mass spectrometry, and it gave a spectrum similar to the one shown in FIG. 30. The remainder of the eluted fraction was analyzed by LC-MS/MS.

LC-MS/MS analysis was performed as described above (Example IV). The chromatogram obtained by analyzing this sample is shown in FIG. 31. The first panel of FIG. 31 shows where survey MS scans were collected, the second panel shows where MS/MS spectra were collected, and the third, fourth, and fifth panels show where neutral loss of 49, 32.7, and 24.5, respectively, was detected, characteristic of ions with charges of +2, +3, and +4 that have undergone neutral loss of phosphate. The occurrence and intensities of neutral-loss ions are plotted in the third, fourth, and fifth panels of FIG. 31 to help locate candidate phosphopeptides. The neutral loss plots show that phosphopeptide candidates tend to elute early in the chromatogram, as expected for phosphopeptides due to the hydrophilicity of phosphate groups, and that neutral loss is observed in many of the MS/MS spectra, suggesting this sample is highly enriched with phosphopeptides.

Many of the phosphopeptides showing neutral loss during LC-MS/MS (FIG. 31, panels 3–5) are the same phosphopeptides that gave metastable decomposition during MALDI-TOF mass spectrometry (FIG. 30), see FIG. 32. Like the Akt substrate sample described in Example VI, most peptides showing neutral loss during MS/MS contained more than one phosphate group. The LC-MS/MS analysis results support the interpretation made on the basis of the MALDI-TOF mass spectrum, that there is likely to be considerable overlap between the set of peptides purified with the Akt substrate antibody and the 14-3-3 binding motif antibody, including the tentatively assigned multiply phosphorylated peptides from ribosomal protein S6.

Another indication of overlap between the two sample sets is provided by residual backbone fragmentation observed in some of the MS/MS spectra, see FIG. 33. The left panels are MS/MS spectra from the Akt substrate antibody sample set, and the right panels are the corresponding spectra from the 14-3-3 binding motif antibody sample set. The top panels are both assigned tentatively to an ion with a charge of +4 corresponding to the S6 peptide with two phosphate groups: in addition to neutral loss, both spectra show a product ion with an m/z value of 668.2, possibly the b17-$H_3PO_4$ product ion with a charge of +3 (calculated m/z of 668.04). The bottom panels are both assigned to an ion with a charge of +4 that has a mass of 3,204 and contains two phosphate groups: both spectra show a product ion with an m/z value of 990.7.

All the MS/MS product ion spectra were analyzed with Sequest in an attempt to assign a phosphorylation site and parent protein to each peptide. In many cases here (as also noted in Examples V and VI) this did not result in unambiguous assignments because of the high level of neutral loss with very little residual fragmentation along the peptide backbone. MS/MS showed that many of the most abundant phosphopeptides are multiply-phosphorylated and will be amenable to $MS^3$ analysis after the current data acquisition software is revised to recognize multiples of neutral loss and to isolate and fragment the ion with the highest level of neutral loss (as noted in Example VI).

One peptide in this sample that was unambiguously identified is a phosphoserine-containing peptide from heat shock 27 kDa protein (FIG. 34). The residue identified as a phosphorylation site by this method, Ser-78, is known to be phosphorylated by several protein kinases, including S6 kinases and mitogen-activated protein kinases, which are likely to have been activated by the treatments used to prepare this sample. See e.g., Landry et al. *J. Biol. Chem.* 267: 794–803 (1992) and Bird et al. *FEBS Lett.* 338: 31–36 (1994). This phosphopeptide corresponds to a prominent peak detected during MALDI-TOF mass spectrometry, labeled "2,384.6" in FIG. 30. The MS/MS spectrum for the peptide as an ion with a charge of +2 shows a prominent neutral-loss product ion, consistent with loss of one phosphate group (see FIG. 32). The spectrum that could be assigned a parent protein and phosphorylation site by Sequest was produced from the same peptide as an ion with a charge of +3. As expected, the sequence context of Ser-78 (RALS*RQ) fits the known specificity of the phospho-(Ser) 14-3-3 binding motif antibody used to purify the phosphopeptide [underlined residues match the specificity motif (R/K)XXS*XP].

EXAMPLE VIII

Isolation of Peptides Containing the Phospho-PDK1 Docking Motif from a Crude Cell Extract Peptides containing the phospho-PDK1 docking motif (FXXF(S*/T*)(F/Y) (SEQ ID NO: 42), where F is phenylalanine, X is any amino acid, S*/T* indicates phosphoserine or phosphothreonine, and F/Y indicates phenylalanine or tyrosine) may be selectively isolated from a complex mixture of peptides, such as a digested cell lysate. Many protein kinases contain this docking motif sequence, and phosphorylation of this sequence is required for these kinases to bind to 3-phosphoinositide-dependent kinase 1 (PDK1). PDK1 plays a central role in the activation of several growth factor-induced protein kinases, including protein kinase B (PKB), p70 S6 kinase, several PKC isotypes, and serum and glucocorticoid-induced kinase (SGK). See, e.g. Belham et al., *Curr. Biol.* 11: R93–R96 (1999).

The phospho-PDK1 docking motif 18A2 (bulky rings) monoclonal antibody (Cell Signaling Technology, Inc., product number 9634) is a motif-specific, context-independent antibody that recognizes phosphopeptides with the consensus sequence FXXF(S*/T*)(F/Y), where F is phenylalanine, X is any amino acid, S*/T* indicates phosphoserine or phosphothreonine, and F/Y indicates phenylalanine or tyrosine. To identify other proteins with this PDK1 docking motif or profile the activation states of known PDK1 substrates on a cell-wide basis, immobilized PDK1 docking motif (bulky rings) antibody may be employed to immunoaffinity purify phosphopeptides containing the motif from a complex mixture of peptides, such as a digested cell lysate. For example, a proteinaceous preparation may be obtained from a COS cell line (monkey) that overexpresses Akt protein, from 3T3 cells (mouse) treated with platelet derived growth factor, or from Jurkat (human) cells. The extract is prepared and proteins denatured as described above (see "Proteinaceous preparations"), then digested with immobilized trypsin or other proteases.

Phosphopeptides containing the PDK1 docking motif are isolated from the complex mixture in the digested cell lysate with the bulky rings monoclonal antibody (PDK1 docking motif) immobilized to agarose resin by hydrazide chemistry, as described above for P-Tyr-100 monoclonal and P-Thr polyclonal antibodies. The digest is contacted with the antibody-resin in batch format at 4° C. for 1 to 16 hours. Unbound peptides are then removed by centrifugation, and the antibody-resin is extensively washed before eluting bound peptides with 0.1 M glycine, pH 2.3. The eluted peptides are concentrated and desalted with reversed-phase ZipTip microcolumns. The masses of the eluted peptides are measured before and after treating aliquots of the eluted peptides with phosphatase, which can remove phosphate groups from the phosphopeptides and reduce the phosphopeptide masses by 80 for each phosphate present in the peptide. The mixture of phosphopeptides is then analyzed by MS/MS, as described above, to obtain partial peptide sequence information to facilitate identifying the parent proteins from which each phosphopeptide originated. It is expected that each phosphopeptide sequence will fit the PDK1 docking motif consensus sequence described above.

EXAMPLE IX

Isolation of Acetyl-lysine-Containing Peptides from a Crude Cell Extract

Peptides containing acetylated residues, e.g. acetylated-lysine, may be selectively isolated from a complex mixture of peptides, such as a digested cell lysate, according to the method of the invention. It is known that acetylation regulates chromatin structure and gene activity through modification of histones and transcription factors, and thus specific isolation of acetylated peptides would provide important information on the activation states of these biologically important proteins.

Acetylated-lysine monoclonal antibody (Cell Signaling Technology, Inc., product number 9681) specifically recognizes proteins that have been post-translationally modified by acetylation at lysine epsilon-amino groups. To identify other sites of acetylation, immobilized acetylated-lysine antibody may be used to immunoaffinity purify modified (i.e. acetylated) peptides from a proteinaceous preparation, according to the method of the invention. For example, a digested cell lysate containing a complex mixture of peptides may be prepared from a COS cell line (monkey) that overexpresses the HIV Nef protein, which is acetylated at lysine-4. The proteinaceous preparation is prepared and proteins denatured as described above (see "Proteinaceous preparations"), and digested with immobilized trypsin or other suitable immobilized proteases that can be removed from the digest by centrifugation.

Acetylated peptides may then be isolated from the digested cell lysate with the acetyl-lysine specific antibody (a general modification-specific antibody) linked to agarose resin using a hydrazide chemistry, as was described above for the P-Tyr-100 monoclonal antibody and the P-Thr-polyclonal antibody. To isolate acetylated peptides, the digested crude extract may then be contacted with the immobilized acetylated-lysine monoclonal antibody at 4° C. overnight. The resin may then be recovered by centrifugation and extensively washed as described above. The bound peptides may then be eluted by treating the antibody-resin with an eluting solvent such as 0.1% trifluoroacetic acid and centrifugation through a plastic frit.

For this cell line, the overexpressed HIV Nef protein is the most prominent acetylated protein in the cell, and it is expected that acetylated HIV Nef peptides will be specifically isolated, along with other acetylated peptides, according to the method of the invention. These peptides and other acetylated peptides may be further analyzed by MS/MS to obtain partial sequences that can be used to identify the parent proteins. For the HIV Nef protein, for example, a partial sequence will help confirm the peptide isolated from the crude extract is indeed from the HIV Nef protein. Analysis of other acetylated peptides purified by this method may identify new, previously unknown acetylation sites, and in these cases the partial sequence analysis is necessary to match each acetylated peptide with its parent protein. Generally, a peptide's mass and a partial sequence of that peptide is sufficient to identify the parent protein for that peptide, as long as the parent protein's sequence is stored in a public protein sequence database. See Mann et al., *Anal. Chem.* 66: 4390–4399 (1994).

EXAMPLE X

Profiling of Activated Pathways in Tumor Tissue by Isolation of Modified Peptides from a Crude Tissue Extract Activation status of important biological signaling pathways in diseased tissue may be profiled by selective isolation of modified peptides in accordance with the method of the invention. Activation of specific cellular signaling pathways depends, for example, upon the phosphorylation of specific proteins. Therefore, protein phosphorylation states in target cell, e.g. tumor cells, may be used to profile pathway activation by preparing cell extracts from biopsy samples of tumor tissues from which modified peptides may be selectively isolated.

Profiling of protein phosphorylation states in tumor cell, e.g. a breast tumor cell, may be carried out by obtaining a proteinaceous preparation, which contains a complex mixture of peptides, from the target tumor cell. A proteinaceous preparation may be obtained from a single needle biopsy from a breast tumor, which provides sufficient cellular extract to profile the activation status of multiple signaling pathways, including, e.g., the MAP kinase pathway, various growth factor receptor pathways, including epidermal growth factor receptor, steroid receptors, such as the estrogen receptor, and the PI-3-kinase Akt pathway. All of these pathways have been shown to be involved in breast cancer and are important targets for current and future drug development and patient therapy.

To evaluate changes in the signaling pathways of specific breast cancer biopsies, a proteinaceous preparation is obtained from the biopsy sample and desired modified peptides, e.g. phosphopeptides, from that fraction are immunoaffinity purified and characterized by MS as described above. A protein fraction is obtained from frozen biopsy tissue by sonication, and insoluble material and cytoskeletal proteins are removed by centrifugation. The supernatant fraction, containing the bulk of the cellular proteins, is then denatured by heat treatment and digested with immobilized trypsin or some other specific proteolytic enzyme. This proteinaceous preparation contains modified phosphopeptides from multiple different proteins. The proteinaceous preparation is contacted with an immobilized general phospho-specific antibody, e.g. a phosphotyrosine-specific antibody, to isolate phosphopeptides from the complex mixture in the proteinaceous preparation by immunoaffinity isolation. A single type of antibody-resin or several types of antibody-resin in series may be employed; e.g., the protein fraction is contacted with an immobilized phosphotyrosine-specific antibody (e.g. in a column, as previously described), and the unbound fraction from that step is then treated with an immobilized Akt substrate motif-specific antibody in a second support, etc. The immobilized antibody-resins are washed extensively to remove unbound (e.g. nonphosphorylated) peptides, and the bound peptide fraction is then recovered by treating the antibody-resin with an eluting solvent such as 0.1% trifluoroacetic acid.

The eluted phosphopeptides are then analyzed by MALDI-TOF MS, and phosphorylation is confirmed by measuring the peptide mass again after treating an aliquot of the bound fraction with phosphatase, which should reduce each peptide mass by 80 for each phosphate group. To assign the modified peptides to their parent proteins, the bound peptide fraction is analyzed by MS/MS. The partial sequence information obtained, along with the peptide mass, is sufficient to unambiguously identify the parent protein of each peptide. See Mann et al. (1994), supra. Ideally, this procedure is performed with tumor and normal cell biopsies from the same patient. However, if certain phosphorylation sites are known to be diagnostic markers for a specific cancer, then the method can be used to assay the presence of those markers only, without a normal cell reference.

The amounts of phosphorylated peptides isolated from the target cells from tumor tissues are compared to levels observed in extracts from reference cells from normal tissues. Alterations in phosphorylation of a given peptide (and thus, its parent protein), when compared to the reference cell phosphorylation state, will indicate activation of the corresponding signaling pathway. Information obtained from this profiling may be used to determine the best therapy for the patient, as well as to monitor the specific effects of the therapy, e.g. drug treatment, on the targeted signaling pathways. Profiling of phosphorylation states in a target diseased cell, such as a breast tumor cell, also provides information useful in drug development, e.g. to assess the effect of a test drug, as well as for cancer research to identify which signaling proteins and pathways are involved in specific cancers. Other post-translational modifications of proteins that may be relevant to disease states, such as cancer, may similarly be examined by the methods disclosed herein.

EXAMPLE XI

Purification and Identification of Phosphotyrosine Peptides from Anaplastic Large Cell Lymphoma Cell Lines The method of the invention was employed to identify tyrosine phosphorylated peptides from two cancer cell lines that express the same activated tyrosine kinase. Karpas 299 and SU-DHL-1 are derived from anaplastic large cell lymphomas (ALCL). The majority of ALCL is characterized by the presence of the t(2;5)(p23;q35) chromosomal translocation that causes the fusion of the nucleophosmin and anaplastic lymphoma kinase (ALK) genes. See Morris et al. *Science* 263: 1281–1284 (1994). Although the two cell lines are derived from different patients, both express the oncogenic fusion kinase NPM-ALK, which possesses constitutive tyrosine kinase activity and can transform non-malignant cells.

Lysates were prepared from $2 \times 10^8$ cells for both cell lines and digested in 2 M urea with trypsin after treatment with DTT and iodoacetamide to alkylate cysteine residues. Before the immunoaffinity step, peptides were prefractionated by reversed-phase solid phase extraction using Sep-Pak $C_{18}$ columns (1 ml column volume per $2 \times 10^8$ cells) to separate peptides from other cellular components. The solid phase extraction cartridges were eluted with steps of 5, 15, 25, and 40% acetonitrile. Each lyophilized peptide fraction was redissolved in 1 ml PBS and treated with phosphotyrosine antibody (P-Tyr-100, CST #9411) immobilized on protein G-Sepharose (Roche) (60 μg antibody, 15 μl resin) overnight at 4° C. Antibody-resin was thoroughly washed, and immunoaffinity-purified peptides were eluted with 75 μl of 0.1% TFA. A portion of this fraction (40 μl) was concentrated with Stage tips and analyzed by LC-MS/MS, using a ThermoFinnigan LCQ Deca XP Plus ion trap mass spectrometer. Peptides were eluted from a 10 cm×75 μm reversed-phase column with a 45-min linear gradient of acetonitrile delivered at 280 nl/min. MS/MS spectra were evaluated using the program Sequest with the NCBI human protein database.

This revealed a total of 117 tyrosine phosphorylation sites in SU-DHL-1 and 84 tyrosine phosphorylation sites in Karpas 299. As expected there was large overlap (72%) between the phosphorylation sites found in these two similar cell lines. Some phosphotyrosine sites found in the ALCL cell lines that originate from known cell signaling proteins are shown in Table 6.

TABLE 6

Phosphotyrosine peptides found in ALCL cell lines

| Protein Name‡ | K§ | S§ | Sequence |
|---|---|---|---|
| Tyrosine kinase activated p21cdc42Hs kinase | | • | KPTpYDPVSEDQDPLSSDFK<br>SEQ ID NO: 98 |
| anaplastic lymphoma kinase | | • | HQELQAMQMELQSPEpYK<br>SEQ ID NO: 99 |
| anaplastic lymphoma kinase | • | • | TSTIMTDpYNPNpYCFAGK<br>SEQ ID NO: 100 |
| anaplastic lymphoma kinase | • | | GLGHGAFGEVpYEGQVSGMPND<br>PSPLQVAVK<br>SEQ ID NO: 101 |
| anaplastic lymphoma kinase | • | • | NKPTSLWNPTpYGSWFTEK<br>SEQ ID NO: 102 |
| anaplastic lymphoma kinase | • | • | HFPCGNVNpYGYQQQGLPLEAA<br>TAPGAGHYEDTILK<br>SEQ ID NO: 103 |
| Janus kinase 3 | • | • | DLNSLISSDpYELLSDPTPGAL<br>APR<br>SEQ ID NO: 104 |
| Ser/Thr kinase<br>cdc2 | • | • | IGEGTpYGVVYK<br>SEQ ID NO: 105 |
| cdc2 | • | • | IGEGTYGVVpYK<br>SEQ ID NO: 106 |
| DYRK1A | • | • | VYNDGYDDDNpYDYIVK<br>SEQ ID NO: 107 |
| * DYRK1A | • | • | IYQpYIQSR<br>SEQ ID NO: 108 |
| DYRK3 | | • | pYEVLKIIGKGSFGQVAR<br>SEQ ID NO: 109 |
| * ERK2 | | • | VADPDHDHTGFLTEpYVATR<br>SEQ ID NO: 110 |
| * GSK3 alpha | • | • | GEPNVSpYICSR<br>SEQ ID NO: 111 |
| * HIPK1 | | • | AVCSTpYLQSR<br>SEQ ID NO: 112 |
| * p38 alpha MAPK | • | • | HTDDEMTGpYVATR<br>SEQ ID NO: 113 |
| * PRP4K | • | • | LCDFGSASHVADNDITPpYL<br>VSR<br>SEQ ID NO: 114 |
| Adaptor<br>CD2-associated protein | | • | ISTpYGLPAGGIQPHPQTK<br>SEQ ID NO: 115 |
| dok2 | | • | GQEGEpYAVPFDAVAR<br>SEQ ID NO: 116 |
| HGF reg. tyr. kinase subs. | | • | VCEPCpYEQLNR<br>SEQ ID NO: 117 |
| insulin receptor substrate 1 | | • | LEpYYENEK<br>SEQ ID NO: 118 |
| insulin receptor substrate 1 | | • | VDPNGpYMMMSPSGGCSPDIGG<br>GPSSSSSSSNAVPSGTSYGK<br>SEQ ID NO: 119 |

TABLE 6-continued

Phosphotyrosine peptides found in ALCL cell lines

| Protein Name‡ | K§ | S§ | Sequence |
|---|---|---|---|
| intersectin 2 isoform 1 | | • | REEPEALpYAAVNK SEQ ID NO: 120 |
| Oncogene CBL2 | • | • | IKPSSSANAIpYSLAAR SEQ ID NO: 121 |
| SHC | • | • | MAGFDGSAWDEEEEEPPDHQpYpYNDFPGK SEQ ID NO: 122 |
| SHC | • | • | ELFDDPSpYVNVQNLDK SEQ ID NO: 123 |
| SHP2 | • | • | IQNTGDpYYDLYGGEK SEQ ID NO: 124 |
| T lymphocyte adaptor | | • | SCQNLGpYTAASPQAPEAASSTGNAER SEQ ID NO: 125 |
| T lymphocyte adaptor | | • | SQDPNPQpYSPIIK SEQ ID NO: 126 |
| T lymphocyte adaptor | | • | GSPGEAPSNIpYVEVEDEGLPATLGHPVLR SEQ ID NO: 127 |
| Wiskott-Aldrich syn. protein | | • | LIpYDFIEDQGGLEAVR SEQ ID NO: 128 |

‡ * indicates activation loop peptides.
§ "K" indicates peptide found in Karpas 299, "S" in SU-DHL-1.
• indicates phosphopeptides found in Karpas 299 or SU-DHL-1.

To identify more phosphorylation sites, the same SU-DHL-1 cell extract was digested with trypsin, chymotrypsin, endoproteinase GluC, or elastase, and tyrosine phosphorylated peptides were purified and analyzed as described above, resulting in the identification of 90 phosphotyrosine peptides from the trypsin digest, 58 from chymotrypsin, 43 from endoproteinase GluC, and 82 from elastase. A panel of proteases increased the number of distinct tyrosine phosphorylation sites found from 88 using trypsin alone to 197 using all four proteases. Most (35 of 54) phosphorylation sites from the elastase digest were not found in the tryptic digest. This small union between phosphorylation sites from two digests shows that the use of different proteases produced a more complete phosphorylation profile. Activation loop phosphorylation at Tyr-1282 of ALK was found only after digestion with chymotrypsin, as a 12-residue peptide; this residue is predicted to be in a 5-residue tryptic peptide or a 57-residue endoproteinase GluC peptide, both outside the range of peptide lengths amenable to MS/MS-based identification. In addition, the protease panel generated overlapping phosphopeptide sequences, which confirmed phosphorylation site assignments. The ALK Tyr-1507 site was found in five peptides: three tryptic peptides, one chymotryptic peptide, and one elastase peptide.

A total of 264 phosphopeptides representing 197 different phosphotyrosine sites were identified in SU-DHL-1 cells. The only tyrosine kinase showing activation loop phosphorylation in the ALCL cell lines was ALK. Altogether nine different sites of ALK phosphorylation, including five new sites, were observed. The four known ALK sites included phosphotyrosine residues that allow ALK to interact with other signaling proteins such as phospholipase C-gamma, SHC, and IRS-1. Among human lymphomas, STAT3 phosphorylation is correlated with ALK expression, suggesting STAT3 phosphorylation may be a secondary marker for this malignancy, and a recent study demonstrated a favorable clinical outcome for the minority of ALCL patients who have tumors that express ALK but not phosphorylated STAT3. These ALCL cell lines were found to contain both STAT3 isoform 1 and STAT3 isoform 2 phosphorylated at Tyr-705, which induces dimerization and nuclear translocation of this transcription factor.

EXAMPLE XII

Purification and Identification of Phosphotyrosine Peptides from Pervanadate-Treated Jurkat Cells Tyrosine phosphorylated peptides were identified from pervanadate-treated Jurkat cells according to the method of the invention. Jurkat cells are an established T cell line derived from patients with acute lymphoblastic leukemia and leukemic transformed non-Hodgkin lymphoma. Pervanadate produces a hyperphosphorylated cell state by disabling protein tyrosine phosphatases, markedly increasing the level of protein-associated phosphotyrosine. See Srivastava and St-Louis, *Mol. Cell. Biochem.* 176: 47–51 (1997). Proteins were extracted from $2\times10^8$ cells under denaturing conditions and digested with trypsin, and the resulting complex peptide mixture was separated from non-peptide components, concentrated, and partitioned into three fractions by reversed-phase solid-phase extraction. Each fraction was then treated with the phosphotyrosine-specific antibody P-Tyr-100 immobilized on agarose beads. After thorough washing, peptides were eluted from the immobilized antibody with dilute acid and analyzed by nanoflow LC-MS/MS using an ion trap mass spectrometer. MS/MS spectra were assigned to peptide sequences using the program Sequest, and each assignment was manually confirmed.

A total of 175 phosphorylation sites in 156 phosphotyrosine peptides was found in this sample. Most of the purified peptides were phosphorylated: 88 of the 100 top-scoring Sequest assignments corresponded to phosphotyrosine peptides. Unphosphorylated peptides were usually hydrophobic and from abundant proteins, and it is likely they contaminated the phosphopeptide fractions because of a non-specific affinity for agarose beads. Some of the phosphopeptides originating from cell signaling proteins that were found in this sample are listed in Table 7.

TABLE 7

Phosphotyrosine peptides found in pervanadate-treated Jurkat cells

| Protein Name‡ | TCR | Sequence |
|---|---|---|
| Tyrosine kinase * ephrin receptor EphA4 | | VLEDDPEAApYTTR SEQ ID NO: 129 |
| * fer tyrosine kinase | | QEDGGVpYSSSGLK SEQ ID NO: 130 |
| oncogene LCK | Yes | NLDNGGFpYISPR SEQ ID NO: 131 |
| * oncogene LCK | Yes | LIEDNEpYTAR SEQ ID NO: 132 |

TABLE 7-continued

Phosphotyrosine peptides found in pervanadate-treated Jurkat cells

| Protein Name‡ | TCR | Sequence |
|---|---|---|
| oncogene LCK | Yes | SVLEDFFTATEGQpYQPQP SEQ ID NO: 133 |
| ZAP-70 | Yes | IDTLNSDGpYTPEPAR SEQ ID NO: 134 |
| ZAP-70 | Yes | PMPMDTSVpYESPpYSDPEELK SEQ ID NO: 135 |
| * ZAP-70 | Yes | ALGADDSpYpYTAR SEQ ID NO: 136 |
| Ser/Thr kinase | | |
| cdc2 | | IGEGTpYGVVYK SEQ ID NO: 137 |
| cdk6 | | ADQQpYECVAEIGEGApYGK SEQ ID NO: 138 |
| * GSK3 alpha | | GEPNVSpYICSR SEQ ID NO: 139 |
| myosin light chain kinase 1 | | QEGSIEVpYEDAGSHpYLCLLK SEQ ID NO: 140 |
| * p38 alpha MAPK kinase 1 | Yes | HTDDEMTGpYVATR SEQ ID NO: 141 |
| * PRP4K | | LCDFGSASHVADNDITPpYLVSR SEQ ID NO: 142 |
| Adaptor | | |
| abl-interactor 1 | | TLEPVKPPTVPNDpYMTSPAR SEQ ID NO: 143 |
| Arrestin beta 2 | | GMKDDDpYDDQLC SEQ ID NO: 144 |
| erbb2-interacting protein | | SATLLpYDQPLQVFTGSSSSSDLISGTK SEQ ID NO: 145 |
| erbb2-interacting protein | | GPTSGPQSAPQIpYGPPQYNIQpYSSSAAVK SEQ ID NO: 146 |
| erbb2-interacting protein | | AQIPEGDpYLSpYR SEQ ID NO: 147 |
| intersectin 2 isoform 1 | | REEPEALpYAAVNK SEQ ID NO: 148 |
| LAIR-1 | | ETDTSALAAGSSQEVTpYAQLDHWALTQR SEQ ID NO: 149 |
| NCK adaptor protein 1 | | LpYDLNMPAYVK SEQ ID NO: 150 |
| p62dok1 | Yes | IAPCPSQDSLpYSDPLDSTSAQAGEGVQR SEQ ID NO: 151 |
| p62dok1 | Yes | EDPIpYDEPEGLAPVPPQGLpYDLPR SEQ ID NO: 152 |
| p62dok1 | Yes | VKEEGpYELPYNPATDDpYAVPPPR SEQ ID NO: 153 |
| phosprot. assoc. GEM | | ENDpYESISDLQQGR SEQ ID NO: 154 |
| "phospholipase C, gamma 1" | Yes | IGTAEPDpYGALpYEGR SEQ ID NO: 155 |
| "phospholipase C, gamma 1" | Yes | NPGFpYVEANPMPTFK SEQ ID NO: 156 |
| "phospholipase C, gamma 2" | | DINSLpYDVSR SEQ ID NO: 157 |
| "phospholipase C, gamma 2" | | RQEELNNQLFLpYDTHQNLR SEQ ID NO: 158 |
| SHC | Yes | ELFDDPSpYVNVQNLDK SEQ ID NO: 159 |
| SHP2 interacting tm adaptor | Yes | SGESVEEVPLpYGNLHpYLQTGR SEQ ID NO: 160 |
| SHP2 interacting tm adaptor | Yes | SQASGPEPELpYASVCAQTR SEQ ID NO: 161 |
| SHP2 interacting tm adaptor | Yes | ASFPDQApYANSQPAAS SEQ ID NO: 162 |
| Wiskott-Aldrich syn. protein | | LIpYDFIEDQGGLEAVR SEQ ID NO: 163 |

‡ * indicates activation loop peptides.
TCR indicates proteins with known roles is T cell receptor signaling.

About one-third (56 of 156) of the phosphotyrosine peptides found in this sample originated from proteins with well-documented roles in T cell receptor signaling. Among these were the tyrosine kinases ZAP70 and Lck, which are activated by T cell receptor stimulation. Six tyrosine phosphorylation sites were found in ZAP70, including Tyr-493 in the activation loop, and three sites were found in Lck, including the activation loop site Tyr-394. All the tyrosine phosphorylation sites found in ZAP70 and Lck have been reported previously. Phosphorylation sites in the activation loops of two other tyrosine kinases and three serine/threonine kinases were also found: the receptor tyrosine kinase EphA4 and the cytoplasmic Fer tyrosine kinase, as well as activated serine/threonine kinases p38 MAP kinase, GSK3 alpha, and PRP4. In addition, many phosphotyrosine-binding adaptor proteins involved in signal propagation were identified as tyrosine phosphorylated, including p62dok1, NCK, SHC, SHP2, and the phospholipase C gamma 1 and gamma 2 isoforms.

This demonstrates the method of the invention can be used to identify tyrosine kinases that are abnormally activated in cancer cells as well as their substrates, including other protein kinases and adaptor proteins.

What is claimed is:

1. A method for isolating a target population of naturally-occurring post-translatiorially modified peptides from a complex mixture of peptides, said method comprising the steps of:
   (a) obtaining a digested proteinaccous preparation from an organism, wherein said digested proteinaccous preparation comprises a complex mixture of peptides comprising naturally-occurring post-translationally modified peptides from two or more different proteins and further fractionating said post-translationally modified peptides in said digested proteinaceous preparation by reversed-phased chromatography to produce a fractionated proteinaceous preparation;
   (b) contacting said fractionated proteinaccous preparation with at least one immobilized post-translational modification-specific antibody; and
   (c) isolating said target of naturally-occurring post-translationally modified peptides specifically bound by said immobilized inodification-specific antibody in step (b).

2. The method of claim 1, further comprising the step of (d) characterizing said population of modified peptides isolated in step (c) by mass spectrometry (MS), tandem mass spectrometry (MS—MS), and/or MS³ analysis.

3. The method of claim 2, wherein said mass spectrometry comprises matrix-assisted laser desorption time-of-flight (MALDI-TOF) MS, wherein said tandem mass spectrometry comprises liquid chromatography (LC)-MS/MS, and wherein said MS³ analysis comprises LC-MS³.

4. The method of claim 2, wherein said immobilized antibody of step (b) is immobilized in chromatography resin within a column, said column being coupled to a mass spectrometer for said characterization of step (d).

5. The method of claims 2 or 3, further comprising the step of (e) utilizing a search program to substantially match the spectra obtained for said moditied peptides during the characterization of step (d) with the spectra for a known peptide sequences, thereby identifying the parent protein(s) of said modified peptides.

6. The method of claim 5, wherein at least one modified peptide characterized in step (d) comprises an unknown post-translational modification site of said parent protein.

7. The method of claim 5, further comprising the step of (f) quantifying at least one isolated post-translationnally modified peptide of step (d).

8. The method of claim 7, wherein step (f) comprises quantifying said isolated post-translationally modilied peptide using stable isotope labeling by amino acids in cell culture (SILAC) and/or absolute quantification of peptides (AQUA) techniques.

9. The method of claims 2 or 3, further comprising the step of (c) comparing the modification state of at least one modified peptide characterized in step (d) with the modilication state of a corresponding peptide in a reference sample, thereby to compare protein activation in said proteinaceous preparation with protein activation in said reference sample.

10. The method of claim 9, wherein said proteinaccous preparation corresponds to a diseased organism and said reference sample corresponds to a normal organism, whereby comparison of protein activation provides information on activation changes resulting from said disease.

11. The method of claim 10, wherein the comparison of protein activation identities at least one modified peptide characterized in step (d) as corresponding to a parent protein not previously reported as so modified in said disease.

12. The method of claim 9, wherein said proteinaccous preparation is obtained from a tissue biopsy cell or a clinical fluid sample and said reference sample corresponds to a diseased organism, whereby the comparison of protein activation provides information useful for diagnosis of said disease.

13. The method of claim 9, wherein said protein preparation corresponds with an organism or preparation treated with at least one test compound and said reference sample corresponds with an untreated organism or preparation, whereby the comparison of protein activation provides information on activation changes resulting from treatment with said test compound.

14. The method of claim 12 or 13, wherein said disease is cancer.

15. The method of claim 13, wherein said test compound comprises a cancer therapeutic.

16. The method of claim 13, wherein said test compound comprises a kinase inhibitor.

17. The method of claim 1, wherein said proteinaceous preparation comprises a digested biological sample selected from the group consisting of a digested crude cell extract, a digested tissue sample, a digested serum sample, a digested urine sample, a digested synovial fluid sample, and a digested spinal fluid sample.

18. The method of claim 17, wherein said digested preparation is obtained using at least one proteolytic enzyme or chemical cleavage.

19. The method of claim 18, wherein said proteolytic enzyme is immobilized.

20. The method of claim 18, wherein said proteolytic enzyme is soluble, and wherein said digested preparation is treated with a proteolysis inhibitor prior to said contacting step (b).

21. The method of claim 1, wherein step (a) further comprises pre-purifying said proteinaceous preparation by immobilized metal affinity chromatography (IMAC).

22. The method of claim 1, wherein said immobilized antibody of step (b) is covalently-linked to a chromatography resin or noncovalently-linked to protein-A- or protein-G-agarose.

23. The method a claim 22, wherein said resin is contained within a column or micropipette tip.

24. The method of claim 1, wherein said modification comprises phosphorylation.

25. The method of claim 1, wherein said modified peptide (s) comprise(s) a phosphopeptide.

26. The method of claim 1, wherein said post-translational modification-specific antibody comprises a motif-specific, context-independent antibody that specifically binds a motif comprising at least one phosphorylated amino acid.

27. The method of claim 26, wherein said motif consists of a single phosphorylated amino acid.

28. The method of claim 26, wherein said motif consists of all or part of a kinase consensus substrate motif or a protein-protein binding motif.

29. The method of claim 28, wherein said kinase consensus substrate motif is selected from the group consisting of mitogen-activated protein kinase (MAPK) consensus substrate motifs, cyclin-dependent kinase (CDK) consensus substrate motifs, protein kinase A (PKA) consensus substrate motifs, AKT consensus substrate motifs, protein kinase C (PKC) consensus substrate motifs, phosphothreonine-X-arginine, and ATM (ataxia telangiecstasia mutated) consensus substrate motifs, and wherein said protein-protein binding is a 14-3-3 binding motif or a 3-phosphoinositide-dependent kinase 1 (PDK1) docking motif.

30. The method of claim 1, wherein said post-translational modification specific antibody is a monoclonal antibody or a polyclonal antibody.

31. The method of claim 1, wherein at least one modified peptide isolated in step (c) corresponds to a known marker of disease.

32. The method of claim 1, wherein said reversed-phased chromatography of step (a) comprises a C18 column.

33. The method of claim 1, wherein said immobilized post-translational modification specific antibody comprises an antibody that binds a single modified amino acid selected from the group consisting of an acetylated amino acid, a glycosylated amino acid, and a methylated amino acid.

34. A method for isolating a target population of phosphopeptides from a complex mixture of peptides, said method comprising the steps of:

(a) obtaining a digested proteinaceous preparation from an organism, wherein said digested proteinaceous preparation comprises a complex mixture of peptides comprising phosphopeptides from two or more different proteins;

(b) fractionating phosphopeptides in said digested proteinaceous preparation by reversed-phased chromatography to produce a fractionated proteinaceous preparation;

(c) contacting said fractionated proteinaceous preparation with at least one immobilized motif-specific, context-independent antibody that binds a motif comprising at least one phosphorylated amino acid;

(d) isolating said target population of phosphopeptides specifically bound by said immobilized antibody in step (c); and (e) characterizing said population of phosphopeptides isolated in step (d) by mass spectrometry (MS), tandem mass spectrometry (MS—MS), and/or $MS^3$ analysis.

35. The method of claim 34, further comprising the step of (f) utilizing a search program to substantially match the mass spectra obtained for at least one phosphopeptide during the characterization of step (e) with the mass spectra for a peptide of one or more known protein(s), thereby identifying the parent protein(s) of said phosphopeptide.

36. The method of claim 34, wherein said mass spectrometry comprises matrix-assisted laser desorption time-or-flight (MALDI-TOF) MS, wherein said tandem mass spectrometry comprises liquid chromatography (LC)-MS/MS, and wherein said $MS^3$ analysis comprises $LC-MS^3$.

37. The method of claim 34, wherein step (a) further comprises digesting said proteinaceous preparation to produce a complex mixture of peptides.

38. The method of claim 34, wherein said motif-specific, context-independent antibody of step (c) comprises a general phosphotyrosine-specific antibody, a general phosphothreonine-specific antibody, or a general phosphoserine-specific antibody.

39. The method of claim 34, wherein said motif-specific, context-independent antibody of step (c) is specific for a phosphorylated kinase consensus substrate motif or protein-protein binding motif.

40. The method of claim 39, wherein said kinase consensus substrate motif is selected from the group consisting of mitogen-activated protein kinase (MAPK) consensus substrate motifs, cyclin-dependent kinase (CDK) consensus substrate motifs, protein kinase A (PKA) consensus substrate motifs, AKT consensus substrate motifs, protein kinase C (PKC) consensus substrate motifs, phosphothreonine-X-arginine, and ATM/ATR (ataxia telangiecstasia mutated/ataxia telangiecstasia and Rad3-related) consensus substrate motifs, p85 P13K binding motif, phosphothreonine-proline motif, Arg-X-Tyr/Phe-X-phosphoserine motif, phosphoserine/phosphothreonine-Phe motif, polo-like kinase (PLK) consensus substrate motifs and DNA damage-induced substrate motifs, and wherein said protein-protein binding is a 14-3-3 binding motif or a 3-phosphoinositide-dependent kinase 1 (PDK 1) docking motif.

41. The method of claim 34, wherein said reversed-phased chromatography of step (b) comprises a C18 column.

42. The method of claim 34, further comprising the step of (f) quantifying said isolated phosphopeptides of step (c).

43. The method of claim 42, wherein step (f) comprises quantifying said isolated phosphopeptides using stable isotope labeling by amino acids in cell culture (SILAC) and/or absolute quantification of peptides (AQUA) techniques.

* * * * *